US007393922B2

(12) United States Patent
Dean et al.

(10) Patent No.: US 7,393,922 B2
(45) Date of Patent: Jul. 1, 2008

(54) INSECTICIDAL CRY4BA PROTEINS WITH ENHANCED TOXICITY

(75) Inventors: Donald H. Dean, Columbus, OH (US); Mohd Amir Abdullah, Athens, GA (US)

(73) Assignee: The Ohio State University Research Foundation, Columbus, OH (US)

(*) Notice: Subject to any disclaimer, the term of this patent is extended or adjusted under 35 U.S.C. 154(b) by 142 days.

(21) Appl. No.: 10/929,754

(22) Filed: Aug. 30, 2004

(65) Prior Publication Data

US 2005/0124803 A1 Jun. 9, 2005

Related U.S. Application Data

(60) Provisional application No. 60/498,826, filed on Aug. 29, 2003.

(51) Int. Cl.
*C07K 5/00* (2006.01)
*C07H 21/02* (2006.01)
*C12H 15/63* (2006.01)
*C12N 1/12* (2006.01)

(52) U.S. Cl. .................. 530/350; 536/23.1; 435/320.1; 435/252.1

(58) Field of Classification Search ........................ None
See application file for complete search history.

(56) References Cited

U.S. PATENT DOCUMENTS

| | | | |
|---|---|---|---|
| 6,017,534 | A | 1/2000 | Malvar et al. |
| 6,110,464 | A | 8/2000 | Malvar et al. |
| 6,204,246 | B1 | 3/2001 | Bosch et al. |
| 6,242,241 | B1 | 6/2001 | Malvar et al. |
| 6,521,442 | B2 | 2/2003 | Malvar et al. |
| 6,576,455 | B1 | 6/2003 | Kakefuda et al. |
| 6,593,273 | B2 | 7/2003 | Asrar et al. |
| 6,797,490 | B2 | 9/2004 | Bulla, Jr. |
| 2002/0197689 | A1 | 12/2002 | Corzo et al. |
| 2003/0054391 | A1 | 3/2003 | Bulla, Jr. et al. |

OTHER PUBLICATIONS

Guo et al. (2004) Proc. Natl. Acad. Sci. USA 101: 9205-9210.*
Lazar et al(1988) Mol. Cell. Biol. 8:1247-1252.*
Hill et al. (1998) Biochem. Biophys. Res. Comm. 244:573-577.*
Kalman et al. (1993) Applied and Environmental Microbiology, vol. 59, p. 1131-1137.*
Abdullah et al. (Sep. 2003) Applied and Environmental Microbiology, vol. 69, p. 5343-5353.*
Kamauchi et al. (2003) Biosci, Biotechnol. Biochem., vol. 67, p. 94-99.*
Dean et al. (1996) Probing the mechanism of action of *Bacillus thuringiensis* insecticidal proteins by site-directed mutagenesis-a minireview, Gene, vol. 179, p. 111-117.*
Abdul-Rauf et al. (1999) Mutations of Loop 2 and Loop 3 Residues in Domain II of *Bacillus thuringiensis* Cry1C d-Endotoxin Affect Insecticidal Specificity and Initial Binding to *Spodoptera littoralis* and *Aedes aegypti* Midgut Membranes, vol. 39, p. 94-98.*

Schnepf, et al., "*Bacillus thuringiensis* and Its Pesticidal Crystal Proteins," Microbiology and Molecular Biology Reviews, Sep. 1998, p. 775-806, vol. 62, No. 3.
Batzer, M. A.et al. (1991) "Enhanced evolutionary PCR using oligonucleotides with inosine at the 3'-terminus". Nucleic Acids Research 19: 5081.
Guex, N. et al., "SWISS-MODEL and the Swiss Polb viewer: An environment for comparative protein modelling". Electrophoresis, vol. 18, pp. 2714-2723 (1997).
Chungjatupornchai, et al., "Common features of *Bacillus thuringiensis* toxins specific for Diptera and Lepidoptera", Eur. J. Biochem, 173: 9-16, (1988).
Ohtsuka et al "An alternative approach to deoxyoligonucleotides as hybridization probes by insertion of deoxyinosine at ambiguous codon positions" J Biol Chem 260 2605-8 1985.
Rosso et al., "Contribution of the 65-kilodalton protein encoded by the cloned gene cry19A to the mosquitocidal activity of *Bacillus thuringiensis* subsp. Jegathesan", Appl. Environ, Microbiol. 63: 4449-4455 (1997).
Rossolini et al., Mol. Cell. Probes 8: 91-98, (1994).
Yamagiwa et al, "Activation process of dipteran-specific insecticidal protein produced by *Bacillus thuringiensis* subsp. Israelensis" Appl Environ Microbiol 65: 3464-346 1999.
Smedley et al, "Mutagenesis of three surface-exposed loops of a *Bacillus thuringiensis* insecticidal toxin reveals residues important for toxicity, receptor recognition and possibly membrane insertion", Microbiology, vol. 142, 1617-1624 (1996).
Boonserm, P. et al., "Crystal Structure of the Mosquito-larvicidal Toxin Cry4Ba and its Biological Implications", J. Mol Biol. 348, pp. 363-382, 2005.
Dayoff, MO et al., "A Model of Evolutionary Change in Proteins", In M.O. Dayoff (ed) Atlas of the Protein Sequence and Structure, vol. 5, pp. 345-352 (1978).
Abdullah, et al., "Characterization of Toxicity Determinants in *Bacillus thuringiensis* Mosquitocidal Delta-Endotoxins", Dissertation, The Ohio State University (2002).
Abdullah "Enhancement of Cry19Aa Mosquitocidal Activity Against Aedes Aegypti by Mutations in the Putative Loop Regions of Domain II" Appl Environ Microbiol 2004, vol. 70, No. 6 pp. 3769-3771.

(Continued)

*Primary Examiner*—Richard Hutson
*Assistant Examiner*—Alexander D Kim
(74) *Attorney, Agent, or Firm*—Calfee, Halter & Griswold LLP

(57) ABSTRACT

The present invention relates generally to modified *Bacillus thuringiensis* (Bt) insecticidal crystal proteins, also referred to as mutant toxins, with enhanced toxicity against a variety of insect genera, particularly mosquitos. The invention provides modified Bt Cry4Ba proteins, or mutant toxins, which have toxicity-enhancing sequence modifications at one or more positions within the amino acid sequence of the protein. The invention also provides polynucleotides encoding modified Cry4Ba proteins. The invention also provides insecticidal compositions comprising mutant toxins with a new or broadened insecticidal spectrum, and insecticidal compositions comprising polynucleotides encoding the modified Cry4Ba proteins.

29 Claims, 24 Drawing Sheets

OTHER PUBLICATIONS

Almond, et al., "Structural Stability of *Bacillus thuringiensis* δ-Endotoxin Homolog-Scanning Mutants Determined by Susceptibility to Proteases", Applied and Environmental Microbiology, (1993), vol. 59, No. 8, pp. 2442-2448.

Audtho, et al., "Production of Chymotripsin-Resistant *Bacillus thuringiensis* Cry2Aa1-Endotoxin by Protein Engineering", Applied and Environmental Biology, (1999), vol. 65, No. 10, pp. 4601-4605.

Freeman, Biological Science, 2nd edition, Protein Structure and Function, Chapter 3, p. 51, Figure 3.5, 2005.

Jenkins, et al., "Binding Specificity of *Bacillus thuringiensis* CryIAa for Purified Native Bombyx Mori Aminopeptidase N and Cadherin-Like Receptors", BMC Biochemistry, (2001), vol. 2, p. 12.

Lee et al "Location of a Bombyx Mori Receptor Binding Region on a *Bacillus thuringiensis*-Endotoxin" The Journal of Biological Chemistry (1992), vol. 267, No. 5, pp. 3115-3121.

Lee et al "Determination of Binding of *Bacillus thuringiensis*-Endotoxin Receptors to Rice Stem Borer Midguts" Applied and Environmental Biology (1997) vol. 63 No. 4 p. 1453-1459.

Lertcanawanichakul, et al., "Expression of Chitinase-Encoding Genes in *Bacillus thuringiensis* and Toxicity of Engineered B. Thuringiensis Subsp. Alzawai Toward Lymantria Dispar Larvae", Curr. Microbiol., (2004), vol. 48, No. 3, pp. 175-181.

Lu, et al., "Identification of Amino Acid Residues of *Bacillus thuringiensis* δ-Endotoxin CryIAa Associated with Membrane Binding and Toxicity to Bombyx Mori", Journal of Bacteriology, (1994), vol. 176, No. 17, pp. 5554-5559.

Dean, DH et al., "Rational Design of Cry Toxins"; Biotechnonogy of *Bacillus thuringiensis* and its Environmental Impact. (2002) Squigly Gum Press, pp. 112-117.

Jenkins et al "Bivalent Sequential Binding Model of a *Bacillus thuringiensis* toxin to gypsy moth aminoipeptidase N receptor" J. Bio. Chem. vol. 275, No. 19, issue May 12, 2000.

Rajamohan, F et al, "Single Amino Acid Changes in Domain II of *Bacillus thuringiensis* cryIAb δ-Endotoxin Affect irrefersible binding to manduca sexta midgut membrane vesicle" J. Bacteriology, May 1995, pp. 2276-2282, vol. 177, No. 9.

Rajamohan, et al., "Role of Domain II, Loop 2 residues of *Bacillus thuringiensis* cryIAb δ-Endotoxin in reversible and irreversible binding to manduca sexta and heliothis virescens", J. Bio. Bhem. vol. 271, No. 5, Feb. 2, 1996, 2390-2396.

Rajamohan et al., "Protein engineering of *Bacillus thuringiensis* δ-endotoxin: mutations at domain II of CryIAb enhance receptor affinity and toxicity toward gypsy moth larve", Proc. Natl. Acad. Sci, USA, vol. 93, pp. 14338-14343, Dec. 1996, Applied Biological Sciences.

Wu, et al., "Functional significance of loops in the receptor binding domain of *Bacillus thuringiensis* CryIIIA δ-endotoxin", J. Mol. Biol. 255, 1996, pp. 628-640.

Jenkins et al., "Exploring the Mechanism of action of insecticidal proteins by genetic engineering methods", Genetic Engineering, vol. 22, 2000, pp. 33-54.

Rajamohan, F, et al, "Molecular Biology of Baceteria for the Biological Control of Insects" pp. 105-122, In M. Gunasekaran and DJ Weber (eds.), Molecular Biology of the Biological Control of Pests and Diseases of Plants, 1996.

Rajamohan et al., "*Bacillus thuringiensis* Insecticidal Proteins: Molecular Mode of Action", Progress in Nucleic Acid Research and Molecular Biology, vol. 60, pp. 1-27, 1998.

Rajamohan et al., "Mutations at domain II, Loop 3, of *Bacillus thuringiensis* CryIAa and CryIAb δ-Endotoxins suggest loop 3 is involved in initial binding to lepidopteran midguts", J. Bio. Chem. vol. 271, No. 41, Oct. 11, 1996, 25220-25226.

Dean, et al., "Protein Engineering and Biopesticides", Regional Biopesticide symposium, Oct. 16-18, 2002, Mahidol University, Bangkok, Thailand.

* cited by examiner

FIGURE 1 Cry 4Ba AMINO ACID SEQUENCE

```
                            MNSGYPLANDLQGSMKNTNYKDWLAMCENNQQYGVNPAAINSSSV   45
STALKVAGAILKFVNPPAGTVLTVLSAVLPILWPTNTPTPERVWNDFMTNTGNLIDQTV  104
TAYVRTDANAKMTVVKDYLDQYTTKFNTWKREPNNQSYRTAVITQFNLTSAKLRETAVY  163
FSNLVGYELLLLPIYAQVANFNLLLIRDGLINAQEWSLARSAGDQLYNTMVQYTKEYIA  222
HSITWYNKGLDVLRNKSNGQWITFNDYKREMTIQVLDILALFASYDPRRYPADKIDNTK  281
LSKTEFTREIYTALVESPSSKSIAALEAALTRDVHLFTWLKRVDFWTNTIYQDLRFLSA  340
NKIGFSYTNSSAMQESGIYGSSGFGSNLTHQIQLNSNVYKTSITDTSSPSNRVTKMDFY  399
KIDGTLASYNSNITPTPEGLRTTFFGFSTNENTPNQPTVNDYTHILSYIKTDVIDYNSN  458
RVSFAWTHKIVDPNNQIYTDAITQVPAVKSNFLNATAKVIKGPGHTGGDLVALTSNGTL  517
SGRMEIQCKTSIFNDPTRSYGLRIRYAANSPIVLNVSYVLQGVSRGTTISTESTFSRPN  576
NIIPTDLKYEEFRYKDPFDAIVPMRLSSNQLITIAIQPLNMTSNNQVIIDRIEIIPITQ  635
SVLDETENQNLESEREVVNALFTNDAKDALNIGTTDYDIDQAANLVECISEELYPKEKM  694
LLLDEVKNAKQLSQSRNVLQNGDFESATLGWTTSDNITIQEDDPIFKGHYLHMSGARDI  753
DGTIFPTYIFQKIDESKLKPYTRYLVRGFVGSSKDVELVVSRYGEEIDAIMNVPADLNY  812
LYPSTFDCEGSNRCETSAVPANIGNTSDMLYSCQYDTGKKHVVCQDSHQFSFTIDTGAL  871
DTNENIGVWVMFKISSPDGYASLDNLEVIEEGPIDGEALSRVKHMEKKWNDQMEAKRSE  930
TQQAYDVAKQAIDALFTNVQDEALQFDTTLAQIQYAEYLVQSIPYVYNDWLSDVPGMNY  989
DIYVELDARVAQARYLYDTRNIIKNGDFTQGVMGWHVTGNADVQQIDGVSVLVLSNWSA 1048
GVSQNVHLQHNHGYVLRVIAKKEGPGNGYVTLMDCEENQEKLTFTSCEEGYITKTVDVF 1107
PDTDRVRIEIGETEGSFYIESIELICMNE"                              1136
```

FIGURE 2 Cry 4Ba POLYNUCLEOTIDE SEQUENCE

```
GATAAGAATT GTTCATAGGA ATCCGTATCA ATTTTTTCAA GGAATATGTA TTTGCACTTT    60
TGGTCTTTTT AAATCGTATG AATTCAAAAT AGTTTATATC AATCTTTGTT ACACCAGAAA   120
AAGATTGTAT CCAATGTGAA TATGGGAGGA ATAAATATGA ATTCAGGCTA TCCGTTAGCG   180
AATGACTTAC AAGGGTCAAT GAAAAACACG AACTATAAAG ATTGGCTAGC CATGTGTGAA   240
AATAACCAAC AGTATGGCGT TAATCCAGCT GCGATTAATT CTTCTTCAGT TAGTACCGCT   300
TTAAAAGTAG CTGGAGCTAT CCTTAAATTT GTAAACCCAC CTGCAGGTAC TGTCTTAACC   360
GTACTTAGCG CGGTGCTTCC TATTCTTTGG CCGACTAATA CTCCAACGCC TGAAAGAGTT   420
TGGAATGATT TCATGACCAA TACAGGGAAT CTTATTGATC AAACTGTAAC AGCTTATGTA   480
CGAACAGATG CAAATGCAAA AATGACGGTT GTGAAAGATT ATTTAGATCA ATATACAACT   540
AAATTAACA CTTGGAAAAG AGAGCCTAAT AACCAGTCCT ATAGAACAGC AGTAATAACT   600
CAATTAACT TAACCAGTGC CAAACTTCGA GAGACCGCAG TTTATTTTAG CAACTTAGTA   660
GGTTATGAAT TATTGTTATT ACCAATATAC GCACAAGTAG CAAATTTCAA TTTTACTTTA   720
ATAAGAGATG GCCTCATAAA TGCTCAAGAA TGGTCTTTAG CACGTAGTGC TGGTGACCAA   780
CTATATAACA CTATGGTGCA GTACACTAAA GAATATATTG CACATAGCAT TACATGGTAT   840
AATAAAGGTT TAGATGTACT TAGAAATAAA TCTAATGGAC AATGGATTAC GTTAATGAT    900
TATAAAAGAG AGATGACTAT TCAAGTATTA GATATACTCG CTCTTTTTGC CAGTTATGAT   960
CCACGTCGAT ACCCTGCGGA CAAAATAGAT AATACGAAAC TATCAAAAAC AGAATTACA   1020
AGAGAGATTT ATACAGCTTT AGTAGAATCT CCTTCTAGTA AATCTATAGC AGCACTGGAG   1080
GCAGCACTTA CACGAGATGT TCATTATTC ACTTGGCTAA AGAGAGTAGA TTTCTGGACC   1140
AATACTATAT ATCAAGATTT AAGATTTTTA TCTGCCAATA AAATTGGGTT TCATATACA   1200
AATTCTTCTG CAATGCAAGA AAGTGGAATT TATGGAAGTT CTGGTTTTGG TTCAAATCTT   1260
ACTCATCAAA TTCAACTTAA TTCTAATGTT TATAAAACTT CTATCACAGA TACTAGCTCC   1320
CCCTCTAATC GAGTTACAAA AATGGATTTC TACAAAAATTG ATGGTACTCT TGCCTCTTAT   1380
AATTCAAATA TAACACCAAC TCCTGAAGGT TTAAGGACCA CATTTTTTGG ATTTTCAACA   1440
AATGAGAACA CACCTAATCA ACCAACTGTA AATGATTATA CGCATATTTA AAGCTATATA   1500
AAAACTGATG TTATAGATTA TAACAGTAAC AGGGTTTCAT TTGCTTGGAC ACATAAGATT   1560
GTTGACCCTA ATAATCAAAT ATACACAGAT GCTATCACAC AAGTTCCGGC CGTAAAATCT   1620
```

FIGURE 2 Cry 4Ba POLYNUCLEOTIDE SEQUENCE (continued)

```
AACTTCTTGA ATGCAACAGC TAAAGTAATC AAGGGACCTG GTCATACAGG GGGGGATCTA 1680
GTTGCTCTTA CAAGCAATGG TACTCTATCA GGCAGAATGG AGATTCAATG TAAAACAAGT 1740
ATTTTTAATG ATCCTACAAG AAGTTACGGA TTACGCATAC GTTATGCTGC AAATAGTCCA 1800
ATTGTATTGA ATGTATCATA TGTATTACAA GGAGTTTCTA GAGGAACAAC GATTAGTACA 1860
GAATCTACGT TTTCAAGACC TAATAATATA ATACCTACAG ATTTAAAATA TGAAGAGTTT 1920
AGATACAAAG ATCCTTTTGA TGCAATTGTA CCGATGAGAT TATCTTCTAA TCAACTGATA 1980
ACTATAGCTA TTCAACCATT AAACATGACT TCAAATAATC AAGTGATTAT TGACAGAATC 2040
GAAATTATTC CAATCACTCA ATCTGTATTA GATGAGACAG AGAACCAAAA TTTAGAATCA 2100
GAACGAGAAG TTGTGAATGC ACTGTTTACA AATGACGCGA AAGATGCATT AAACATTGGA 2160
ACGACAGATT ATGACATAGA TCAAGCCGCA AATCTTGTGG AATGTATTTC TGAAGAATTA 2220
TATCCAAAAG AAAAAATGCT GTTATTAGAT GAAGTTAAAA ATGCGAAACA ACTTAGTCAA 2280
TCTCGAAATG TACTTCAAAA CGGGGATTTT GAATCGGCTA CGCTTGGTTG GACAACAAGT 2340
GATAATATCA CAATTCAAGA AGATGATCCT ATTTTTAAAG GGCATTACCT TCATATGTCT 2400
GGGGCGAGAG ACATTGATGG TACGATATTT CCGACCTATA TATTCCAAAA AATTGATGAA 2460
TCAAAATTAA AACCGTATAC ACGTTACCTA GTAAGGGGAT TTGTAGGAAG TAGTAAAGAT 2520
GTAGAACTAG TGGTTTCACG CTATGGGGAA GAAATTGATG CCATCATGAA TGTTCCAGCT 2580
GATTTAAACT ATCTGTATCC TTCTACCTTT GATTGTGAAG GGTCTAATCG TTGTGAGACG 2640
TCCGCTGTGC CGGCTAACAT TGGGAACACT TCTGATATGT TGTATTCATG CCAATATGAT 2700
ACAGGGAAAA AGCATGTCGT ATGTCAGGAT TCCCATCAAT TTAGTTTCAC TATTGATACA 2760
GGGGCATTAG ATACAAATGA AAATATAGGG GTTTGGGTCA TGTTTAAAAT ATCTTCTCCA 2820
GATGGATACG CATCATTAGA TAATTTAGAA GTAATTGAAG AAGGGCCAAT AGATGGGGAA 2880
GCACTGTCAC GCGTGAAACA CATGGAGAAG AAATGGAACG ATCAAATGGA AGCAAAACGT 2940
TCGGAAACAC AACAAGCATA TGATGTAGCG AAACAAGCCA TTGATGCTTT ATTCACAAAT 3000
GTACAAGATG AGGCTTTACA GTTTGATACG ACACTCGCTC AAATTCAGTA CGCTGAGTAT 3060
TTGGTACAAT CGATTCCATA TGTGTACAAT GATTGGTTGT CAGATGTTCC AGGTATGAAT 3120
TATGATATCT ATGTAGAGTT GGATGCACGA GTGGCACAAG CGCGTTATTT GTATGATACA 3180
AGAAATATTA TTAAAAATGG TGATTTTACA CAAGGGGTAA TGGGGTGGCA TGTAACTGGA 3240
```

FIGURE 2 Cry 4Ba POLYNUCLEOTIDE SEQUENCE (continued)

```
AATGCAGACG TACAACAAAT AGATGGTGTT TCTGTATTGG TTCTATCTAA TTGGAGTGCT 3300
GGCGTATCTC AAAATGTCCA TCTCCAACAT AATCATGGGT ATGTCTTACG TGTTATTGCC 3360
AAAAAAGAAG GACCTGGAAA TGGGTATGTC ACGCTTATGG ATTGTGAGGA GAATCAAGAA 3420
AAATTGACGT TTACGTCTTG TGAAGAAGGA TATATTACGA AGACAGTAGA TGTATTCCCA 3480
GATACAGATC GTGTACGAAT TGAGATAGGC GAAACCGAAG GTTCGTTTTA TATCGAAAGC 3540
ATTGAATTAA TTTGCATGAA CGAGTGATTA ATAAAAAATA ACTAAAGCTT TAAAAACCAT 3600
GGAGAAAGTT TTCTCCATGG TTTTTAATTT CTGCATTTAT TAATTCTGGT ACAAAAAATA 3660
TATAGAAAAC ATAAAAAATA GATA3684
```

FIGURE 3 Cry19Aa AMINO ACID SEQUENCE

```
              MHYYGNRNEYDILNASSNDSNMSNTYPRYPLANPQQDLMQNTNYK    45
DWLNVCEGYHIENPREASVRAGLGKGLGIVSTIVGFFGGSIILDTIGLFYQISELLWPE   104
DDTQQYTWQDIMNHVEDLIDKRITEVIRGNAIRTLADLQGKVDDYNNWLKKWKDDPKST   163
GNLSTLVTKFTALDSDFNGAIRTVNNQGSPGYELLLLPVYAQIANLHLLLLRDAQIYGD   222
KWWSARANARDNYYQIQLEKTKEYTEYCINWYNKGLNDFRTAGQWVNFNRYRREMTLTV   281
LDIISMFPIYDARLYPTEVKTELTREIYSDVINGEIYGLMTPYFSFEKAESLYTRAPHL   340
FTWLKGFRFVTNSISYWTFLSGGQNKYSYTNNSSINEGSFRGQDTDYGGTSSTINIPSN   399
SYVYNLWTENYEYIYPWGDPVNITKMNFSVTDNNSSKELIYGAHRTNKPVVRTDFDFLT   458
NKEGTELAKYNDYNHILSYMLINGETFGQKRHGYSFAFTHSSVDPNNTIAANKITQIPV   517
VKASSINGSISIEKGPGFTGGDLVKMRADSGLTMRFKAELLDKKYRVRIRYKCNYSSKL   576
ILRKWKGEGYIQQQIHNISPTYGAFSYLESFTITTTENIFDLTMEVTYPYGRQFVEDIP   635
SLILDKIEFLPTN                                                648
```

FIGURE 4 Cry 19Aa POLYNUCLEOTIDE SEQUENCE

```
GAAAATTCGA GAATTAATCA GACATGCAGG CGCCAAAAAC GTAGTATTGG ATGGCAGAGA   60
TGGAGTAATG AATATCTCTA TGGTGTACTA GGGCTCTATT GGGACTGGAA AGTTCGTCCC  120
CTTGAAAGCT CAGGAAGATA TTGATAAAAG TGTCTGCCAT TTGATAGGTC TCATAACCCT  180
TTTGATGAAG TTTATGGGGT GAGCTGCTTG AGGGAAAACC TCACGAGCAG TTCTTATGGG  240
GAGGGGCTGG AAACGGGTTA TAACTGATAC CGCGCCAGTC CTTTACCCGA CAACGAACTT  300
TTGCTTGGTT AGAAAATTAC CGCAGGCTTT GGAAAAACTG TGAACGAACA CTTGAAAATA  360
GCAGACAAAG TTGCTTATTG GCAGCTGTGG CTATTTTATT AAAAAGATTC CAAACAGGTT  420
CTCAGAAAAT AGTTGTAATT CATCTTGAAT CGAAAGATTC ATAAAAAACG TCATCCTTTC  480
TAGCTTTTTA GAAAGAATAA CGTTTTTTGA CACTTGGGGG TAGTCTTATT TCTTAAGTTG  540
ATGGGCATGC AACAGAACCC TAAAAAATCA ATAATTCAAC AAAAATAATG GGGATATTTG  600
TTGAATTATT GCAACAGGAA TACATACGTA GATTGCGAAT ATTTAGAAGT ACACCCTACA  660
TATTATTGGT TAGGTGGAAT GAATTATAAA AAATGATGGG AATAAGGGAG GAACGAAGAT  720
GCATTATTAT GGGAATAGGA ATGAATATGA CATATTAAAT GCTTCATCAA ACGATTCAAA  780
CATGTCTAAT ACTTATCCGA GGTATCCGTT AGCAAATCCA CAACAAGATT TAATGCAAAA  840
TACAAATTAT AAAGATTGGC TTAATGTATG TGAAGGGTAT CATATAGAAA ATCCTAGAGA  900
AGCAAGCGTT AGAGCTGGAC TTGGTAAGGG ATTAGGTATA GTTAGTACAA TCGTAGGGTT  960
CTTTGGTGGT TCTATTATCT TAGATACAAT TGGATTGTTT TACCAAATTT CAGAGCTACT 1020
TTGGCCAGAG GATGATACCC AGCAATACAC TTGGCAAGAT ATTATGAATC ATGTAGAAGA 1080
TCTTATAGAC AAACGAATAA CTGAGGTTAT ACGAGGAAAT GCAATTAGAA CATTAGCAGA 1140
TTTACAGGGT AAAGTTGATG ATTATAACAA TTGGTTGAAG AAATGGAAAG ACGATCCAAA 1200
ATCTACAGGT AATTTAAGCA CCTTAGTAAC CAAGTTTACG GCTCTTGATT CAGATTTTAA 1260
TGGTGCTATA AGGACAGTTA ATAATCAGGG GAGTCCAGGT TATGAGTTAC TTTTATTGCC 1320
TGTCTATGCA CAAATTGCGA ATCTGCATTT ACTTTTATTA CGGGATGCTC AGATTTATGG 1380
AGATAAATGG TGGAGCGCAC GAGCTAATGC TCGTGATAAT TATTACCAAA TACAATTAGA 1440
GAAAACAAAG GAATATACAG AATATTGTAT AAATTGGTAT AATAAGGGTT TAAATGATTT 1500
TAGAACAGCA GGTCAATGGG TAAACTTTAA TCGTTATCGT AGAGAAATGA CTCTTACTGT 1560
ATTAGATATT ATTTCAATGT TCCCTATTTA TGACGCGAGA TTATATCCTA CAGAAGTAAA 1620
```

FIGURE 4 Cry19Aa POLYNUCLEOTIDE SEQUENCE (continued)

```
AACCGAACTA ACTAGGGAAA TTTATTCAGA TGTTATTAAT GGGGAGATAT ATGGACTTAT 1680
GACTCCTTAT TTTTCTTTTG AGAAAGCTGA ATCACTTTAT ACAAGGGCAC CCCATCTCTT 1740
CACTTGGCTA AAAGGATTC GATTTGTAAC CAATTCTATT TCTTATTGGA CATTTTATC 1800
AGGTGGTCAA AATAAGTATT CTTATACTAA TAATTCTAGT ATTAACGAGG GCTCTTTTAG 1860
GGGACAGGAC ACAGATTATG GTGGGACTTC TTCTACCATT AATATTCCAT CAAATTCGTA 1920
TGTATATAAT TTATGGACGG AAAATTATGA ATATATTTAT CCTTGGGGTG ATCCTGTAAA 1980
TATTACAAAA ATGAATTTTT CTGTAACAGA TAATAATTCT TCAAAAGAAT TAATTATGG 2040
TGCACACAGA ACGAATAAAC CTGTTGTTCG GACAGATTTT GATTTTCTCA CTAATAAAGA 2100
GGGAACTGAG TTAGCAAAAT ATAATGATTA TAATCATATT TTATCCTATA TGTTAATTAA 2160
TGGGGAAACG TTTGGTCAGA AACGTCATGG TTATTCGTTT GCTTTTACAC ATAGTAGTGT 2220
TGATCCTAAT AATACCATTG CAGCGAATAA AATTACGCAA ATTCCTGTAG TGAAAGCTTC 2280
GAGTATAAAT GGATCGATTT CAATTGAAAA AGGTCCCGGA TTTACGGGAG GAGATTTGGT 2340
AAAGATGAGA GCAGATTCAG GTTAACTAT GCGTTTAAA GCTGAATTAT TAGATAAAAA 2400
ATATCGTGTT CGAATACGTT ATAAATGTAA CTACAGTTCT AAATTAATAC TACGAAAATG 2460
GAAAGGGGAA GGTTATATAC AACAACAAAT TCTCCCACAT TCTCCCACAT ATGGAGCCTT 2520
TTCTTATTTA GAGTCTTTTA CTATAACTAC GACAGAAAAT ATATTTGATT TGACAATGGA 2580
GGTAACATAT CCGTATGGTA GACAGTTTGT TGAAGATATA CCATCTCTTA TATTAGATAA 2640
AATCGAATTC CTCCCCAACTA ACTGATACCA TTCCACAGGAA ATATGAGGAA AAATATGAAT 2700
TAGAAAGATC ACAGGAAACA TTTAATAGTA TATTGTTGA TTAAAACAAA GTACTAACGT 2760
AGATGGTATA GCTGTTTGAA AAAATAAGAA AAAAGGTTGT GAATTTTATG CTTACAAGTG 2820
GTGCGAAAAA TATGTTAAAA CTCGAAACGA CAGATTATGA AATAGATCAA ATGGCGAATG 2880
CTATAGAAAA TATGTCAGGT GAACAATATT CACAGGAAAA AATGATGCAA TGGCATGACA 2940
TAAAATATGC CAAACAATTG AGTCAAGCAC GTAATTACT TCAAAATGGT GATTTGAGG 3000
ATTTATTTAG TGGATGGACT ACAAGTAATC AGATGTCCAT TCAGGCAGAT AATGCAACTT 3060
TTAAGGGAA CTATCTGCAT ATGTCTGGGG CGAGAGACAT ATATGGAACG ATATTCCCAA 3120
CGTATATATA CCAAAAAATT GATGAATCCA AATTAAAACC GTATACGCGT TATCTAGTCA 3180
```

FIGURE 4 Cry 19Aa POLYNUCLEOTIDE SEQUENCE (continued)

```
GGGGATTTGT GGGAAGTAGT AAAGATCTAG AATTAATGGT AATGCGTTAT GGAAAAGAAA 3240
TTGATACAGT AATGAATGTA CCAAATGACA TACCGTACGT ACCTTCTATG CCGGTCTGTA 3300
ACGAATTATA TGATGGTCAA CAACCGTATC CAAATAGGCA TGTAGGATAT TATAATCCAA 3360
TGCCAGTTTC TCAGCCTTCT TACACATCCG ATACTTGTCA GTGTACGCCC GGCAAAAAAC 3420
ATGTGGTATG TCATGATTCT CATCAATTCA AGTTTCATAT TGATACGGGG GAAGTAGATT 3480
ACAATACAAA TCTAGGAATT TGGGTGTTGT TTAAAATCTC TTCACCCGAT GGCTACGCGA 3540
CATTAGATAA TTTAGAAGTA ATTGAAGAGG GACCAGTAAG AGGCGAAGCA GTGACACATG 3600
TAAAACAAAA GGAAAAGAAA TGGAATCAGC AAATGGAGAA AAAGCGCATG GAAACAAAGC 3660
GAGTCTATGA CCGAGCAAAA CAGGCGGTAG ATGCATTATT TACAGGAGAA GAGTTAAACT 3720
ATGATGTTAC ATTGTCACAC ATTAAGAACG CCGATGATTT GGTACAGTCG ATTCCATATG 3780
TACACAATGA GTGGTTACCG GATTTTCCAG GCATGAACTA TGATATATAC CAAGAGTTAA 3840
ACGCGCGTAT CATGCAAGCA CGCTATTTAT ACGATGCACG AAATGTCATA ACAAATGGGG 3900
ATTTTGCACA AGGATTACAA GGGTGGCATG CGGAAGGAAA AGTAGAAGTA CAGCAAATGA 3960
ACGGAACGTC TGTATTAGTC TTATCCAATT GGAGCTCTGG AGTATCTCAA AACCTTCATG 4020
TCCAACATCC ACATGGATAT CTGTTACGTG TGAGTGCGAA AAAAGAAGGG TCTGGGAAAG 4080
GCTATGTAAC GAGGATGAGT TGTAATGGTA AGCAGGAAAC ACTTACGTTT ACGTCCTGTG 4140
ACGGAGGATA TATGACAAAA ACGGTAGAGG TATTCCCAGA AAGTGATCGT GTACGAATTG 4200
AAATTGGGGA TATGACAAAA ACGGTAGAGG TCGTTTTATA TTGAAAGCAT CGAATTGATT TGTATGAACG 4260
GATATACTAG GACCGAAGGT CAATAATAAC CAGAATATGA GTAATATGTA TGATCAAAGT TATAGTGGGA 4320
ATTATAGTCA GAATACTAGC GATATGTATG ATCAAGGAGG TTCTGTTGCA AAGTTTGAAA 4380
AAGAATAGAA T     4391
```

Figure 6(a)

```
       Loop1
Cry4Aa363   WLDSLNFYEK AQTTPNNFFT SHYNMFHYTL DNISQKSSVF GNHNVTDKLK
Cry4Ba320   WLKRVDFWTN TIYQDLRFLS ANKIGFSYTN SSAMQESGIY GSSGFGSNLT
            **  .*.    *   **    * ....*       *

--Loop2--
Cry4Aa413   SLGLATNIYI FL-LNVISLD NKYLNDYNNI SKMDFFITNG TRL-LEKELT
Cry4Ba370   HQIQL--NSN VYKTSITDTS SPSNRV---- TKMDFYKIDG TLASYN----
             .   .  *.  .*  *  .          *     ***   *

Cry4Aa461   AGSGQITYDV NKNIFGLPIL KRRENQGNPT LFPTYDNYSH ILSFIKSLSI
Cry4Ba410   SNITPTPEGL RTTFGFSTN  ENTPNQ---- ---PTVNDYTH ILSYIKTDVI
             .  .  .    * .* ****.**.       ****.       *** **. .*

Loop3
Cry4Aa511   PATYKTQVYT FAWTHSSVDP KNTIYTHLTT QIPAVKANSL GTASKVVQGP
Cry4Ba454   DY--NSNRVS FAWTHKIVDP NNQIYTDAIT QVPAVKSNFL NATAKVIKGP
             .   . ..  ***** .** .. *** . * *.*****. *  *:**. **
```

Figure 6(b)

```
                                                                Loop 1
Cry4Ba  303  S-IAALEAAAL TRDVHLFTWL KRVDFWTNTI YQDLRFLSAN KIGFSYTNSS
Cry19Aa 325  FSFEKAESLY TRAPHLFTWL KGFRFVTNSI -SYWTFLSGG QNKYSYTNNS --Loop 2--
Cry4Ba  352  AMQESGIYGS S-GFGSNL-T HQIQLNSNVY KTSITDTSS- ----PSNRVT
Cry19Aa 374  SINEGSFRGQ DTDYGGTSST INIPSNSYVY NLWTENYEYI YPWGDPVNIT
```

Competition Assay using *An. quadrimaculatus* BBMV ized prototoxin, proteolytic processing of the prototoxin by midgut proteases to yield a Cry toxin, binding of the processed Cry toxin to midgut receptors, and insertion of the Cry toxin into the apical membrane to create ion channels or pores. The introduction of channels or pores permits the free flow of fluids into the cells, which eventually leads to bursting of the cells and death of the insect.
INSECTICIDAL CRY4BA PROTEINS WITH ENHANCED TOXICITY

PRIORITY CLAIM

This application claims priority to US Provisional Patent Application 60/498,826, filed Aug. 29, 2003, which is incorporated herein by reference, in its entirety.

STATEMENT ON FEDERALLY FUNDED RESEARCH

The present invention was made with support from National Institutes of Health Grant NO. RO1 AI29092. The United States Government has certain rights in the invention.

FIELD OF THE INVENTION

The present invention relates to modified *Bacillus thuringiensis* insecticidal crystal proteins with enhanced toxicity against a variety of insect genera. More particularly, the invention relates to modified crystal proteins Cry4Ba and Cry19Aa that have enhanced toxicity against mosquitos and lepidoptera. The invention also relates generally to modified Cry4Ba and Cry19Aa polypeptides, and insecticidal compositions comprising one or more of these polypeptides. The invention also relates generally to isolated nucleic acids that encode modified Cry4Ba and Cry19Aa polypeptides having enhanced toxicity against target insects.

BACKGROUND OF THE INVENTION

Malaria, dengue, and West Nile Fever are currently the most mentioned mosquito-borne diseases affecting humans. An estimated 1.2 billion clinical attacks of malaria occur each year in Africa. According to the latest consensus of scientists and health workers, malaria kills up to 2.7 million persons each year. Ninety percent of these cases and deaths occur in Africa, and a large portion of them involve children under the age of five. Approximately 1.7 million African children die yearly due to malaria-linked illnesses. Meanwhile, it is estimated that about 50-100 million dengue fever cases occur annually, including a few hundred thousand cases of the life-threatening form (dengue hemorrhagic fever).

Transmission of mosquito-borne diseases occurs through inoculation whereby infected blood-feeding mosquitoes bite target organisms, such as humans, and transfer the disease pathogen into the target's bloodstream. A variety of mosquito species, including *Aedes aegypti* (dengue, yellow fever), *Anopheles quadrimaculatus* (malaria), *Culex quinquefasciatus* (West Nile virus) and *Cx. pipiens* (West Nile virus) are vectors of blood-borne pathogens that cause disease in humans and other mammals. For example, dengue, yellow fever are transmitted by *Aedes aegypti*, malaria is transmitted by *Anopheles quadrimaculatus* (malaria), and West Nile virus is transmitted by *Cx. quinquefasciatus* and *Cx. Pipiens*.

Control of insect pests such as mosquitoes is achieved using a variety insecticidal materials. Some insecticidal materials include proteins that are made by the bacterium *Bacillus thuringiensis*. *Bacillus thuringiensis* (Bt) is a ubiquitous facultative anaerobic, Gram-positive, motile, spore-forming bacterium that produces proteins that accumulate as crystals within the bacterial cell. These insecticidal crystal proteins are toxic to a number of insects, mainly insects in the orders Coleoptera, Diptera, and Lepidoptera. Pesticidal formulations containing Bt crystal proteins have been used extensively in commercial agriculture, forest management, and mosquito control. Bt is a member of the *B. cereus* (Bc) group that includes *B. cereus, B. anthracis,* and *B. mycoides*. Bt has been classified according to its cellular, cultural, biochemical, and genetic characteristics. However, serotypic and specific biochemical characteristics have been found to be inconsistent. Bt can only be differentiated from Bc by the production of one or more of the insecticidal crystalline (Cry) proteins that are toxic to invertebrates.

Bt is accepted as a source of environment-friendly biopesticide. Farmers have applied Bt as an insecticidal spray for control of lepidopteran and coleopteran pests for more than 30 years. The United States Environmental Protection Agency has considered Bt sprays to be so safe that it has exempted them from the requirement of a tolerance (a standard for a maximum permissible residue limit on food).

The mechanism of action of the Bt crystal proteins involves solubilization of the crystal in the insect midgut to yield a solubilized prototoxin, proteolytic processing of the prototoxin by midgut proteases to yield a Cry toxin, binding of the processed Cry toxin to midgut receptors, and insertion of the Cry toxin into the apical membrane to create ion channels or pores. The introduction of channels or pores permits the free flow of fluids into the cells, which eventually leads to bursting of the cells and death of the insect.

Of the many known Cry proteins, most have limited range of toxicity against insects, and are often quite specific for only one or a few insect genera. Importantly, the known Cry proteins exhibit only limited toxicity to the range of mosquito genera that are responsible for disease in humans and other mammals. Accordingly, it would be desirable to provide Bt Cry proteins that have enhanced toxicity to insects, and more particularly to one or more genera of mosquitoes that are associated with human disease.

SUMMARY OF THE INVENTION

The present invention relates generally to modified Bt insecticidal crystal proteins, also referred to as mutant toxins, with enhanced toxicity against a variety of insect genera, particularly mosquitos.

The invention relates to modified Bt Cry4Ba proteins that have toxicity-enhancing sequence modifications at one or more positions within the amino acid sequence of the protein. These modified Cry4Ba proteins have new or increased toxicity when ingested by insects of one or more genera. More specifically, the modified Cry4Ba proteins have a greater spectrum of activity against different, or a selective, genera of mosquitoes. Mutant forms of Cry4Ba according to the present invention have toxic activity against *Culex* mosquitoes, in addition to the toxic activity against *Anopheles* and *Aedes* mosquitoes associated with the wild-type form of Cry4Ba. In some embodiments, these modified Cry4Ba proteins also have toxicity against lepidoptera. According to these embodiments, the toxicity-enhancing modifications are located in the putative loop 3 of domain II of Cry4Ba. In some embodiments, mutant forms of Cry4Ba have toxic activity against *Culex*, as well as enhanced toxicity against *Anopheles* and *Aedes* as compared to wild-type Cry4Ba According to these embodiments, the toxicity-enhancing modifications are located in the putative loop 3 of domain II, and in domain III of Cry4Ba.

The invention also relates to modified Cry19Aa proteins that have toxicity-enhancing sequence modifications at one or more positions within the amino acid sequence of the protein. These modified Cry19Aa proteins have new or increased toxicity when ingested by insects of one or more genera. More specifically, the modified Cry19Aa proteins have a greater spectrum of activity against different, or a selective, genera of mosquitoes, and other insects Mutant forms of Cry19Aa according to the present invention have toxic activity against *Aedes* mosquitoes, in addition to the toxic activity against *Anopheles* and *Culex* mosquitoes associated with the wild-type form of Cry19Aa. The toxicity-enhancing modifications to Cry19Aa are located in putative loops 1 and 2 of domain II of the protein.

The invention also relates to polynucleotides that encode modified Cry4Ba proteins that have toxicity-enhancing amino acid modifications at one or more positions in the protein. In a preferred embodiment, the polynucleotide modifications are located in the portion of the sequence that encodes the putative loop 3 of domain II of the Cry4Ba protein. In another preferred embodiment, the polynucleotide modifications are located in the region that encodes the putative loop 3 of domain II, and in domain III of the Cry4Ba protein.

The invention also relates to polynucleotides that encode modified Cry19Aa proteins that have toxicity-enhancing amino acid sequence modifications at one or more positions in the protein. In a preferred embodiment, the polynucleotide modifications are located in the region that encodes putative loops 1 and 2 of domain II of the Cry19Aa protein.

The invention also relates to mutagenic primers for preparing the polynucleotides that encode the modified Cry4Ba and Cry19Aa proteins.

The invention also relates generally to vectors comprising the polynucleotides that encode the modified Cry4Ba and Cry19Aa proteins.

The invention also relates to host organisms, also referred to herein as recombinant organisms, which are transfected with the vectors comprising the polynucleotides that encode either the modified Cry4Ba or Cry19Aa proteins. The host organisms express the modified either the modified Cry4Ba or Cry19Aa proteins.

The invention also relates to methods for reducing or eliminating populations of insects that are vectors of disease, particularly mosquitoes, by delivering into the habitat of target insects one or more modified Cry4Ba and Cry19Aa proteins as insecticidal agents. In some embodiments, the modified proteins are applied in an appropriate formulation to plants and other surfaces and areas within the target insect's habitat for the ingestion by target insects. In other embodiments, host organisms transfected with polynucleotide vectors of the present invention and expressing the mutant toxins are delivered to the habitat of the target organism for ingestion by target insects.

The invention also relates to insecticidal compositions comprising mutant toxins with a new or broadened insecticidal spectrum. The insecticidal composition may be formulated in an agriculturally acceptable carrier, diluent and/or excipient. The modified Cry4Ba or Cry19Aa proteins disclosed herein and other insecticidal agents may be used alone or in combination; that is, one or more insecticidal agents, including one or more of the mutant toxins of the present invention, are used to control insect pests. The active ingredients of the insecticidal composition may be formulated together or separately as a wettable powder, emulsifiable concentrate, aqueous or liquid flowable, suspension concentrate or any one of the conventional formulations used for insect control agents and tank mixed in the field with water or other inexpensive liquid for application as a liquid spray mixture. The separately formulated compositions may be applied simultaneously or sequentially. In alternative embodiments, insecticidal compositions may comprise modified organisms that express one or more mutant toxins that may be ingested by target insects. According to such embodiments, the modified organisms are delivered in appropriate carriers or excipients. Modified organisms may be plants, algae, or microbes.

The invention also relates to methods for providing Bt toxins having enhanced toxicity to insects, more particularly mosquitoes. The invention involves producing engineered amino acid substitutions in Bt delta-endotoxins. In particular, the invention involves introducing amino acid substitutions into Bt delta-endotoxins having little or no activity against one ore more target insects to create greater activity against said one or more target insects. More specifically, the invention involves performing a computational structure modeling and structure-based comparison between two delta-endotoxins to identify appropriate sites for introducing modifications to introduce or enhance activity against one or more target insects. In a preferred embodiment, the invention relates to a method of introducing mutations into the structure of one of the Cry19Aa and Cry4Ba toxins by targeting for mutation exposed loop residues in the structural domains of these proteins that are associated with specific insect toxicities. In one embodiment, the method relates to introducing mutations in the exposed loop residues in loop 3 of domain II of the Cry4Ba crystal toxin so as to confer *Culex* toxicity. In another embodiment, the method relates to introducing mutations in the exposed loop residues in loop 3 of domain II, and domain III of the Cry4Ba crystal toxin so as to confer *Culex* toxicity and enhance *Aedes* and *Anopheles* toxicity. In another embodiment, the method relates to introducing mutations in the exposed loop residues of loops 1 and 2 of domain II of the Cry19Aa crystal toxin so as to confer *Aedes* toxicity.

Additional features and advantages of the invention will be set forth in part in the description that follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, that are incorporated in and constitute a part of this specification, illustrate several embodiments of the invention, and together with the description, serve to explain the principles of the invention.

BRIEF DESCRIPTION OF THE FIGURES

The present invention may be more readily understood by reference to the following drawings wherein:

FIG. 1: Amino acid sequence (SEQ ID NO: 1) of Cry4Ba corresponding to Genbank Accession Number X07423.1.

FIG. 2: Polynucleotide sequence (SEQ ID NO: 2) of Cry4Ba corresponding to Genbank Accession Number X07423.1.

FIG. 3: Amino acid sequence (SEQ ID NO: 3) of Cry19Aa corresponding to Genbank Accession Number Y07603.1.

FIG. 4: Polynucleotide sequence (SEQ ID NO: 4) of Cry19Aa corresponding to Genbank Accession Number Y07603.1.

FIG. 6: (a) Sequence alignments based on the model structures Cry4Aa (SEQ ID NO: 5) with Cry4Ba (SEQ ID NO: 6)

using Swiss-Pdb Viewer. Loops positions are indicated on top of the sequences. (b) Sequence alignments based on the model structures Cry4Ba (SEQ ID NO: ) with Cry19Aa (SEQ ID NO: 8) using Swiss-Pdb Viewer. Loops positions are indicated on top of the sequences. The (*) symbol represents identity, while (.) represents similarity.

Figure 7:
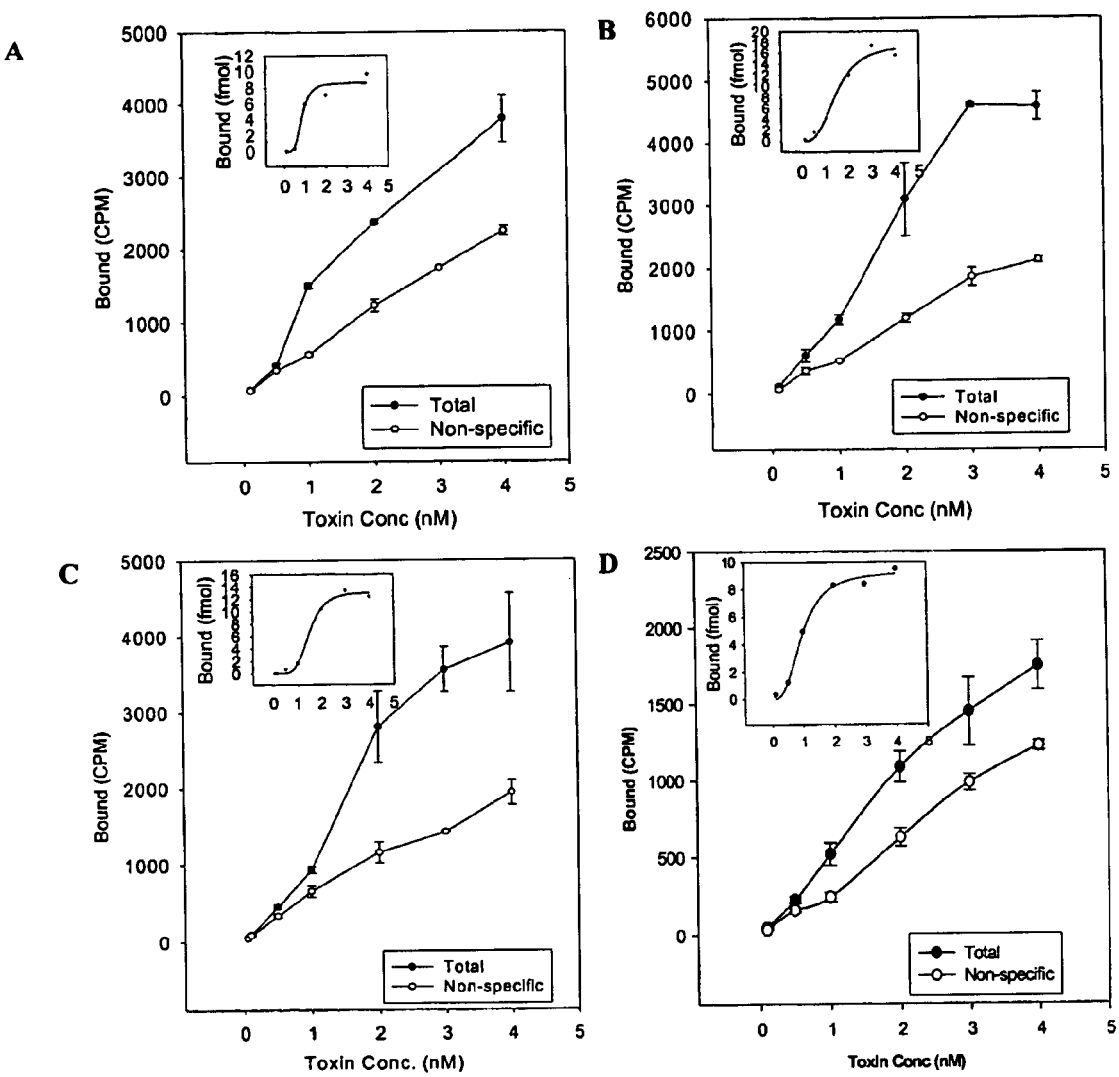

FIG. 7: Saturation binding assay of $^{125}$I-4BRA to (A) *Ae. aegypti* BBMV; (B) *An. quadrimaculatus* BBMV; (C) *Cx. quinquefasciatus* BBMV. (D) Saturation binding assay of $^{125}$I-4BL3PAT to *Cx. quinquefasciatus* BBMV. The inset graphs show specific binding obtained by subtracting non-specific binding from total binding. The sigmoidal shapes of the specific binding curves suggest positive cooperative binding of the toxin to the BBMV. Data shown were average of three experiments.

Figure 8:
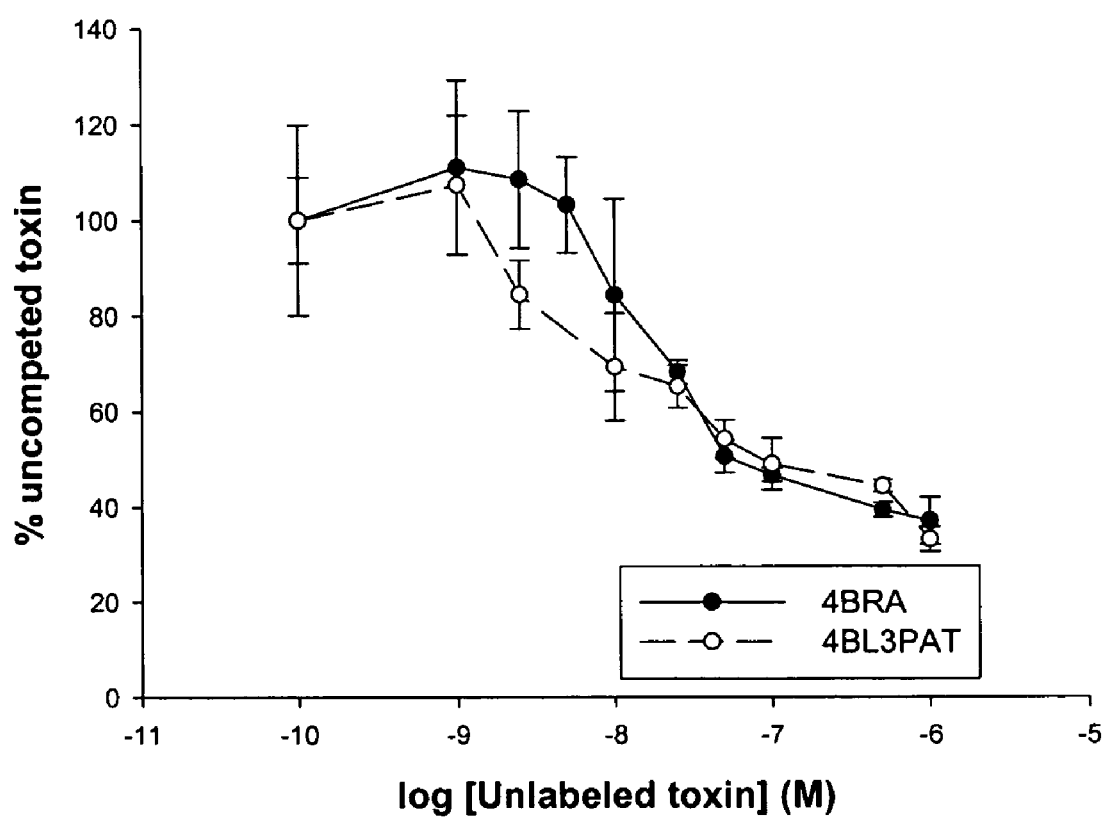

FIG. 8: Homologous and heterologous competition binding assays. $^{125}$I-labeled 4BRA was incubated with *Cx. quinquefasciatus* BBMV with increasing amount of unlabeled toxin. Data shown are mean of three binding experiments.

Figure 9:
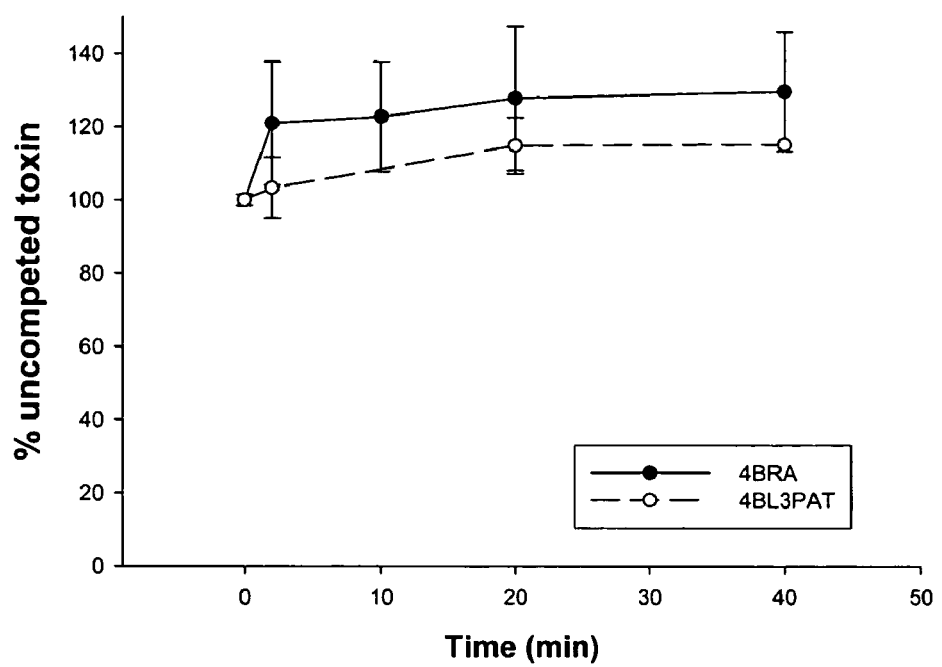

FIG. 9: Irreversible binding assays. $^{125}$I labeled 4BRA or 4BL3PAT was incubated with *Cx. quinquefasciatus* BBMV for 1 hour at room temperature. Then, bound toxin was chased away with 1000 nM excess of unlabeled toxin with increasing incubation time. Data shown are mean of three binding experiments.

Figure 10:
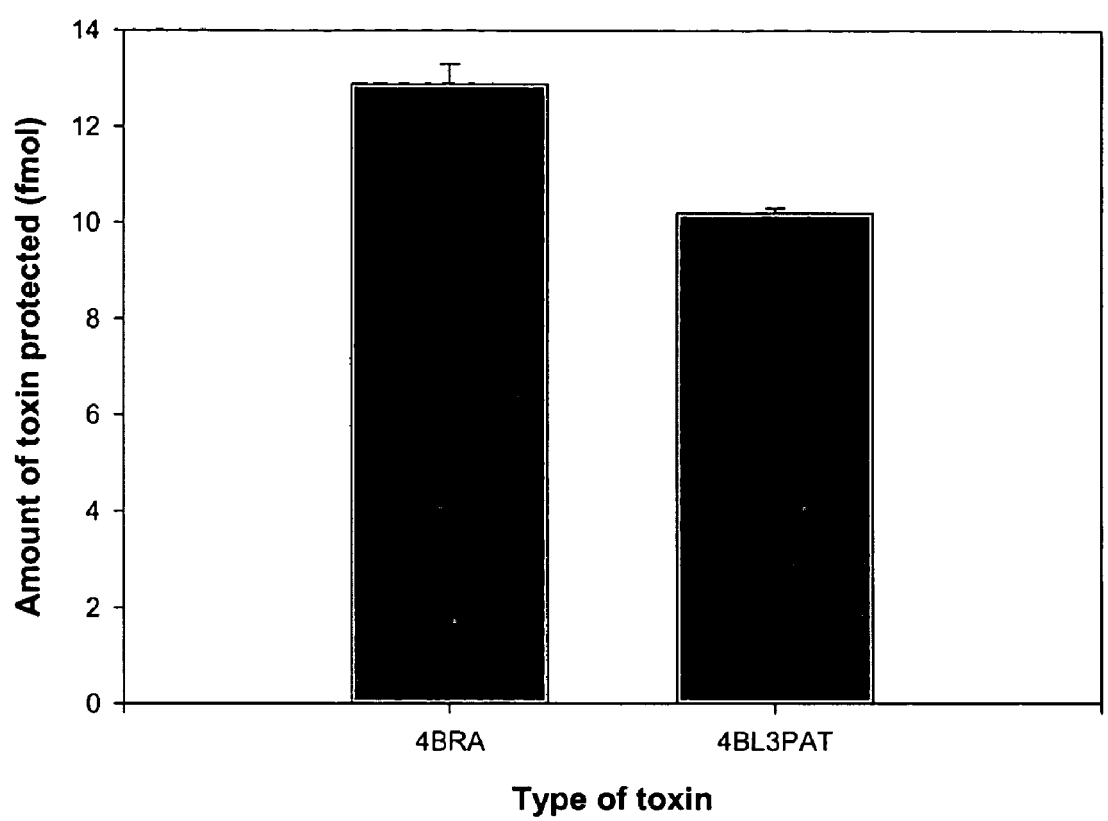

FIG. 10: Proteinase K protection assay of 4BRA and 4BL3PAT. $^{125}$I-labeled toxin was incubated with *Cx. quinquefasciatus* BBMV for 1 h. Free and non-inserted toxin was digested with proteinase K and the reaction was stopped with pefabloc. BBMV-protected toxin was separated by centrifugation and the counts measured.

Figure 11:
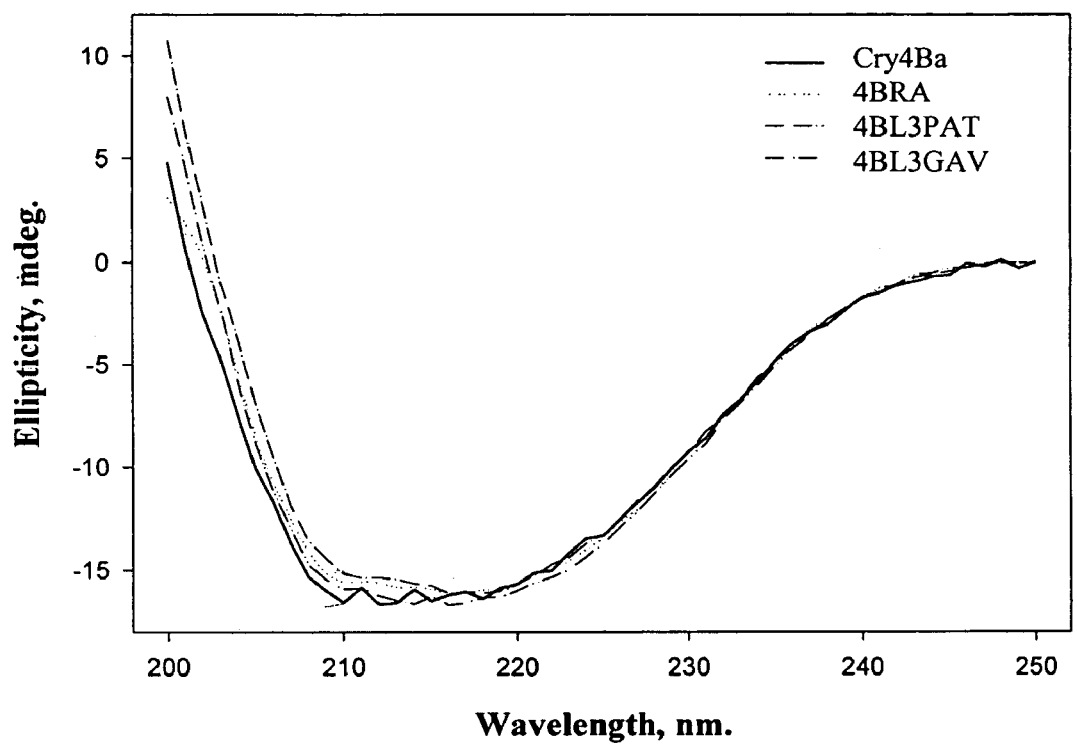

FIG. 11: CD spectrum of purified toxins of Cry4Ba and its mutants.

Figure 12:
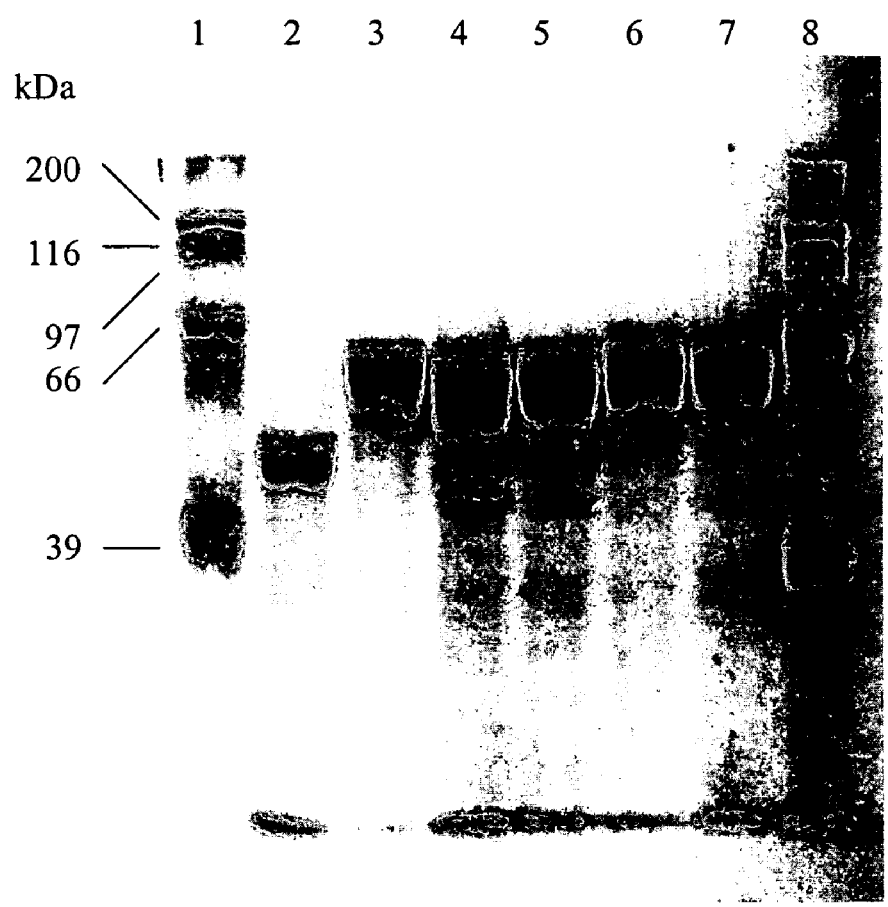

FIG. 12: SDS PAGE of HPLC-purified trypsin activated toxins. Lanes: 1 & 8, Marker; 2, Cry4Ba; 3, 4BRA; 4, 4BL1QTT; 5, 4BL3PAT; 6, 4BL3GAV; 7, 4BL3AAT.

Figure 13:
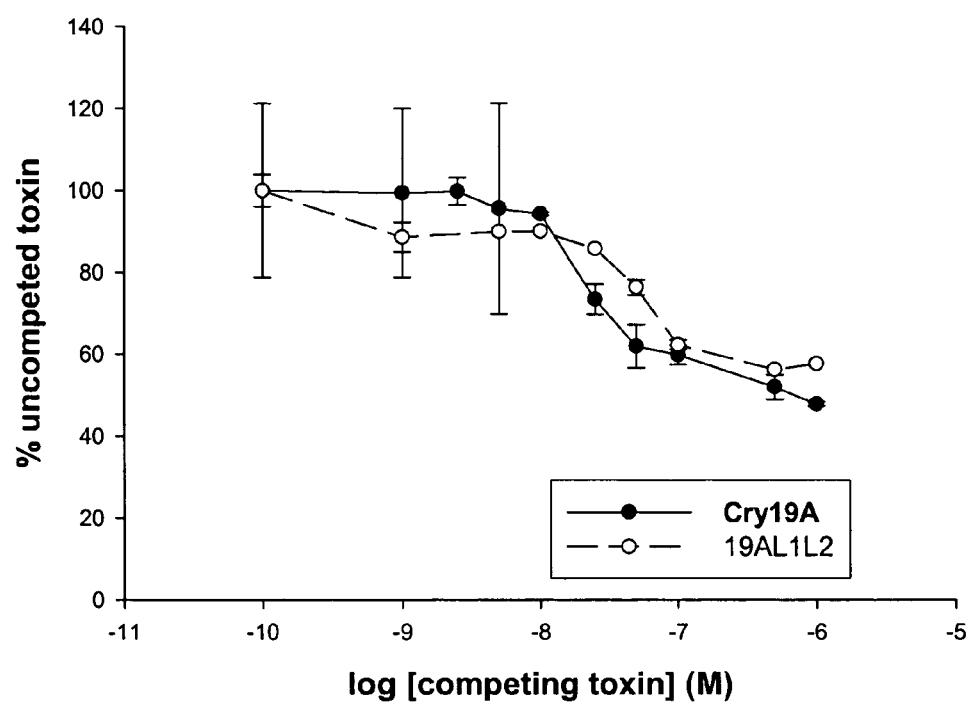

FIG. 13: Homologous and heterologous competition binding assays. $^{125}$I-labeled Cry19Aa was incubated with *Ae. aegypti* BBMV with increasing amount of unlabeled toxin. Data shown are mean of three binding experiments.

Figure 14:
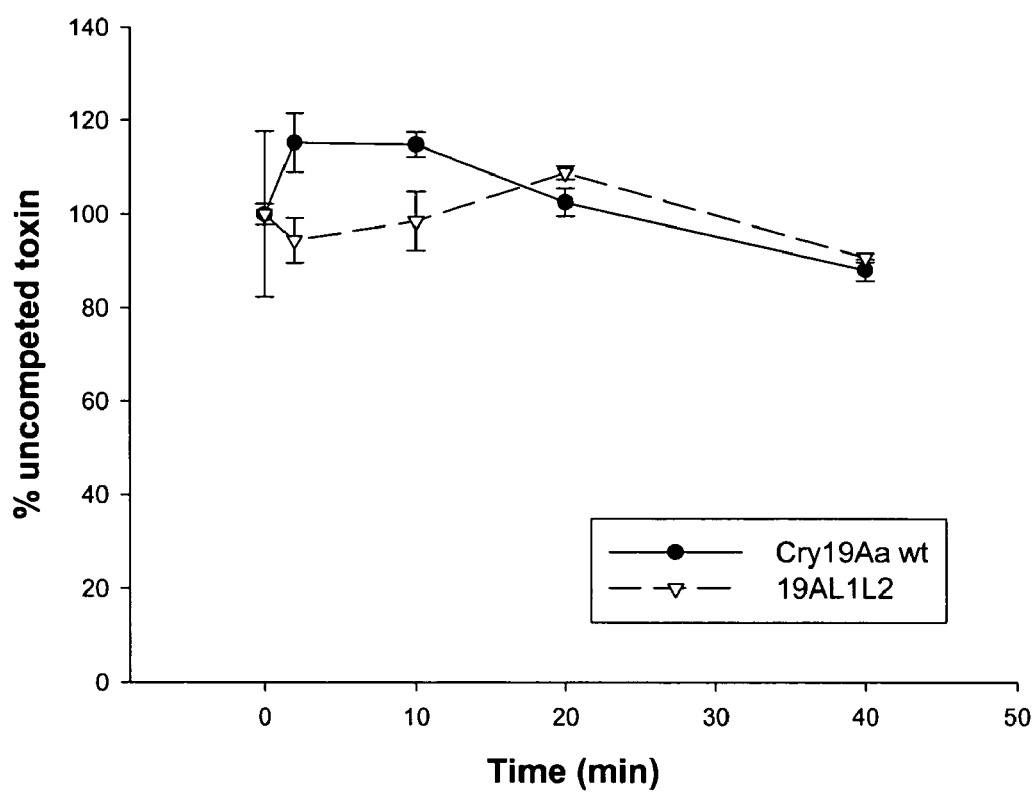

FIG. 14: Irreversible binding assays. $^{125}$I labeled Cry19Aa or 19AL1L2 was incubated with *Ae. aegypti* BBMV for 1 hour at room temperature. Then, bound toxin was chased away with 1000 nM excess of unlabeled toxin with increasing incubation time. Data shown are mean of three binding experiments.

Figure 15:
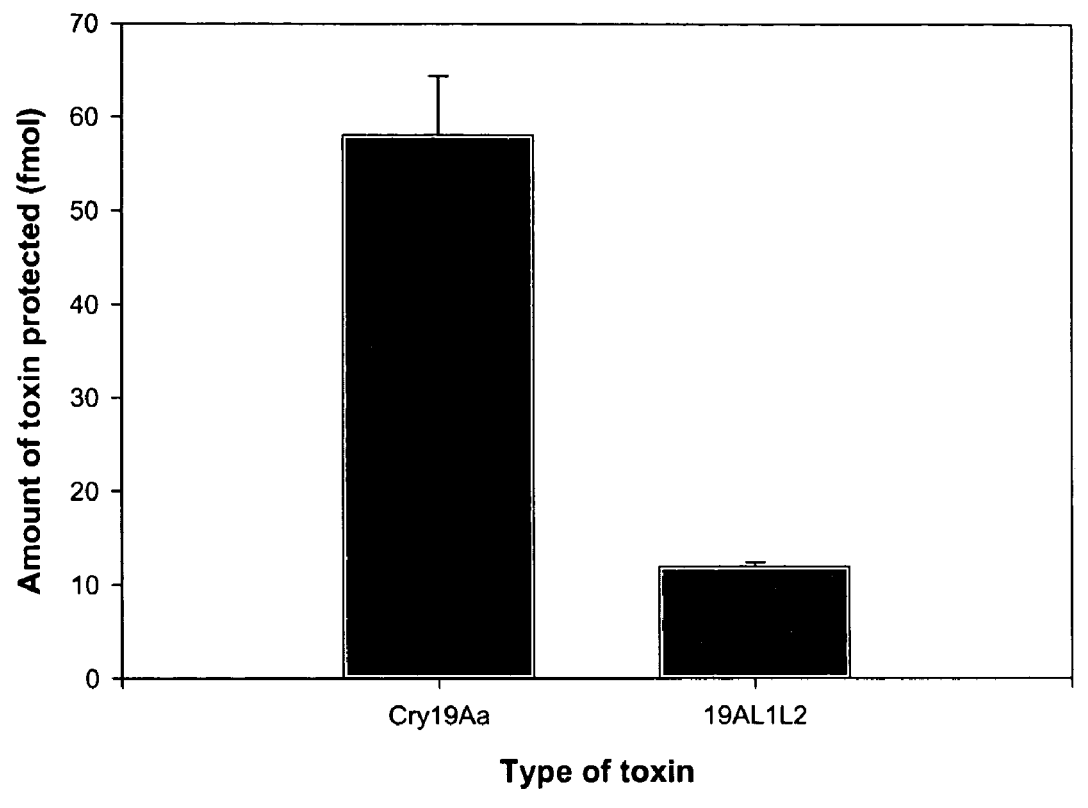

FIG. 15: Proteinase K protection assay. $^{125}$I-labeled toxin was incubated with *Ae. aegypti* BBMV for 1 hour. Free and non-inserted toxin was digested with proteinase K and the reaction was stopped by Pefabloc sc. BBMV-protected toxin was separated by centrifugation and the counts measured.

Figure 16:
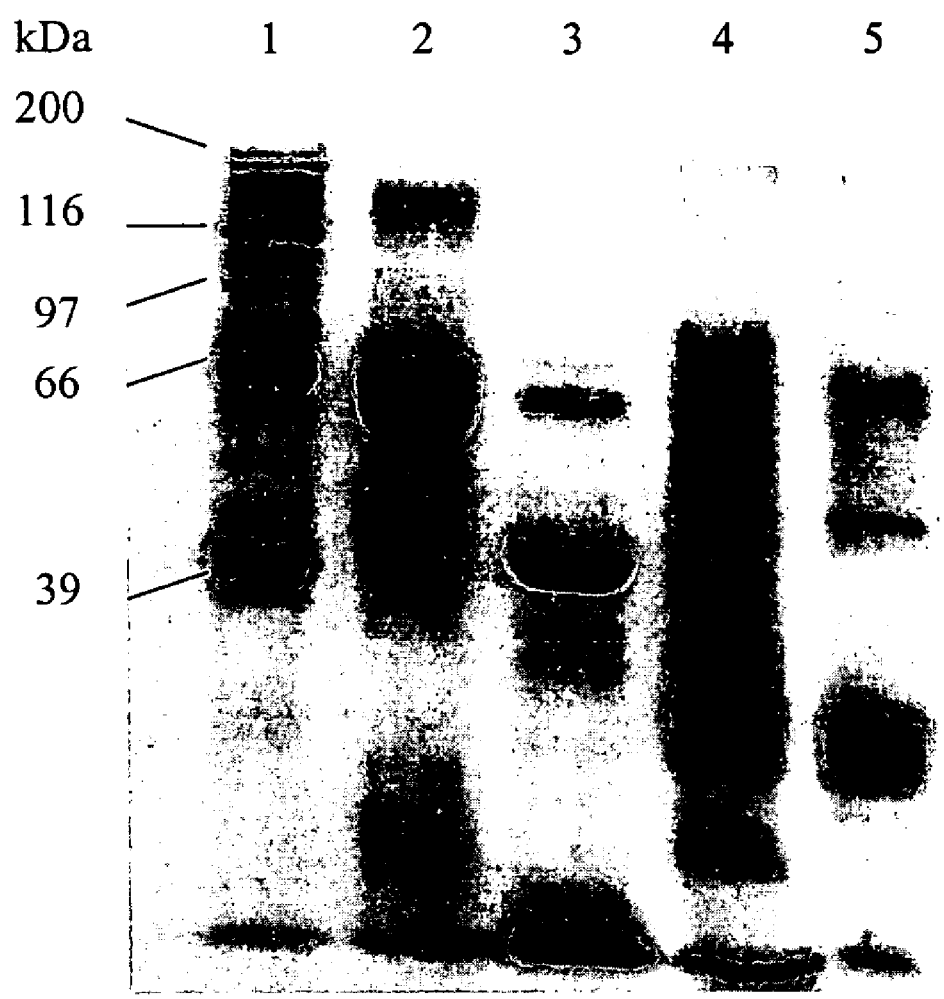

FIG. 16: SDS PAGE of HPLC-gel filtration purified of non-trypsin activated and trypsin activated toxins. Lanes: 1, Marker; 2, Cry19Aa non-trypsin activated; 3, 19AL1L2 non-trypsin activated; 4, Cry19Aa trypsin activated; 5, 19AL1L2 trypsin activated.

Figure 17:
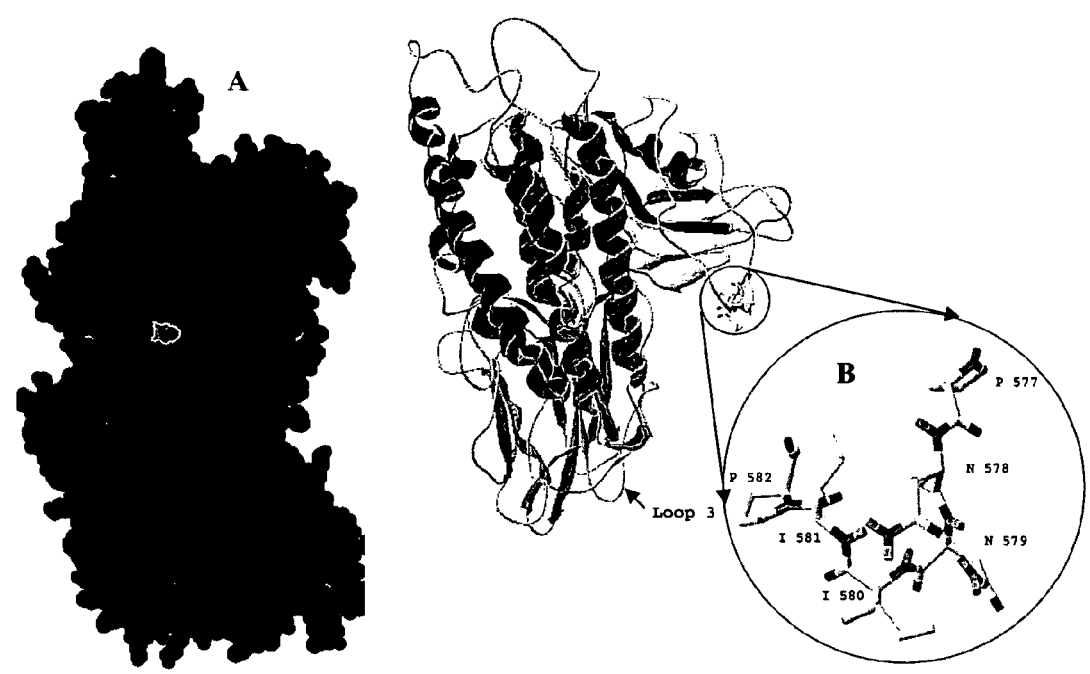

FIG. 17. (A) A space-fill representation of a model complex of 4BL3PAT (blue) and CPM1 (red) showing the position of residue I580 (yellow) obtained from protein docking using GRAMM. (B) A blow-up view of the putative domain III loop structure based on the model structure of 4BL3PAT.

FIG. 18. Homologous and heterologous competition binding assays. $^{125}$I-labeled 4BRA was incubated with *An. quadrimaculatus* BBMV with increasing amount of unlabeled toxin. The mutants (N578A, I581A, I580F, and I581F) are based on the 4BL3PAT construct. Data shown are mean of three binding experiments.

DETAILED DESCRIPTION OF THE INVENTION

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to that this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The disclosure of all patents, patent applications (and any patents that issue thereon, as well as any corresponding published foreign patent applications), GenBank and other accession numbers and associated data, and publications mentioned throughout this description are hereby incorporated by reference herein. It is expressly not admitted, however, that any of the documents incorporated by reference herein teach or disclose the present invention.

The present invention may be understood more readily by reference to the following detailed description of the preferred embodiments of the invention and the Examples included herein. However, before the present methods, compounds and compositions are disclosed and described, it is to be understood that this invention is not limited to specific methods, specific nucleic acids, specific polypeptides, specific cell types, specific host cells or specific conditions, etc., as such may, of course, vary, and the numerous modifications and variations therein will be apparent to those skilled in the art. It is also to be understood that the terminology used herein is for the purpose of describing specific embodiments only and is not intended to be limiting.

The methods for protein-protein comparison and structural analysis disclosed herein is apparent to those skilled in the art. For example, such techniques are disclosed in and its contents are herein incorporated by reference: Guex, N. and Peitsch, M. C. SWISS-MODEL and the Swiss-Pdb Viewer: An environment for comparative protein modeling. *Electrophoresis*, Vol. 18, pp. 2714-2723 (1997). Recombinant DNA methods are well known in the art. See, for example, Molecular Cloning: A Laboratory Manual, Third Edition (2001) Cold Spring Harbor Laboratory Press, Cold Spring Harbor, N.Y.).

Definitions The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant molecular species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 50% pure, more preferably at least 85% pure, and most preferably at least 99% pure.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19: 5081; Ohtsuka et al. (1985) J. Biol. Chem. 260: 2605-2608; Cassol et al. (1992); Rossolini et al. (1994) Mol. Cell. Probes 8: 91-98). The term nucleic acid is used interchangeably with gene, cDNA, and mRNA encoded by a gene.

The term "gene" is used broadly to refer to any region or segment of DNA associated with a biological function. Thus, genes include coding sequence, and may further include regulatory regions or segments required for their expression. Genes may also include non-expressed DNA segments that, for example, form recognition sequences for other proteins. Genes can be obtained from a variety of sources, including cloning from a source of interest or synthesizing from known or predicted sequence information, and may include sequences encoding desired parameters.

The terms "naturally-occurring" and "wild-type" are used to describe something that can be found in nature as distinct from being artificially produced by man. For example, a polypeptide or polynucleotide sequence that is present in an organism (including viruses) that can be isolated from a source in nature and that has not been intentionally modified by man in the laboratory is naturally-occurring. In particular, "wild-type" is used herein to refer to the naturally-occurring or native forms of Bt Cry proteins and their encoding nucleic acid sequences.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated.

The sequence comparison algorithm then calculates the percent sequence identity for the test sequence(s) relative to the reference sequence, based on the designated program parameters. Three main programs were used in connection with the instant invention: i) An internet-based CLUSTAL W version; ii) SWISS-MODEL; and iii) Swiss-Pdb Viewer Version 3.7b2. All of these programs are freely accessible via the worldwide web and are quite simple to operate. CLUSTAL W was used to align the protein sequence of the target protein with the template of known tertiary structure. Models were constructed using the "Optimize (project) mode" in SWISS-MODEL, in conjunction with Swiss-Pdb Viewer. The sequence of the target protein was aligned with the template sequence in Swiss-Pdb Viewer according to the alignment produced by CLUSTAL W earlier. Unaligned residues at the N and C terminal of the target protein were removed prior to submitting the project to the SWISS-MODEL site. The template file used was chosen from either the known tertiary structures or from the models that were constructed with SWISS-MODEL.

In the context of the present invention, "substantially similar" means a protein having an amino acid sequence that is at least 75% similar to the sequence of a wild-type protein, wherein said substantially similar protein has an toxicity enhancing modification according to the invention, and wherein the substantially similar protein optionally comprises other modifications that may or may not be toxicity enhancing. It is preferred that the degree of similarity is at least 85%, more preferred that the degree of similarity is at least 90%, and still more preferred that the degree of similarity is at least 95% or more. In the context of the present invention, two amino acid sequences with at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, similarity to each other have at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical or conservatively replaced amino acid residues in a like position when aligned optimally allowing for up to 6 gaps, with the proviso that, with respect to the gaps, a total not more than 15 amino acid residues are affected. The substantially similar protein may have 100% sequence identity with a modified protein according to the invention, however, such substantially similar protein and such protein according to the present invention will share less than 100% sequence identity with the wild-type form of the modified Cry protein and the substantially similar protein. For the purpose of the present invention, conservative replacements may be made between amino acids within the following groups: (i) Serine and Threonine; (ii) Glutamic acid and Aspartic acid; (iii) Arginine and Lysine; (iv) Asparagine and Glutamine; (v) Isoleucine, Leucine, Valine, and Methionine; (vi) Phenylalanine, Tyrosine, and Tryptophan; and (vii) Alanine and Glycine.

Substantially similar polynucleotides hybridize to the same reference sequence under stringent conditions. A reference sequence is a sequence that has reverse complementarity to a sequence of interest. The phrase "hybridizing specifically to," refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization conditions" and "stringent hybridization wash conditions" in the context of nucleic acid hybridization experiments such as Southern and northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays," Elsevier, N.Y. Generally, highly stringent hybridization and wash conditions are selected to be 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids that have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for 15 minutes. An example of stringent wash conditions is a 0.2×SSC wash at 65° C. for 15 minutes (see, Sambrook, infra., for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., 10 to 50 nucleotides), stringent conditions typically involve salt concentrations of less than 1.0 M Na ion, typically 0.01 to 1.0 M Na ion concentration (or other salts) at pH 7.0 to 8.3, and the temperature is typically at least 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially similar if the polypeptides that they encode are substantially similar. This occurs, e.g., when a copy of a nucleic acid is created using the maximum codon degeneracy permitted by the genetic code.

"Conservative modifications" are those modifications to a particular polynucleotide sequence that result in a modified polynucleotide that encodes a mutant polypeptide having an amino acid sequence that is nearly identical to the sequence of the wild-type, or naturally-occurring form of the polypeptide. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one form of "conservatively modified variations." Every polynucleotide sequence described herein that encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid that encodes a polypeptide is implicit in each described sequence.

Furthermore, one of skill will recognize that individual substitutions, deletions or additions that alter, add or delete a single amino acid or a small percentage of amino acids (typically less than 5%, more typically less than 1%) in an encoded sequence are "conservative modifications" where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I), Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton (1984) Proteins, W. H. Freeman and Company. In addition, individual substitutions, deletions or additions that alter, add or delete a single amino acid or a small percentage of amino acids in an encoded sequence are also "conservative modifications."

An "exogenous DNA segment," "heterologous sequence" or a "heterologous nucleic acid" ("heterologous polynucleotides") is one that originates from a source that is different from the particular host cell into that the heterologous polynucleotides are being inserted, or, if from the same source, is modified from its original form. Thus, a heterologous gene in a host cell includes a gene that is endogenous to the particular host cell, but has been modified. Modification of a heterologous sequence in the applications described herein typically occurs through the use of site-directed mutagenesis, although other methods known in the art may be used in accordance with the embodiments of the present invention. Thus, the terms refer to a DNA segment that is foreign or heterologous to the cell, or homologous to the cell but in a position within the host cell nucleic acid in which the element is not ordinarily found, or has a sequence that is different from the native form of the polynucleotide. Exogenous DNA segments are expressed to yield exogenous polypeptides.

"Exposed residues" and "exposed loop residues" refers to the amino acid residues in a Cry protein that are determined by three dimensional analysis to be exposed, that is, not located in interior portions of a folded molecule. Exposed residues may be associated with or, together with other residues, form binding sites for ligands or active sites for catalysis. Exposed residues may extend in three dimensional space beyond the extension of other adjacent or distant residues in the folded protein.

Toxicity enhancing modifications to Cry4Ba and Cry19Aa: The present invention concerns modified Cry proteins and polynucleotides encoding the same, particularly involving toxicity enhancing modifications to Cry4Ba and Cry19Aa proteins. Modifications are made relative to the polypeptide sequences of wild-type forms of the Cry4Ba and Cry19Aa proteins, and are in the form of substitutions, deletions, and insertions, and combinations of these. The modified Cry proteins have amino acid sequences that are substantially similar to the naturally-occurring forms of the proteins, such as the Cry4Ba and Cry19Aa polypeptides shown in FIGS. 1 and 3. Polynucleotides encoding modified Cry proteins according to the instant invention have nucleic acid sequences that are substantially similar to wild-type nucleotides encoding the naturally-occurring forms of the proteins; for example, polynucleotides encoding the mutant toxins have sequences that are substantially similar to Cry protein genes, such as the genes that encode Cry4Ba and Cry19Aa as shown in FIGS. 2 and 4.

The nucleotide sequence of the Cry4Ba gene is shown in FIG. 2 and in SEQ ID NO: 2, and the corresponding amino acid sequence of the protein encoded by said nucleotide sequence is shown in FIG. 1 and in SEQ ID NO: 1. The sequences provided herein for Cry4Ba correspond to Genbank Accession Number X07423.1, as reported by Chungjatupornchai, et. al., Eur. J. Biochem. 173:9-16 (1988). As shown in FIG. 2, the Cry4Ba gene is 3684 nucleotides in length, and includes a coding sequence from nucleotide positions 157 through 3567. As shown in FIG. 1, the Cry4Ba protoxin has 1136 amino acids, and the protein has an approximate molecular weight of 127764 Da. Cry4Ba toxin has three domains, designated I, II and III. As determined in one structural analysis study, domain I is approx. 277 amino acids in length (approx. positions 1 through 277); domain II is approx. 194 amino acids in length approx. (positions 278 through 470); and domain III is approx. 162 amino acids in length (approx. positions 471 through 633). Loop 3 of domain II is approx. 10 amino acids in length (approx. positions 451 through 461). As determined in a second structural analysis study, domain I is approx. 269 amino acids in length (approx. positions 1 through 269); domain II is approx. 201 amino acids in length approx. (positions 270 through 470); and domain III is approx. 164 amino acids in length (approx. positions 471 through 634). Loop 3 of domain II is approx. 6 amino acids in length (approx. positions 452 through 457). As shown in The wild-type Cry4Ba protein is toxic to Anopheles stephensi and Aedes aegypti, but shows no measurable activity against either and *Culex pipiens* or *Culex quinquefasciatus*.

The nucleotide sequence of the Cry19Aa gene is shown in FIG. 4 and in SEQ ID NO: 4, and the corresponding amino acid sequence of the protein encoded by said nucleotide sequence is shown in FIG. 3 and in SEQ ID NO: 3. The sequences provided herein for Cry19Aa correspond to Genbank Accession Number Y07603.1, as reported by Rosso, et. al., Appl. Environ. Microbiol. 63:4449-4455 (1997). As shown in FIG. 4, the Cry19Aa gene is 4391 nucleotides in length, and includes a coding sequence from nucleotide positions 719 through 2665. As shown in FIG. 3, Cry19Aa protoxin has 648 amino acids, and the protein has an approximate molecular weight of 74742 Da. Cry19Aa toxin has three domains, designated I, II and III. As determined in one structural analysis study, domain I is approx. 298 amino acids in length (approx. positions 1 through 298); domain II is approx. 205 amino acids in length (approx. positions 299 through 504); and domain III is approx. 141 amino acids in length (approx. positions 506 through 647). Loop 1 of domain II is approx. 3 amino acids in length (approx. positions 355 through 355); loop 2 of domain II is approx. 4 amino acids in length (approx. positions 414 through 418); and loop 3 of domain II is approx. 16 amino acids in length (approx. positions 477 through 493). As determined in one structural analysis study, domain I is approx. 299 amino acids in length (approx. positions 1 through 299); domain II is approx. 203 amino acids in length (approx. positions 300 through 502); and domain III is approx. 146 amino acids in length (approx. positions 503 through 648). Loop 1 of domain II is approx. 8 amino acids in length (approx. positions 352 through 359); loop 2 of domain II is approx. 13 amino acids in length (approx. positions 409 through 421); and loop 3 of domain II is approx. 6 amino acids in length (approx. positions 482 through 487). The wild-type Cry19Aa protein is toxic *Anopheles stephensi* and *Culex pipiens,* but shows only low measurable activity against *Aedes aegypti*.

Toxicity enhancing modifications are modifications made in specific regions of the amino acid sequences of Cry proteins, particularly Cry4Ba and Cry19Aa proteins, more particularly in either or both the loop regions in domain II of Cry4Ba and domain II of Cry19Aa, which result in enhancement of toxicity in one or more species within one or more genera of insects. Toxicity enhancing modifications result in proteins having amino acid sequences that are substantially similar to and share less than 100% sequence identity with wild-type forms of the Cry proteins. Toxicity enhancing modifications may be present as the only sequence modifications in a Cry protein, or they may be in addition to other modifications that may or may not alter toxicity. In the case of other modifications that affect toxicity, such other modifications will not nullify the toxicity enhancement of the toxicity enhancement modifications. Combined non-toxicity enhancing and toxicity enhancing modifications may result in proteins that have amino acid sequence identity that share 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, but in all cases less than 100% sequence identity with wild-type forms of the modified Cry proteins. Mutant toxins may also comprise other conservative modifications that do not alter functionality of the protein and do not influence toxicity, and which mutations influence the percent identity between the mutant toxin and the wild-type form of Cry protein.

We disclose here that amino acid modifications in Cry4Ba and Cry19Aa proteins confer new or increased toxicity against one or more genera of insect, particularly genera of mosquito, and more particularly mosquito genera *Anopheles, Aedes,* and *Culex*. In one embodiment, Cry4Ba modified proteins according to the present invention exhibit *Anopheles* and *Aedes* toxicity that is comparable to wild-type forms of the protein, but they also exhibit *Culex* activity that is not observed in naturally-occurring forms of Cry4Ba. In another embodiment, modified Cry4Ba proteins according to the present invention exhibit enhanced *Anopheles* and *Aedes* toxicity as well as *Culex* activity at levels that are not observed in naturally-occurring forms of Cry4Ba. In another embodiment, modified Cry4Ba proteins according to the present invention exhibit enhanced lepidoptera activity. Cry19Aa modified proteins according to the present invention exhibit *Anopheles* and *Culex* toxicity that is comparable to wild-type forms of the protein, but they also exhibit *Aedes* activity that is not observed in naturally-occurring forms of Cry19Aa.

According to the present invention, there is provided a modified Cry4Ba protein comprising an amino acid sequence that is substantially similar to the amino acid sequence shown in FIG. 1, corresponding to SEQ ID NO:1, wherein the sequence of the modified Cry4Ba protein comprises one or more toxicity enhancing modifications in the putative loop 3 of domain II. In preferred embodiments, the modifications are at positions in the amino acid sequence that correspond with exposed residues as determined by three-dimensional modeling. According to these embodiments, the amino acid aspartic acid at position 454 is substituted and at least two additional amino acids are inserted after the substitution, to yield a polypeptide having two additional amino acids and a substitution at position 454. Still further according to these embodiments, the substituted amino acid at position 454 is selected from all known amino acids. In some embodiments, the substituted amino acid at position 454 is a large hydrophobic amino acid, is positively charged, or is negatively charged. Also according to these embodiments, the at least two inserted amino acids after position 454 are selected from all known amino acids. In some embodiments, the at least two inserted amino acids after position 454 are large hydrophobic amino acids, are positively charged, are negatively charged, or are combinations thereof. Good results have been obtained where the aspartic acid at position 454 is replaced with proline, and the amino acids alanine and threonine are inserted after the substituted proline at position 454. Good results have also been obtained where aspartic acid at position 454 is replaced with glycine and the amino acids alanine and valine are inserted after position 454. Good results have also been obtained where the aspartic acid at position 454 is replaced with alanine and the amino acids alanine and threonine are inserted after position 454.

In another embodiment of the present invention, the threonine at position 456 is substituted, the aspartic acid at position 454 is substituted, and at least two additional amino acids are inserted after the substitution at position 454 to yield a polypeptide having two additional amino acids and substitutions at positions 454 and 456. According to this embodiment, the substituted amino acid at position 454 is selected from all known amino acids. In some embodiments, the substituted amino acid at position 454 is a large hydrophobic amino acid, is positively charged, or is negatively charged. Also according to this embodiment, the at least two inserted amino acids after position 454 are selected from all known amino acids. In some embodiments the at least two inserted amino acids after position 454 are large hydrophobic amino acid, positively charged, are negatively charged, or combinations thereof. The substituted amino acid at position 456 is selected from all known amino acids. In some embodiments, the substituted amino acid at position 456 is a large hydrophobic amino acid, is positively charged, or is negatively charged. Good results have been obtained where the threonine at position 456 is replaced with alanine, the aspartic acid at position 454 is replaced with proline and the amino acids alanine and threonine are inserted after position 454.

In another embodiment of the present invention, the aspartic acid at position 454 is replaced, at least two amino acids are inserted after position 454, and one of the following amino acid positions in domain III of the protein is substituted: position 578, 579, 580, and 581. According to this embodiment, the substituted amino acid at position 454 is selected from all known amino acids. In some embodiments, the substituted amino acid at position 454 is a large hydrophobic amino acid, is positively charged, or is negatively charged. Also according to this embodiment, the at least two inserted amino acids after position 454 are selected from all known amino acids. In some embodiments the at least two inserted amino acids after position 454 are large hydrophobic amino acid, positively charged, are negatively charged, or combinations thereof. Also according to this embodiment, the substituted amino acid at each of positions 578, 579, 580, and 581 is selected from all known amino acids. In some embodiments, the substituted amino acid at each of positions 578, 579, 580, and 581 is a large hydrophobic amino acid, is positively charged, or is negatively charged. Good results have been obtained where the aspartic acid at position 454 is replaced with proline, the amino acids alanine and threonine are inserted after position 454, and the asparagine at position 578 is replaced with alanine. Good results have also been obtained where the aspartic acid at position 454 is replaced with proline, the amino acids alanine and threonine are inserted after position 454, and the asparagine at position 579 is replaced with alanine Good results have also been obtained where the aspartic acid at position 454 is replaced with proline, the amino acids alanine and threonine are inserted after position 454, and the isoleucine at position 580 is replaced with alanine. Good results have also been obtained where the aspartic acid at position 454 is replaced with proline, the amino acids alanine and threonine are inserted after position 454, and the isoleucine at position 580 is replaced with phenylalanine. Good results have also been obtained where the aspartic acid at position 454 is replaced with proline, the amino acids alanine and threonine are inserted after position 454, and the isoleucine at position 580 is replaced with tyrosine. Good results have also been obtained where the aspartic acid at position 454 is replaced with proline, the amino acids alanine and threonine are inserted after position 454, and the isoleucine at position 581 is replaced with alanine. Good results have also been obtained where the aspartic acid at position 454 is replaced with proline, the amino acids alanine and threonine are inserted after position 454, and the isoleucine at position 581 is replaced with phenylalanine.

Also according to the present invention there is provided a modified Cry19Aa protein that is substantially similar to the amino acid sequence shown in FIG. 3, corresponding to SEQ ID NO:3 wherein the sequence of the modified Cry19Aa protein comprises one or more toxicity enhancing modifications in both putative loop 1 and putative loop 2 of domain II. In preferred embodiments, the modifications are at positions in the amino acid sequence that correspond with exposed residues as determined by three-dimensional modeling. According to these embodiments, the modification in loop 1 comprises a substitution of amino acids at positions 355 through 358 and an insertion of at least one amino acid after position 358; the modification in loop 2 comprises a deletion of the amino acids at positions 414 through 418. Still further according to this embodiment, the substituted amino acid at each of positions 355 through 358 is selected from all known amino acids. In some embodiments, the substituted amino acid at each of positions 355, 356, 357, and 358 is a large hydrophobic amino acid, is positively charged, or is negatively charged. Also according to this embodiment, the at least one inserted amino acid after position 358 is selected from all known amino acids. In some embodiments the inserted amino acid after position 358 is a large hydrophobic amino acid, positively charged, or negatively charged. Good results have been obtained where the modification in loop 1 comprises a substitution and insertion in which the amino acids serine, tyrosine, tryptophan, and threonine at positions 355 through 358 are substituted with amino acids tyrosine, glutamine, aspartic acid, and leucine, and the amino acid arginine is inserted after position 358; the modification in loop 2 comprises a deletion of the amino acids at positions 414 through 418.

The invention still further includes polynucleotides in the form of recombinant DNA, wherein each such recombinant DNA comprises a modified sequence that encodes a protein comprising an amino acid sequence of one of the above-disclosed modified Cry proteins. In one embodiment, the recombinant DNA has the sequence shown in FIG. 2, corresponding to SEQ ID NO:2 having a modified sequence that encodes a modified Cry4Ba protein, or DNA similar thereto encoding a substantially similar protein. In another embodiment, the recombinant DNA has the sequence shown in FIG. 4, corresponding to SEQ ID NO:4 having a modified sequence that encodes a modified Cry19Aa protein, or DNA similar thereto encoding a substantially similar protein.

The invention also relates to methods for providing Bt toxins having enhanced toxicity to insects, more particularly mosquitoes. The invention involves producing engineered amino acid substitutions in Bt delta-endotoxins. In particular, the invention involves introducing amino acid substitutions into Bt delta-endotoxins having little or no activity against one ore more target insects to create greater activity against said one or more target insects. In some embodiments, the invention involves performing a computational structure modeling and structure-based comparison between two delta-endotoxins to identify appropriate sites for introducing modifications to introduce or enhance activity against one or more target insects. In some instances the modifications are based on matching the sequences between the compared toxins. In other embodiments, the modifications are made to the modified toxin by introduction of other sequence changes not related to the matched toxin. In one embodiment, the invention relates to a method of introducing mutations into the structure of one of the Cry19Aa and Cry4Ba toxins by targeting for mutation exposed loop residues in the structural domains of these proteins that are associated with specific insect toxicities. In one embodiment, the method relates to introducing mutations in the exposed loop residues in loop 3 of domain II of the Cry4Ba crystal toxin so as to confer *Culex* toxicity. In another embodiment, the method relates to introducing mutations in the exposed loop residues in loop 3 of domain II, and domain III of the Cry4Ba crystal toxin so as to confer *Culex* toxicity and enhance *Aedes* and *Anopheles* toxicity. In another embodiment, the method relates to introducing mutations in the exposed loop residues of loops 1 and 2 of domain II of the Cry19Aa crystal toxin so as to confer *Aedes* toxicity.

The invention still further includes a DNA fragment having a DNA sequence complementary to one that hybridizes under stringent conditions with the recombinant DNA according to the invention ("reference sequence"). Examples of such DNA fragments include, but are not limited to, primers used for site directed mutagenesis of the polynucleotide sequences given in SEQ ID NO:2 and SEQ ID NO:4.

Delivery of Bt toxins to target insects: There are various methods for delivery of Bt toxin to target insects.

In some embodiments, the invention relates to methods for reducing or eliminating populations of insects that are vectors of disease, particularly mosquitoes, by delivering into the target insects' habitat the modified Cry4Ba and Cry19Aa proteins as insecticidal agents. In one embodiment, the proteins are used by application in an appropriate formulation to plants and other surfaces in the habitat of the target insect for the ingestion by target insect. In another embodiment, the polynucleotides and vectors of the present invention are used to transfect and express the modified proteins in host organisms, which are then used as food sources for ingestion by insects. In some embodiments, the recombinant organisms are non-viable in the field, and used as delivery capsules for releasing mutant toxins into the habitat of the target insect without introducing the risks associated with viable recombinant organisms. Examples of host organisms transfected with heterologous DNA segments encoding the mutant Cry toxins disclosed herein include microorganisms, such as *P. fluorescens*. These organisms contain encapsulated Bt mutant toxins, but are incapable of reproduction, hence, use of such organisms for Bt toxin delivery reduces concerns associated with testing of living genetically engineered microorganisms. Other examples of host organisms include algae and other unicellular plants or plant like organisms that are ingested by target insects. Yet other examples of host organisms include higher plants that express the crystal toxins in the portions of the plants that are consumed by target organisms, such as the pollen of certain higher plants. In some preferred embodiments, the host organisms produce the modified Cry proteins in non-solubilized crystal form.

In the case that the recombinant DNA is to be introduced into an organism, it may be modified to remove known mRNA instability motifs (such as AT rich regions) and polyadenylation signals, and/or codons that are preferred by the organism into which the recombinant DNA is to be inserted may be used, so that expression of the thus modified DNA in the organism yields substantially similar protein to that obtained by expression of the unmodified recombinant DNA in the organism in which the protein components of the modified Cry proteins are endogenous.

The invention also relates generally to insecticidal compositions comprising mutant toxins with a new or broadened insecticidal spectrum. The insecticidal compositions comprise one or more mutant toxins, such as the various embodiments of modified Cry4Ba and Cry19Aa proteins disclosed herein. The compositions may optionally comprise other insecticidal agents such as other Bt toxins, or different toxins. In preferred embodiments, the insecticidal compositions are formulated in an agriculturally acceptable carrier, diluent and/or excipient. In some embodiments, the insecticidal composition are formulated separately as a wettable powder, emulsifiable concentrate, aqueous or liquid flowable, suspension concentrate or any one of the conventional formulations used for insect control agents and tank mixed in the field with water or other inexpensive liquid for application as a liquid spray mixture. When one or more different insecticidal agents are used, they are in some embodiments applied simultaneously, and in other embodiments they are applied sequentially.

In alternate embodiments, insecticidal compositions may comprise modified organisms that express one or more mutant toxins and may be ingested by target insects to achieve delivery of the mutant toxins. According to such embodiments, polynucleotides encoding one or more mutant toxins are inserted into microorganisms that are associated with the target insect habitat so that the transformed organisms will colonize and continue to produce enough quantities of toxin to affect target insects. Examples of these are the insertion of specific genes into bacteria that colonize plant leaf surface and roots externally, such as *Pseudomonas cepacia*, or internally, such as *Clavibacter xyli*.

Because release of living recombinant microorganisms causes many concerns and regulatory restrictions, alternative methods of introducing genes into microorganisms have been developed to minimize potential horizontal gene flow to other bacterial species. These include using transposase-negative derivatives of Tn5 transposon, or suicide vectors that rely on homologous recombination for integration to be completed. In yet other embodiments, non-viable recombinant organisms may be used to increase toxin persistence in the field include *P. fluorescens*. These organisms contain encapsulated Bt mutant toxins, but are incapable of reproduction, hence, use of such organisms for Bt toxin delivery reduces concerns associated with testing of living genetically engineered microorganisms.

EXAMPLES

The invention may be better understood by reference to the following examples, which serve to illustrate but not to limit the present invention.

Example 1

Cloning and Construction of a Trypsin-site Deletion Mutant of Cry4Ba:

The cry4Ba gene [Genbank Accession Number: X07423] was amplified by PCR with a set of primers (forward primer: FW4AB: 5' GAT Tgg atc cAA TGT AAT ATG GGA G 3'-lower case letter indicate BamHI site, and reverse primer: RE4AB: 5' TAT TTT Tgg tac cAG AAT TAA TAA ATG CAG 3'-lower case letter indicate KpnI site) and subcloned into plasmid pTZ19R (Fermentas) that was double-digested with BamHI and KpnI. The cry4Ba gene was put under the control of the lac promoter of the vector in this construct. This construct was transformed into DH5α *Escherichia coli* cells for DNA isolation and protein expression. The wild-type Cry4Ba prototoxin produced a ~46 kDa toxin fragment when digested with trypsin. This fragment was found to be inactive. The trypsin site was removed by mutating R203 to A by site-directed mutagenesis. The mutated toxin was called 4BRA, and it produced a ~66 kDa toxin fragment, instead of the 46 kDa fragment.

Figure 5:
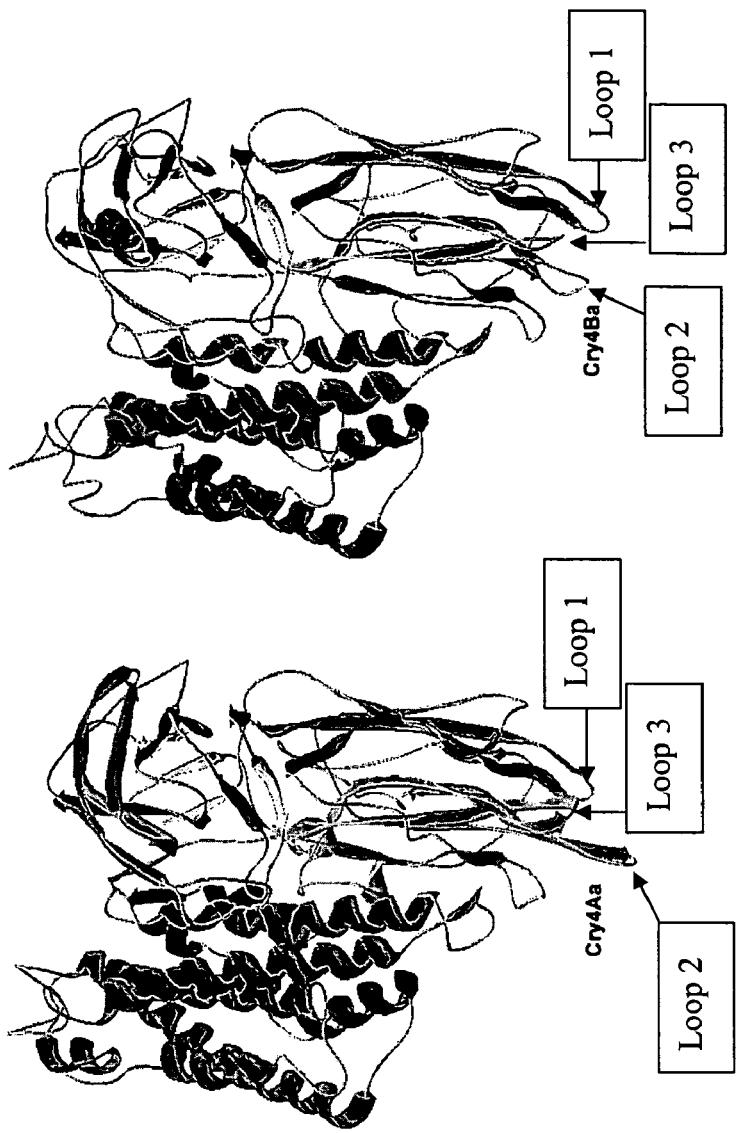
FIG. 5: (a) Ribbon representation of model structures of Cry4Aa (left) and Cry4Ba (right), and (b) Cry4Ba (left) and Cry19Aa (right). The arrows denote the positions of the loop regions of domain II.
Figure 5:
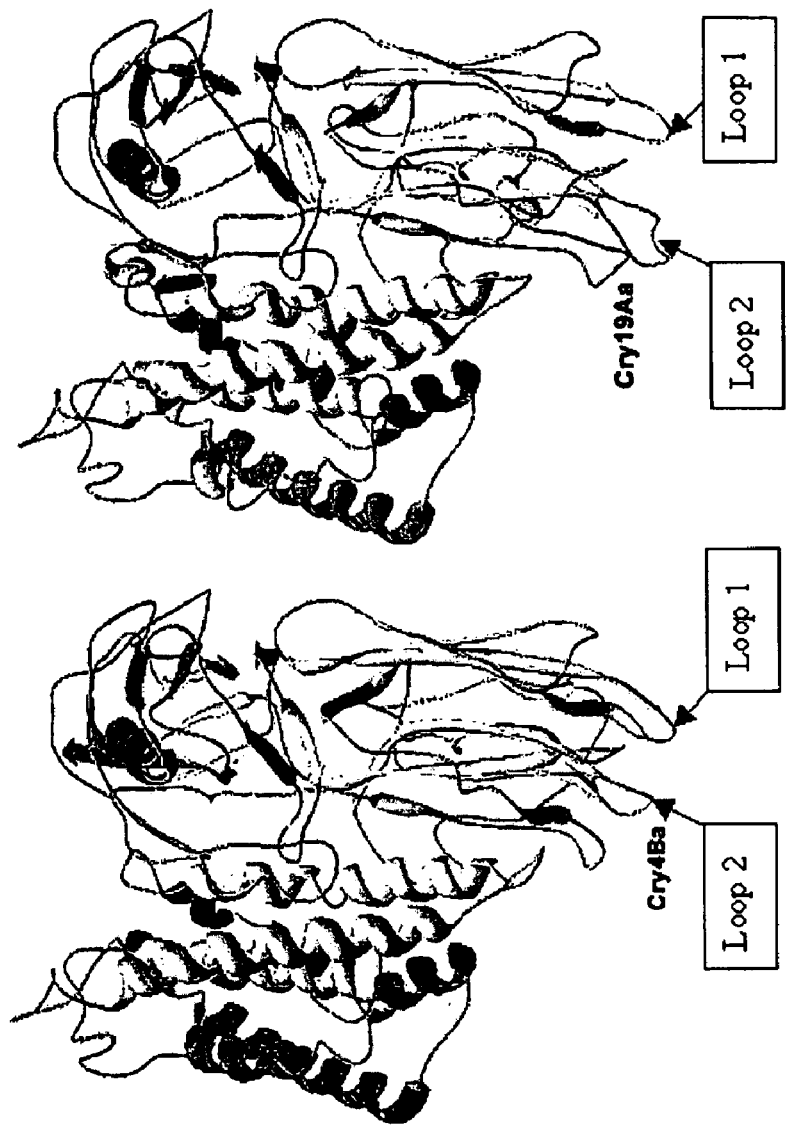

Cry4Aa was compared with Cry4Ba by sequence alignment and molecular modeling with Swiss-Model. The predicted structures (FIG. 5), while not precise, indicated general homology of secondary and tertiary structure. These alignments allowed loop regions of domain II to be compared (FIG. 6). The alignment of loops provided a basis for site-directed mutagenesis to substitute amino acid residues on the loops of Cry4Ba with their non-homologous counterparts from Cry4Aa so that its *Culex* activity might be transferred to Cry4Ba.

Mutating Cry toxins by site-directed mutagenesis: Site-directed mutagenesis was performed using the modified QuickChange (Stratagene) method. DNA templates were purified using a plasmid purification kit (Qiagen). Purified templates (3 μg) were methylated using 8 U of dam methylase (New England Biolabs) for 15 mm at 37° C. The reaction was stopped on ice. For polymerase chain reaction (PCR), 100 to 200 ng of methylated DNA was mixed with 15 pmol of forward and reverse mutagenic primer, 300 μM (final concentration) of each deoxynucleotide triphosphate (dNTP mix, Roche), 0.5 U of Expand Long Template Polymerase (Roche), 1× Buffer I (Roche) in a total volume of 25 μl. The sequences of the primers are listed in Table 1.

TABLE 1

Sequences of primers (SEQ ID NOS 11-28) used in site-directed mutagenesis.

| Primer* | Sequence (5' → 3') | Mutant |
|---|---|---|
| Fw4BR203A | GGTCTTTAGCAGCTAGTGCTGGTGACC | 4BRA |
| Re4BR203A | GGTCACCAGCACTAGCTGCTAAAGACC | |
| Fw4BL1QTT | ACCAATACTCAAACTACAGATTTAAGATTTTTATC | 4BL1QTT |
| Re4BL1QTT | TCTTAAATCTGAAGTTTGAGTATTGGTCCAGAAATC | |
| Fw4BL2NDY | CTAATCGAGTTAATGATTATACAAAAATGGATTTC | 4BL2NDY |
| Re4BL2NDY | CATTTTTGTATAATCATTAACTCGATTAGAGGGTATTC | |
| Fw4BL3PAT | GATGTTATACCTGCGACTTATAACAGTAACAGGGTTTC | 4BL3PAT |
| Re4BL3PAT | CTGTTATAAGTCGCAGGTATAACATCAGTTTTTATATAG | |
| Fw4BL3AAT | GATGTTATAGCTGCGACTTATAACAGTAACAGGGTTTC | 4BL3AAT |
| Re4BL3AAT | CTGTTATAAGTCGCAGCTATAACATCAGTTTTTATATAG | |
| Fw4BL3GAT | GATGTTATAGGTGCGACTTATAACAGTAACAGGGTTTC | 4BL3GAT |
| Re4BL3GAT | CTGTTATAAGTCGCACCTATAACATCAGTTTTTATATAG | |
| Fw4BL3GAV | GATGTTATAGGTGCGGTTTATAACAGTAACAGGGTTTC | 4BL3GAV |
| Re4BL3GAV | CTGTTATAAACGCGCACCTATAACATCAGTTTTTATATAG | |
| Fw4BL3PAA | GATGTTATACCTGCGGCTTATAACAGTAACAGGGTTTC | 4BL3PAA |

TABLE 1-continued

Sequences of primers (SEQ ID NOS 11-28) used in site-directed mutagenesis.

| Primer* | Sequence (5' → 3') | Mutant |
|---|---|---|
| Re4BL3PAA | CTGTTATAAGTCGCAGGTATAACATCAGTTTT TATATAG | |
| Fw4BL3AAA | GATGTTATAGCTGCGGCTTATAACAGTAACAG GGTTTC | 4BL3AAA |
| Re4BL3AAA | CTGTTATAAGCCGCAGCTATAACATCAGTTTT TATATAG | |

*The sets of complementary primers for creating the mutants are grouped together.

The programmed steps for the PCR reaction were as follows:

| Step | Reaction | Temperature | Duration |
|---|---|---|---|
| 1. | Initial Denaturation | 94° C. | 2 min |
| 2. | Denaturation | 94° C. | 10 s |
| 3. | Annealing | 48° C. | 30 s |
| 4. | Elongation | 68° C. | 4 min |
| 5. | Repeat steps 2-4 9 times | | |
| 6. | Denaturation | 94° C. | 15 s |
| 7. | Annealing | 48° C. | 30 s |
| 8. | Elongation | 68° C. | 4 min + 20 s every successive cycle |
| 9. | Repeat steps 6-8 15 times | | |
| 10. | Final elongation | 68° C. | 7 min |
| 11. | Cooling | 4° C. | unlimited |

The PCR thermal cycle machine used was MiniCycler (MJ Research). After the PCR was completed, the reaction product was digested with DpnI (Roche) to remove the methylated template DNA. The digested PCR product was used to transform *E. coli* DH5α competent cells. Mutations were confirmed by automated DNA sequencing (Plant-Microbe Genomics Facility, The Ohio State University).

Isolating and purifying Cry toxin: *E. coli* cells containing the toxin construct was grown on Luria Bertani (LB) agar plates supplemented with 100 μg/ml of ampicillin at 37° C. A single colony was inoculated into 5 ml of LB broth and incubated overnight at 37° C. in an incubator-shaker at 250 rpm. A 2 ml overnight culture was inoculated into 500 ml of modified Terrific Broth (24 g/L yeast extract, 12 g/L tryptone, 2% glycerol, 25.08 g/L $K_2HPO_4$, 4.62 g/L $KH_2PO_4$), supplemented with 100 μg/ml ampicillin, and grown for 72 h at 37° C. in an incubator-shaker at 250 rpm.

Cells were harvested by centrifugation at 9,820×g for 10 min at 15° C. with a JA-14 rotor in an Avanti J-25 centrifuge (Beckman). The supernatant was discarded and the pellet was resuspended in 50 ml of lysis buffer (50 mM Tris, 50 mM EDTA, 15% sucrose, pH 8.0), supplemented with 20 mg of lysozyme. The suspension was incubated at 37° C. for 3 h in an incubator-shaker shaking at 250 rpm. Subsequently, the suspension was centrifuged in a JA-14 rotor at 15,344 g for 10 min at 4° C. The resulting thick supernatant was discarded carefully with attention paid towards not losing the loose pellet. The pellet was resuspended in 80 ml of crystal wash I (2% Triton X-100, 0.5 M NaCl) and was cooled on ice for 10-15 min prior to sonication (1:30 min, 5 s burst, 50% duty, ½" tip, no. 8 on output control) on ice, using a W-385 sonicator (Heat Systems Ultrasonics, Inc). The suspension was cooled on ice for 5 min and later shaken by hand in a centrifuge bottle for 30 s. The suspension was centrifuged in a JA-14 rotor at 12,429×g for 5 min at 4° C. The supernatant was discarded and the pellet was resuspended in 80 ml of crystal wash I. Next, the suspension was centrifuged and resuspended as before, twice. Later, the pellet from the last step was resuspended in crystal wash II (0.5 M NaCl). The suspension was centrifuged and resuspended as before, three times in this solution. Next, the pellet from the last step was resuspended in 80 ml of sterile deionized distilled water ($ddH_2O$) and centrifuged as before. The pellet was resuspended in 2 ml of sterile $ddH_2O$ and kept at 4° C. until needed. Crystal inclusion protein was solubilized in carbonate buffer (30 mM $Na_2CO_3$, 20 mM $NaHCO_3$, pH 10.0) and protein concentration was measured using the Coomassie protein assay reagent (Pierce) with bovine serum albumin as standard. For binding assays, solubilized toxin was incubated with 1/20 (v/v) 10 mg/ml trypsin (Sigma) at 37° C. for 3 h. The activated toxin was purified by HPLC using a Superdex 200 (Pharmacia) column.

Determining toxicity of Cry toxins by mosquito larvae bioassay: Colonies of the mosquitoes were reared in an environment-controlled room at 28° C. and 85% humidity, with a photoperiod of 14-h light/10-h dark. The *An. quadrimaculatus* culture was a kind gift from Peggy Hodges (University of Notre Dame), *Ae. aegypti* and *Cx. quinquefasciatus* cultures from Allan Yousten (Virginia Polytechnic Institute), and *Cx. pipiens* (recently isolated from nature in Ohio) from Rebecca Moll and Woodbridge Foster (Ohio State University). Adult mosquitoes were maintained on heparinated cow blood, sugar cane cubes (Domino Dots) and dechlorinated tap water. *Aedes* and *Culex* larvae were maintained on fish food pellets (Koi Floating Blend, Aquaricare™), while *Anopheles* larvae were maintained on 2:1 ratio of ground fish food flakes (Vitapro™ Plus Cichlid Power Flakes, Mike Reed Enterprises) and brewers yeast, as suggested by Mark Q. Benedict (Centers for Disease Control and Prevention). Second instar larvae were used for all bioassays. Bioassays were performed on different days after hatching due to the different growth rate of the mosquito larvae. *Ae. aegypti*, *Cx. quinquefasciatus* and *Cx. pipiens* larvae were tested two days after hatching, while *An. quadrimaculatus* larvae were tested three days after hatching. A total of six larvae per 2.5 ml of water with one replicate in a 24 well Costar™ cell culture plate (Corning) were fed a serial dilution of Cry toxins and the number of mortalities was counted after a 24-hour incubation at 30° C.

The bioassay was repeated to obtain a reasonable lethal concentration range, where applicable, and the $LC_{50}$ was calculated by a Probit method using SoftTOX™ ver. 1.1 (WindowChem™).

Preparing mosquito brush border membrane vesicles (BBMV): Fourth instar mosquito larvae were filtered with a nylon mesh, washed in distilled water, separated from large residual food particles, and dried briefly on a filter paper (Fisher) under vacuum suction. Harvested larvae were frozen at −70° C. until needed. 4-6 g of frozen larvae were homogenized in 8-12 ml of cold buffer A (300 mM mannitol, 5 mM EGTA, 17 mM Tris-HCl, pH 7.5). Larvae were homogenized by 40 strokes of Potter-Elvehjem PTFE pestle in glass tube at speed number 5 (~6000 rpm). The homogenized sample was centrifuged at 11,159×g for 5 min at 4° C. in a JA-17 rotor. The pellet was discarded while the supernatant was kept for the next step. The supernatant was filtered through a Whatman (No. 1) filter paper under vacuum and the filtrate was collected on ice. Meanwhile, tubes containing continuous sucrose gradient were prepared by mixing 15 ml of $ddH_2O$ with 15 ml of 45% Sucrose (w/v in $ddH_2O$) in a gradient maker. A 4 ml filtrate prepared previously was layered carefully on top of the gradient with a 10 ml glass pipette. The tubes were placed inside tube holders and balanced. The tubes were centrifuged at 15,000 rpm for 2 h at 4° C. in an SW28 rotor. After the centrifugation, the top layer was removed by suction and discarded, leaving the lowest visible layer or the pellet. This layer was transferred to a new tube, resuspended in cold sterile $ddH_2O$, and centrifuged at 35,267×g for 15 min at 4° C. in a JA-17 rotor. The supernatant was discarded and any loose pellet was rinsed off with binding buffer (60 mM $K_2HPO_4$, 5 mM $KH_2PO_4$, 150 mM NaCl, 10 mM EGTA, pH 7.00). The BBMV pellet was resuspended in 1 ml of ice-cold Binding Buffer supplemented with COMPLETE™ (Roche) protease inhibitor and homogenized by 10 extrusions using a small Teflon pestle. The protein concentration of the BBMV was measured with the Coomassie protein assay reagent (Pierce), using BSA as the standard. The BBMV was distributed into 0.5 ml aliquots and kept at −70° C. until needed. The activity of aminopeptidase N (a brush border membrane marker) was tested at each step of an *Anopheles* BBMV preparation. There was a 5.5-fold enrichment of aminopeptidase N compared to the larval homogenate, which suggested that this was an acceptable method for preparing BBMV.

Radioactive labeling of Cry toxin: Activated toxins were iodinated as previously described. Briefly, 0.3 to 0.5 mCi of Na $^{125}$I (Perkin Elmer) from the stock vial was incubated with one iodo-bead (Pierce) for 5 min at room temperature. Later, an HPLC-purified toxin in carbonate buffer (30 mM $Na_2CO_3$, 20 mM $NaHCO_3$, pH 10.0) (45 μg in 0.1 ml carbonate buffer) was added to the bead and was incubated a further 5 min. The reaction mix was removed from the iodo-bead and was applied to a 2-ml Excellulose column (Pierce) to remove free iodine from the toxin.

Reversible binding assay: The course of toxin binding to BBMV was suggested to occur through a two-step process involving reversible and irreversible steps. In this assay, 10 μg of mosquito BBMV were incubated with 1 nM of $^{125}$I-labeled toxin in 0.1 ml of binding buffer with increasing amount of unlabeled toxin for a period of 1 h at room temperature. The reaction was centrifuged at 27,000×g for 10 min to separate unbound labeled toxin from the BBMV. The supernatant was discarded while the pellet was washed twice with binding buffer. The resulting pellet was counted in a gamma counter (Wallac) and the data were plotted with SigmaPlot ver. 8.0 (SPSS, Inc.).

Irreversible binding assay: In this binding assay, 2 μg of mosquito BBMV was incubated with 2 nM of $^{125}$I-labeled toxin in 0.1 ml of binding buffer for 1 h at room temperature. Then 1000 nM (final concentration) was added to the binding reaction and was incubated for different length of time. Unbound labeled toxin was separated from the BBMV and the resulting data was obtained as mentioned above. Non-specific binding data were obtained by incorporating the unlabeled toxin with the labeled toxin at the start of the assay and incubated with the BBMV for the maximum duration of the assay period.

Saturation binding assay: In this binding assay, 0.5 to 1.0 μg of mosquito BBMV were incubated with an increasing concentration of $^{125}$I-labeled toxin in 0.1 ml of binding buffer for 1 h at room temperature. Non-specific binding was obtained by incubating the reaction with at least 250-fold excess of unlabeled toxin. Specific binding was obtained by subtracting the non-specific binding counts from the total binding counts. As before, unbound labeled toxin was separated from the BBMV and the resulting data was obtained as mentioned above.

Proteinase K protection assay: In this assay, 5 μg of *Ae. aegypti* BBMV was incubated with either 10 nM of $^{125}$I-labeled 4BRA or 4BL3PAT in 0.1 ml of binding buffer for 1 hr at room temperature. Later, 10 μg of proteinase K (Roche) was added and incubated a further 20 min. The action of the protease was stopped by 100 μg pefabloc sc (Roche). The reaction was centrifuged at 15,000 rpm for 10 min at room temperature to separate the remaining toxin bound/inserted in the BBMV. The pellet was washed two times with binding buffer without resuspending the pellet.

Secondary structure analysis by circular dichroism (CD) spectroscopy: Trypsin-activated toxins were purified by HPLC as described above and concentrated to at least 1 mg/ml using centricon (YM-30, Millipore). Concentrated toxins were diluted in a phosphate buffer (10 mM $KH_2PO_4$/$K_2HPO_4$, 40 mM NaCl, pH 7.4) prepared in Milli-Q (Millipore) water. CD data were collected at room temperature with a 1-cm path length quartz cell (Hellma) on an AVIV Model 62A DS spectrophotometer, scanning from 250 to 200 nm in 1.0 nm steps. Data obtained were based on the average of 10 scans.

Mosquito bioassay of Cry4Ba and its muteins: Bioassays on $2^{nd}$ instars mosquito larvae were performed to test the mosquitocidal activities of toxins. The results of the bioassays that are shown in Table 2 indicated that the mutations in the predicted loop regions of domain II affected toxicities against the three genus of mosquito. Mutation in loop 1 of 4BRA to mimic the loop 1 of Cry4Aa, 331IYQ333 to QTT (4BL1QTT), caused the toxin to lose activity against *Ae. aegypti* and *An. quadrimaculatus*. Meanwhile, the mutation in loop 2, where NDY was inserted between V393 and T394 (4BL2NDY), also caused the toxin to lose activity against the two mosquitoes. On the contrary, the mutation in loop 3, where D454 was replaced with P and AT was inserted after position 454, caused the toxin to gain activity against *Cx. quinquefasciatus* and *Cx. pipiens*, while still maintaining activity against both *Aedes* and *Anopheles*.

TABLE 2

Bioassay results of four species of mosquitoes.

| | (LC$_{50}$ in ng/ml)‡ | | | |
|---|---|---|---|---|
| Toxins | An. quadrimaculatus | Ae. aegypti | Cx. quinquefasciatus | Cx. pipiens |
| Cry4Ba | 25 (18-32) | 61 (28-175) | >80,000$^a$ | >20,000$^a$ |
| 4BwtGAV | 745 (607-962) | 174 (117-280) | >20,000$^a$ | ND |
| 4BRA | 21 (15-29) | 21 (5-51) | >80,000$^b$ | >20,000$^a$ |
| 4BL1QTT | >20,000$^b$ | >20,000$^b$ | >20,000$^b$ | ND |
| 4BL2NDY | >20,000$^b$ | >20,000$^b$ | >20,000$^b$ | ND |
| 4BL3PAT | 44 (40-50) | 53 (19-91) | 365 (267-529) | 95 (69-130) |
| 4BL3AAT | 16 (8-23) | 68 (19-140) | 1035 (485-8972) | 229 (142-512) |
| 4BL3PAA | 197 (136-328) | 144 (75-277) | 4000 (1948-14,838) | 481 (44-988) |
| 4BL3AAA | 23 (17-30) | 82 (50-126) | >20,000$^b$ | 630 (306-11,328) |
| 4BL3GAT | 88 (64-119) | 64 (39-94) | 122 (75-189) | 180 (117-317) |
| 4BL3GAV | 52 (32-74) | 44 (20-68) | 114 (83-150) | 70 (34-129) |

‡2-day old larvae of *Ae. aegypti*, *Cx. quinquefasciatus* and *Cx. pipiens*; 3-day old larvae of *An. quadrimaculatus* were used for bioassays. Mortality was recorded after 24 hours exposure to a serial dilution of the toxins. The 95% confidence limit is indicated in parentheses. Bioassays for the cry4B constructs used purified inclusion crystal protein (ICP) produced in *E. coli*.
$^a$8% mortality was observed at this dose.
$^b$No mortality was observed.
$^c$17% mortality was observed at this dose.
ND—Not determined.

Alanine scanning in loop 3 caused variable toxicities against the different species of mosquito used in this study. When P454 in the 4BL3PAT construct was mutated to A (4BL3AAT), toxicity against *An. quadrimaculatus* improved 2.8 fold. However, the same mutation did not significantly alter its toxicity towards *Ae. aegypti*, but it reduced its toxicity by the same amount against the two *Culex* species. The reduction in toxicity was more extensive in *Cx. quinquefasciatus* than in *Cx. pipiens*. When T456 in the 4BL3PAT construct was mutated to A (4BL3PAA), toxicity was reduced against *An. quadrimaculatus*, *Ae. aegypti*, and both *Culex* species. However, when both P454 and T456 were mutated to A to yield 4BL3AAA, its activity against *An. quadrimaculatus* was improved 2 fold. The toxicity against *Ae. aegypti* was not significantly affected but its toxicity against both *Culex* species was significantly reduced, with *Cx. quinquefasciatus* toxicity the most affected. The differences in toxicities of these mutants to the different *Culex* species suggested that the toxins were acting through different mode of action, although in the same *Culex* genus. The results indicated that P454A mutation improved toxicity against *Anopheles* in both 4BL3AAT and 4BL3AAA constructs. The Pro residue at position 454 and Thr residue at position 456 influenced *Culex* toxicity. The alanine scanning did not affect significantly on the toxicity against *Aedes*.

When P454 was mutated to G (4BL3GAT), activity against *An. quadrimaculatus* reduced 2 fold, while the activity against *Cx. quinquefaciatus* was increased by 3 fold. The activities against *Ae. aegypti* and *Cx. pipiens* were not significantly different compared to 4BL3PAT. The results indicated that the Gly residue at position 454 was more important for *Culex* toxicity. The polar (hydroxyl) group in Thr did not appear to be important for *Culex* toxicity as the Val residue could replace the Thr residue at position 456 while not affecting significantly the previous toxicity. However, as an alanine in this position (in 4BL3PAA) would reduce the *Culex* activity, it is apparent that the length of the aliphatic side chain (same for both Val and Thr) might play a role.

Mutation of R203 to A in the loop area between two alpha helices to remove a trypsin cleavage site did not significantly improve toxicities against *Ae. aegypti* and *An. quadrimaculatus* for Cry4Ba. However, when the trypsin cleavage site was not removed in the 4BwtGAV construct, it caused a significant reduction in the activity against *Aedes* (4 fold) and *Anopheles* (14.3 fold) when compared to 4BL3GAV. Most importantly, it lost its activity against *Culex*.

Binding assays: Saturation binding assay results (FIGS. 7A, 5B, 5C) show that the binding sites on the BBMV were saturated by 4BRA. This assay demonstrated that the BBMV preparation technique in this study produced BBMV that were suitable for binding assays. The sigmoidal shapes of the binding curves indicated that there were positive cooperative binding of the toxin to the BBMV, even to *Cx. quinquefasciatus* BBMV, which 4BRA was determined to be non toxic. The specific binding data was fitted by nonlinear regression using SigmaPlot Ver. 8.0 (SPSS) to a Hill equation, $y=a \cdot x^b/(c+x^b)$, where "a" represents B$_{max}$, "b" represents Hill coefficient, and "c" represents K'$_D$ (a composite dissociation constant composed of the intrinsic dissociation constants for each discreet binding step). The degree of fitness was very high ($R^2 > 0.98$) for all the saturation binding assays. The values obtained from the fitting are as listed in Table 3.

TABLE 3

Nonlinear regression results for the specific binding of 4BRA to BBMV from three mosquito species.

| | B$_{max}$ (fmol/µg) | K'$_D$ (nM) | Hill Coefficient |
|---|---|---|---|
| Ae. aegypti | 17.2 ± 1.0 | 0.5 ± 0.4 | 4.4 ± 2.8 |
| An. quadrimaculatus | 35.2 ± 2.0 | 3.1 ± 1.2 | 3.0 ± 0.9 |
| Cx. quinquefasciatus | 13.1 ± 0.6 | 6.9 ± 2.7 | 4.8 ± 0.9 |

For comparison, a saturation binding assay was performed using $^{125}$I-4BL3PAT and *Cx. quinquefasciatus* BBMV (FIG. 7D). Table 4 compares the saturation binding results of 4BRA and 4BL3PAT to *Cx. quinquefasciatus* BBMV. It appears that 4BL3PAT has less specific binding sites (B$_{max}$), a lower Hill coefficient number and a tighter binding to the BBMV than 4BRA.

TABLE 4

Nonlinear regression results for the specific binding of 4BRA and 4BL3PAT to *Cx. quinquefasciatus* BBMV.

| Toxin | $B_{max}$ (fmol/mg) | $K'_D$ (nM) | Hill Coefficient |
|---|---|---|---|
| 4BRA | 13.1 ± 0.6 | 6.9 ± 2.7 | 4.8 ± 0.9 |
| 4BL3PAT | 9.3 ± 0.4 | 0.9 ± 0.2 | 2.8 ± 0.5 |

There is a possibility that 4BRA and 4BL3PAT might share some binding sites on the *Culex* BBMV. If the assumption that excess cold 4BRA (cold refers to unlabeled toxin while hot refers to $^{125}$I-labeled toxin) blocks all 4BRA sites on the BBMV, which includes shared binding sites with 4BL3PAT but not the specific 4BL3PAT sites, then the binding data would yield the specific binding data of 4BL3PAT to the BBMV. This assumption, however, excludes the fact that 4BL3PAT can bind non-specifically to sites on the BBMV that are not overlapping with 4BRA sites. However, the results show that the blocking of binding sites using cold 4BRA produced a lower binding counts compared to using cold 4BL3PAT, which was the opposite of what one would expect if there were more binding sites available for 4BL3PAT. A possible model would be that the number of shared sites is more than the number of specific 4BL3PAT sites on the BBMV. The lower binding counts would also suggest that less positive cooperative binding occurred between 4BL3PAT and 4BRA than between 4BL3PAT to itself. It appears that loop 3 in domain II of Cry4Ba affects the positive cooperative binding nature of the toxin.

The ability of the inactive and active toxin to reversibly bind to the BBMV of *Cx. quinquefasciatus* was tested in the binding assay of 4BRA and 4BL3PAT. The results for the reversible binding assay of 4BRA toxin and 4BL3PAT to *Cx. quinquefasciatus* BBMV that are shown (FIG. 8) indicated that there was no significant difference in the ability to reversibly bind the BBMV for both the non-active 4BRA and the active 4BL3PAT. The ability of the toxins to irreversibly bind to the BBMV is shown in FIG. 9. There was also no significant difference in the ability to irreversibly bind the BBMV for both 4BRA and 4BL3PAT.

Proteinase K protection analysis: Membrane associations of Cry toxins are tested using proteinase K protection assays. The basis of this assay is the expectation that membrane-bound toxins are insensitive to proteinase K, a non-specific protease. The results in FIG. 10 show that 4BRA is more protected than 4BL3PAT.

It was observed that 4BL3PAT had acquired a moderate level of toxicity (LC50≈2520 ng/cm$^2$) to the lepidopteran, *Manduca sexta*. Cry4Ba has no toxicity to *M. sexta*. Another mutation in loop 3, where D454 was replaced with G and AV, after position 454 (4BL3GAV), was introduced to match the GAV, found in Cry1Aa at loop 3. This mutation caused the toxin to improve toxicity slightly against *M. sexta*, albeit with overlapping confidence limits. Voltage-clamp experiments were performed to compare the ion channel activity of Cry toxins. Bt Cry toxins have been shown to behave as potassium channels and disrupt the potassium flux, which is generated by ion pumps in the goblet cells of the midgut wall. The results suggested that 4BL3GAV caused greater ion channel activity in *M. sexta* midgut membranes than 4BL3PAT, 4BRA and Cry4Ba, in descending order. 4BRA had better ion channel activity than Cry4Ba, suggesting that the removal of a trypsin cleavage site from domain I, enhanced ion channel activity. Cry1Aa, which is very toxic to *M. sexta* (LC50≈2.3 ng/cm$^2$), was included as a positive control. Also, 4BL3GAV was 3 fold more toxic against *Cx. quinquefasciatus* compared to 4BL3PAT. The same enhancement was not observed against *Cx. pipiens*, *An. quadrimaculatus* and *Ae. aegypti*, as 4BL3GAV was equally toxic to these mosquitoes compared to 4BL3PAT.

Secondary structure analysis: CD spectrum were averaged and compiled in FIG. 11. The CD spectrum of the activated toxins of Cry4Ba and its mutants were found to be insignificantly different from each other. This indicated that there was no significant perturbation in the secondary structure of the toxins due to the mutations. The CD spectrum of wild-type Cry4Ba was of interest because it was nicked by trypsin at position between R203 and S204 (indicated by N-terminal amino acid sequencing result), yet it was not significantly different from 4BRA (trypsin site was removed) and other mutants based on 4BRA.

The blocking of the trypsin site in domain I of Cry4Ba did not increase significantly its activity against *Anopheles* and *Aedes*. However, in a previous study, it was reported that this mutation increased the toxicity of the toxin to *Aedes*. The wild-type Cry4Ba was cleaved by gut juice of *Cx. pipiens* into 18 kDa and 46 kDa fragments, similar to the results that were obtained by trypsin digestion in this study (FIG. 12, lane 2). The fragments were observed to be associated with each other by gel filtration chromatography (result not shown), agreeing with the results of Yamagiwa et al. Secondary structural analysis showed that differences between the wild-type Cry4Ba and its mutants were insignificant (FIG. 11). These results suggested that the nicking in domain I did not perturb the overall structure of the toxin. The results in Table 2 show that there was an increase in toxicity of 4BRA relative to Cry4Ba by 2.9 fold but the 95% confidence limit of the toxins overlapped. It was therefore considered to be an insignificant difference. However, the effect due to the blocking of the trypsin cleavage site was more pronounced in another construct, called 4BwtGAV, by reintroducing the cleavage site into 4BL3GAV. This mutant was 4.0 fold less toxic to *Aedes*, 14.3 fold less toxic to *Anopheles*, and it also lost its toxicity to *Culex*.

Bioassays against four species of mosquitoes with the wild-type Cry4Ba toxin, 4BRA toxin, and the loop muteins are shown in Table 4. The data indicate that by introducing three residues (PAT) from the loop 3 of Cry4Aa into 4BRA caused a tremendous increase in activity against *Culex*. Variation of this sequence caused variable effects on toxicity to the mosquitoes tested. However, mutations in loop 1 and 2 to introduce residues from Cry4Aa significantly disrupt toxicity against both *Anopheles* and *Aedes*, but did not introduce activity against *Culex*. The PAT sequence in loop 3 was analyzed by alanine scanning. The results revealed that P454 and T456 influenced *Culex* activity. The Pro residue could be exchanged with a Gly residue to increase the *Culex* activity further. The polarity of the Thr residue was not critical, as a Val residue could replace it with similar *Culex* activity. *Aedes* activity was not significantly affected by the alanine scanning. However, *Anopheles* activity was significantly increased by P454A mutation (in 4BL3AAT and 4BL3AAA). All the variations in loop 3 that were constructed involved conservative mutations, as no charged residue was used. Other residues could be substituted to further improve the mosquitocidal activity of the toxin. In summary, loop 3 was particularly important for *Culex* activity but also could affect *Anopheles* activity. Loops 1 and 2 significantly influenced *Aedes* and *Anopheles* activities, but their influence on *Culex* activity was not tested vigorously.

The analysis of binding properties of Cry toxins to BBMV is used to correlate a toxin's insect specificity with its affinity for specific receptors on BBMV of susceptible insects. Binding to brush border membrane vesicles (BBMV) is purported to be a two-step process involving reversible and irreversible steps. Competition binding of 4BRA toxin and 4BL3PAT to *Cx. quinquefasciatus* BBMV indicated that there was no difference in the ability to reversibly bind the BBMV for both the non-active 4BRA and the active 4BL3PAT (FIG. 8). Further experiments with irreversible binding assays indicated that there was also no significant difference in the ability of the muteins and wild-type toxins to irreversibly bind BBMV (FIG. 8). It is worth noting that there is a possibility that the irreversible binding results might not be representing membrane insertion.

The saturation binding data (FIGS. 7A, 7B, and 7C) demonstrated that 4BRA was binding in a positive cooperative manner to the BBMV. 4BL3PAT was also shown to bind cooperatively to *Cx. quinquefasciatus* BBMV (FIG. 7D). Although some differences were observed (Table 4), the results were not showing large differences to account for the large divergence in toxicity between 4BRA and 4BL3PAT to *Culex* larvae. The observation of positive cooperative binding for Cry toxins to BBMV has not been reported up until now. The very tight binding of the non-active toxin (4BRA) to the *Culex* BBMV could explain the insignificant difference in the irreversible binding assay between 4BRA and 4BL3PAT. These results indicated that 4BRA and 4BL3PAT bound equally well to *Cx. quinquefasciatus* BBMV.

The positive cooperative binding demonstrated by 4BRA suggested that there were more than one binding sites available for toxin-BBMV interaction. These sites were dependent sites, which means that after the binding of the first toxin molecule, the next toxin molecule would bind much easier to the BBMV. A BBMV molecule, R can be assumed to have n binding sites for toxin, T, and that immediately after one molecule of T binds, the remaining (n−1) sites are immediately occupied. This simplistic view of receptor-ligand binding may be represented as $R+nT \leftrightarrow RT_n$. A Hill equation, which represents the cooperative binding, can be written as $$B = \frac{B_{max} \cdot [T]^n}{K'_D + [T]^n} \quad (1)$$

where B is the amount of bound ligand, [T] is the ligand concentration, $B_{max}$ is the maximum amount of bound ligand, n is the "Hill coefficient", which cannot exceed the number of ligand binding sites per receptor molecule, and $K'_D$ is the composite dissociation constant. However, since the binding of Cry toxins to BBMV eventually leads to irreversible insertion of the toxin into the membrane of BBMV, the following binding equation describes the irreversible binding kinetics $$T + R \underset{k_{-1}}{\overset{k_1}{\rightleftharpoons}} T \equiv R \overset{k_2}{\longrightarrow} *T(\text{or } *TR) \quad (2)$$

where *T is an irreversibly bound toxin, presumably inserted into the membrane but not associated with a receptor; and *TR is an irreversibly bound toxin that is still associated with a receptor. The inability of the binding reaction to reach equilibrium due to the irreversible step would invalidate the values of the calculated parameters in equation 1. The calculated values should be treated as qualitative description of the parameters. Despite the non-adherence to the equilibrium rule, the specific binding data of 4BRA to three different species of mosquito BBMV fitted very well to equation 1 ($R^2 > 0.98$). From the results in Table 3, the values for n suggest that there were 3 dependent binding sites in *An. quadrimaculatus*, and 5 dependent binding sites in both *Ae. aegypti* and *Cx. quinquefasciatus* for 4BRA. The number of binding sites could represent the number of different receptors on the BBMV. It could also mean that 4BRA formed trimers or pentamers in the BBMV. Cry toxins have been demonstrated to form oligomers in the membrane of BBMV. This would also suggest that 4BRA might have different mode of action for the different mosquito species. The ability of 4BRA to bind sequentially to the different mosquito BBMV suggested a common step in the mode of action of this toxin. However, since 4BRA was not toxic to *Cx. quinquefasciatus* even though its binding characteristic was similar to the other mosquito species, there should be a process beyond this, which was different that affected toxicity.

Another approach of measuring toxin-membrane association is to perform proteinase K protection assays. Toxins in their unbound state and receptor-bound state on the surface of BBMV would be degraded in the presence of proteinase K. However, toxins that are membrane-bound or membrane-inserted, would be insensitive to proteinase K. The results shown in FIG. 10 suggested that more inserted toxins did not translate into higher toxicity. There is a possibility that the membrane insertion action of 4BRA did not produce ion channels or pores in the membrane. This model is supported by a report that says that although the ability of a Cry1Ac mutant to bind to BBMV and form aggregates in the membrane was not affected, a decreased toxicity was correlated to the reduced ability to form ion channels. The report, however, was describing the effect of mutations in domain I to ion channel formation, and it would appear that domain II might be involved in ion channel formation as well. Another model to describe the negative correlation between the amounts of toxin protected with toxicity is that 4BRA binds very tightly to non-productive receptor(s) that protects it from proteinase K, while 4BL3PAT loses affinity to this non-productive receptor(s) but gains binding to a productive receptor that doesn't protect it against proteinase K. This model would predict that only 4BL3PAT enters the membrane while 4BRA remains on the surface bound tightly to the non-productive receptor(s).

Example 2

Cloning and Construction of a Trypsin-site Deletion Mutant of Cry19Aa:

Isolating cry19Aa gene construct: The cry19Aa [Genbank Accession Number: Y07603] construct (pJEG65.5), which contains both cry19Aa and orf2 in a shuttle vector, pH315, is maintained in *B. thuringiensis* SPL407. The plasmid DNA (pJEG65.5) was isolated from this host by total DNA extraction. Briefly, 0.2 ml of overnight-grown Bt cells that were cultured in brain heart infusion (BHI, Difco) medium at 37° C. were inoculated into 25 ml of BHI medium and incubated a further 2 hr in an incubator-shaker. Cells were centrifuged and washed with 10 ml of sterile distilled water twice at 6,000 rpm for 5 mm and the pellet was resuspended in 0.2 ml of autoplasting buffer (50 mM Sodium Acetate pH 7, 10% polyethylene glycol (w/v)) supplemented with 1 U of mutanolysin (Sigma). The suspension was incubated in a water bath at 37° C. for 30 min. Later, steps for purification of total DNA using High Pure PCR Template Prep kit (Roche) was according to the manufacturer.

Mutating cry19Aa by site-directed mutagenesis: Total DNA obtained from the above steps was used to transform competent DH5α E. coli cells by standard transformation protocol. Plasmid DNA (pJEG65.5) was purified using a plasmid purification kit (Qiagen). Site-directed mutagenesis was performed according to a modified QuickChange (Stratagene) method. The sequences of the mutagenic primers set for loop 1 were: Fw19L1 5'-ACC AAT TCT ATT TAT CAA GAC TTA AGA TTT TTA TCA GGT GGT C-3' (SEQ ID NO: 29) and Re19L1 5'-TGA TAA AAA TCT TAA GTC TTG ATA AAT AGA ATT GGT TAC AAA TC-3' (SEQ ID NO: 30). The sequences of the mutagenic primers set for loop 2 were: Fw19L2: 5'-AAT TAT GAA TAT ATT CCT GTA AAT ATT ACA AAA ATG AAT TTT TC-3' (SEQ ID NO: 31) and Re19L2 5'-ATT TAC AGG AAT ATA TTC ATA ATT TTC CGT CCA TAA ATT ATA TAC-3' (SEQ ID NO: 32). Briefly, 140 ng of DNA was mixed with 15 pmol of forward and reverse mutagenic primer, 500 μM (final concentration) of each deoxynucleotide triphosphate(dNTP mix, Roche), 0.5 U of Expand Long Template Polymerase (Roche), 1× Buffer 2 (Roche) in a total volume of 25 μl.

The programmed steps for the PCR reaction was as follows:

| Step | Reaction | Temperature | Duration |
|---|---|---|---|
| 1. | Initial Denaturation | 94° C. | 2 min |
| 2. | Denaturation | 94° C. | 10 s |
| 3. | Annealing | 48° C. | 30 s |
| 4. | Elongation | 68° C. | 4 min |
| 5. | Repeat steps 2-4 9 times | | |
| 6. | Denaturation | 94° C. | 15 s |
| 7. | Annealing | 48° C. | 30 s |
| 8. | Elongation | 68° C. | 4 min + 20 s every successive cycle |
| 9. | Repeat steps 6-8 15 times | | |
| 10. | Final elongation | 68° C. | 7 min |
| 11. | Cooling | 4° C. | unlimited |

The PCR thermal cycle machine used was MiniCycler (MJ Research). After the PCR was completed, the reaction product was digested with DpnI (Roche) to remove the naturally methylated template DNA. The digested PCR product was used to transform E. coli DH5α competent cells. Mutations were confirmed by automated DNA sequencing (Plant-Microbe Genomics Facility, the Ohio State University). Confirmed mutant DNA was transformed into crystal minus derivative of B. thuringiensis serotype H-14 (BGSC No. 4Q7) by electroporation as described previously for protein expression.

Isolating and purifying Cry19Aa toxins: A single Bt colony was inoculated into a 5 ml LB medium supplemented with 10 μg/ml erythromycin and grown overnight at 30° C. in an incubator-shaker at 250 rpm. This culture was inoculated into a 500 ml SSM medium also supplemented with erythromycin and incubated a further 4 days until sporulation and autolysis.

The culture was centrifuged in a JA-14 rotor at 9,000 rpm for 5 min at 4° C. The supernatant was discarded and the pellet was resuspended in 80 ml of crystal wash I. Next, the suspension was centrifuged and resuspended as before, twice. Later, the pellet from the last step was resuspended in crystal wash II (0.5 M NaCl). The suspension was centrifuged and resuspended as before, three times in this solution. Next, the pellet from the last step was resuspended in 80 ml of sterile ddH$_2$O and centrifuged as before. The pellet was resuspended in 2 ml of sterile ddH$_2$O and kept at 4° C. until needed. Crystal inclusion protein was solubilized in carbonate buffer (30 mM Na$_2$CO$_3$, 20 mM NaHCO$_3$, pH 10.0) and protein concentration was measured using the Coomassie protein assay reagent (Pierce) with bovine serum albumin as standard. For binding assays, purification of toxin was performed as follows. Solubilized toxin was centrifuged in a JA-17 rotor at 16,000 rpm for 10 min to separate the spores. The activated toxin was purified by HPLC using a Superdex 200 (Pharmacia) column.

Proteinase K protection assay for Cry19Aa toxins: In this assay, 5 μg of Ae. aegypti BBMV was incubated with either 10 nM of $^{125}$I-labeled Cry19Aa or 19AL1L2 in 0.1 ml of binding buffer for 1 hr at room temperature. Later, 10 μg of proteinase K (Roche) was added and incubated a further 20 min. The action of the protease was stopped by 100 μg pefabloc sc (Roche). The reaction was centrifuged at 15,000 rpm for 10 min at room temperature to separate the remaining toxin bound/inserted in the BBMV. The pellet was washed two times with binding buffer without resuspending the pellet. The resulting data was obtained as mentioned above.

Mosquito bioassay of Cry19Aa and its mutein: In loop 1 of Cry19Aa, 355SYWT358 (SEQ ID NO: 42) was mutated to YQDL (SEQ ID NO: 33) and an R was inserted immediately after position 358, while in loop 2, 414YPWGD418 (SEQ ID NO: 43) was deleted. These mutations, according to the model structures, mimicked the residues in loop 1 and the length of loop 2 of Cry4Ba. This mutant was called 19AL1L2. Bioassays on 2$^{nd}$ instars mosquito larvae were done to test the mosquitocidal activities of the wild-type Cry19Aa and the mutein. The results in Table 5 indicate that the mutations enhanced the Cry19Aa Ae. aegypti activity by 42,000-fold. This enhancement was achieved without deteriorating the Anopheles and Culex activity of the toxin. However, initial experiments indicated that loop 1 or loop 2 exchange alone did not produce toxicity against Ae. aegypti.

TABLE 5

Bioassay results of four species of mosquitoes.

($LC_{50}$ in ng/ml)‡

| Toxins | An. quadrimaculatus | Ae. aegypti | Cx. quinquefasciatus | Cx. pipiens |
|---|---|---|---|---|
| Cry19Aa | 3.0 (2.0-4.4) | 1.4 (0.4-103) × 10$^5$ | 35 (22-52) | 6 (3-9) |
| 19AL1L2 | 2.2 (2.2-2.3) | 3.3 (3.1-3.5) | 19 (11-32) | 5 (1-10) |

‡2-day old larvae of Ae. aegypti, Cx. quinquefasciatus and Cx. pipiens; 3-day old larvae of An. quadrimaculatus were used for bioassays. Mortality was recorded after 24 hours exposure to a serial dilution of the toxins. The 95% confidence limit is indicated in parentheses. Bioassays used ICPs and spores purified from B. thuringiensis.

Binding assays: The ability of the inactive and active toxin to reversibly bind to the BBMV of Ae. aegypti was tested in the binding assay of Cry19Aa and 19AL1L2. The results (FIG. 13) indicated that there was no significant difference in the ability to reversibly bind the BBMV for both the least-active Cry19Aa and the active 19AL1L2. There was also no significant difference in the ability of the toxins to irreversibly bind to the BBMV as shown in FIG. 14. These results suggested that the enhanced *Aedes* activity of the Cry19Aa mutant was not correlated with receptor binding and membrane insertion. The proteinase K protection assay result shown in FIG. 15 indicated that there was less amount of 19AL1L2 than Cry19Aa toxin inserted into the membrane of the *Ae. aegypti* BBMV and thus was protected from protease degradation. This result is similar to the results obtained for 4BRA and 4BL3PAT above, where there was a negative correlation between toxicity and the amount of toxin protected from proteinase K.

Conclusions: Mutations in loop 1 of Cry19Aa, involved substitution of 355SYWT358 (SEQ ID NO: 42) with YQDL (SEQ ID NO: 33) and an R was inserted immediately after position 358. Mutations in loop 2 involved deletion of 414YPWGD418 (SEQ ID NO: 43). Bioassays on $2^{nd}$ instars mosquito larvae indicated that the mutations enhanced the Cry19Aa *Ae. aegypti* activity by 42,000 folds, and it was attained without disrupting the *Anopheles* and *Culex* activity of the toxin.

The trypsin processing of Cry19Aa and 19AL1L2 showed similar pattern as shown in FIG. 16. However, the protoxin forms of Cry19Aa and 19AL1L2 indicated that the mutations made in loop 1 and loop 2 might have destabilized 19AL1L2 as indicated by a distinct band at 39 kDa. This instability did not deteriorate its toxicity towards the tested mosquitoes. Gel filtration by HPLC of the trypsinated toxins indicated that the toxins had a molecular size of 66 kDa (data not shown). This suggests that the toxins, although digested by trypsin, were structurally intact in non-denaturing condition.

Example 3

Enhancing Cry4ba Toxicity by Mutations in Domain III

A computational protein-protein docking between CPM1 (a Bin toxin receptor in *Cx. pipiens*) and 4BL3PAT (an enhanced-mutant of Cry4Ba that is toxic against *Culex* larvae) was performed to search for potential interaction sites on the toxin to be modified to enhance *Culex* toxicity. A putative domain III loop was identified (578-NNII-581) (SEQ ID NO: 34) and mutated. Bioassay results suggest that the residues in the loop have minor effect on *Aedes* toxicity. However, two of the mutations (N579A and I580A) caused decreased expression or structural instability, and were not toxic to *Aedes, Anopheles,* and *Culex* larvae. A mutation in Cry4Ba (I578Y, the same residue as I580 in 4BL3PAT) caused a slight increase in toxicity against *Cx. pipiens*. However, no significant increase in *Culex* toxicity was observed in I580Y mutation in 4BL3PAT. The initial aim of enhancing *Culex* toxicity in 4BL3PAT was not achieved, however, *Anopheles* toxicity was enhanced significantly up to 40-fold.

Homology modeling Three main programs were used to model the structure of Cry4Ba: i) An internet-based CLUSTAL W version (16) available online; ii) SWISS-MODEL available online; iii) Swiss-Pdb Viewer Version 3.7b2 (4, 12, 13). All of these programs are freely accessible and are quite simple to operate. CLUSTAL W was used to align the protein sequence of the target protein with the template of known tertiary structure. Models were constructed using the "Optimize (project) mode" in SWISS-MODEL, in conjunction with Swiss-Pdb Viewer. The sequence of the target protein was aligned with the template sequence in Swiss-Pdb Viewer according to the alignment produced by CLUSTAL W earlier. Unaligned residues at the N and C terminal of the target protein were removed prior to submitting the project to the SWISS-MODEL site. A model structure for CPM 1 was obtained using the 3D-PSSM internet server (available online). The template for homology modeling was *B. cereus* oligo- 1,6-glucosidase, which has 32% sequence identity with CPM 1.

Mutating Cry toxins by site-directed mutagenesis Site-directed mutagenesis was performed using the modified QuickChange (Stratagene) method. DNA templates were purified using a plasmid purification kit (Qiagen). Purified templates (3 µg) were methylated using 8 U of dam methylase (New England Biolabs) for 15 min at 37° C. The reaction was stopped on ice. For polymerase chain reaction (PCR), 100 to 200 ng of methylated DNA was mixed with 15 pmol of forward and reverse mutagenic primer, 300 µM (final concentration) of each deoxynucleotide triphosphate (dNTP mix, Roche), 0.5 U of Expand Long Template Polymerase (Roche), 1× Buffer I (Roche) in a total volume of 25 µl. The sequences of the primers are listed in Table 6. Each of the forward primer (primer names start with an Fw) was paired with a common reverse primer, RePATD3, for each mutation.

Table 6. Sequences of primers (SEQ ID NOS 35-41) used in site directed mutagenesis.

TABLE 6

Sequences of primers (SEQ ID NOS 35-41) used in site-directed mutagenesis.

| Primer | Sequence (5' → 3') |
|---|---|
| FwPATN578A | CGT TTT CAA GAC CTG CTA ATA TAA TAC CTA CAG |
| FwPATN579A | CGT TTT CAA GAC CTA ATG CTA TAA TAC CTA CAG ATT TAA AAT ATG |
| FwPATI580A | CGT TTT CAA GAC CTA ATA ATG CAA TAC CTA CAG ATT TAA AAT ATG |
| FwPATI581A | CGT TTT CAA GAC CTA ATA ATA TAG CAC CTA CAG ATT TAA AAT ATG |
| FwPATI580F | CGT TTT CAA GAC CTA ATA ATT TTA TAC CTA CAG ATT TAA AAT ATG |
| FwPATI581F | CGT TTT CAA GAC CTA ATA ATA TAT TTC CTA CAG ATT TAA AAT ATG |
| RePATD3 | AGG TCT TGA AAA CGT AGA TTC TGT ACT AAT CGT TG |

The programmed steps for the PCR reaction were as follows:

| Step | Reaction | Temperature | Duration |
|---|---|---|---|
| 1. | Initial Denaturation | 94° C. | 2 min |
| 2. | Denaturation | 94° C. | 10 s |
| 3. | Annealing | 48° C. | 30 s |
| 4. | Elongation | 68° C. | 4 min |
| 5. | Repeat steps 2-4 9 times | | |
| 6. | Denaturation | 94° C. | 15 s |
| 7. | Annealing | 48° C. | 30 s |
| 8. | Elongation | 68° C. | 4 min + 20 s every successive cycle |
| 9. | Repeat steps 6-8 15 times | | |
| 10. | Final elongation | 68° C. | 7 min |
| 11. | Cooling | 4° C. | unlimited |

The PCR thermal cycle machine used was MiniCycler (MJ Research). After the PCR was completed, the reaction product was digested with DpnI (Roche) to remove the methylated template DNA. The digested PCR product was used to transform *E. coli* DH5α competent cells. Mutations were confirmed by automated DNA sequencing (Plant-Microbe Genomics Facility, The Ohio State University).

Isolating and purifying Cry toxin *E. coli* cells containing the toxin construct were grown on Luria Bertani (LB) agar plates (11) supplemented with 100 μg/ml of ampicillin at 37° C. A single colony was inoculated into 5 ml of LB broth and incubated overnight at 37° C. in an incubator-shaker at 250 rpm. A 2 ml overnight culture was inoculated into 500 ml of modified Terrific Broth (24 g/L yeast extract, 12 g/L tryptone, 2% glycerol, 25.08 g/L $K_2HPO_4$, 4.62 g/L $KH_2PO_4$), supplemented with 100 μg/ml ampicillin, and grown for 72 h at 37° C. in an incubator-shaker at 250 rpm.

Cells were harvested by centrifugation at 9,820×g for 10 min at 15° C. with a JA-14 rotor in an Avanti J-25 centrifuge (Beckman). The supernatant was discarded and the pellet was resuspended in 50 ml of lysis buffer (50 mM Tris, 50 mM EDTA, 15% sucrose, pH 8.0), supplemented with 20 mg of lysozyme. The suspension was incubated at 37° C. for 3 h in an incubator-shaker shaking at 250 rpm. Subsequently, the suspension was centrifuged in a JA-14 rotor at 15,344×g for 10 min at 4° C. The resulting thick supernatant was discarded carefully with attention paid towards not losing the loose pellet. The pellet was resuspended in 80 ml of crystal wash I (2% Triton X-100, 0.5 M NaCl) and was cooled on ice for 10-15 min prior to sonication (1:30 min, 5 s burst, 50% duty, ½" tip, no. 8 on output control) on ice, using a W-385 sonicator (Heat Systems Ultrasonics, Inc). The suspension was cooled on ice for 5 min and later shaken by hand in a centrifuge bottle for about 30 s. The suspension was centrifuged in a JA-14 rotor at 12,429×g for 5 min at 4° C. The supernatant was discarded and the pellet was resuspended in 80 ml of crystal wash I. Next, the suspension was centrifuged and resuspended as before, twice. Later, the pellet from the last step was resuspended in crystal wash II (0.5 M NaCl). The suspension was centrifuged and resuspended as before, three times in this solution. Next, the pellet from the last step was resuspended in 80 ml of sterile deionized distilled water ($ddH_2O$) and centrifuged as before. The pellet was resuspended in 2 ml of sterile $ddH_2O$ and kept at 4° C. until needed. Crystal inclusion protein was solubilized in carbonate buffer (30 mM $Na_2CO_3$, 20 mM $NaHCO_3$, pH 10.0) and protein concentration was measured using the Coomassie protein assay reagent (Pierce) with bovine serum albumin as standard. For binding assays, solubilized toxin was incubated with 1/20 (v/v) 10 mg/ml trypsin (Sigma) at 37° C. for 3 h. The activated toxin was purified by HPLC using a Superdex 200 (Pharmacia) column.

Determining toxicity of Cry toxins by mosquito larvae bioassay Colonies of the mosquitoes were reared in an environment-controlled room at 28° C. and 85% humidity, with a photoperiod of 14-h light/10-h dark. The *An. quadrimaculatus* culture was a kind gift from Peggy Hodges (University of Notre Dame), *Ae. aegypti* from Allan Yousten (Virginia Polytechnic Institute), and *Cx. pipiens* (recently isolated from nature in Ohio) from Rebecca Moll and Woodbridge Foster (Ohio State University). Adult mosquitoes were maintained on heparinated cow blood, sugar cane cubes (Domino Dots) and dechlorinated tap water. *Aedes* and *Culex* larvae were maintained on fish food pellets (Koi Floating Blend, Aquaricare™), while *Anopheles* larvae were maintained on 2:1 ratio of ground fish food flakes (Vitapro™ Plus Cichlid Power Flakes, Mike Reed Enterprises) and brewers yeast, as suggested by Mark Q. Benedict (Centers for Disease Control and Prevention). Second instar larvae were used for all bioassays. Bioassays were performed on different days after hatching due to the different growth rate of the mosquito larvae. *Ae. aegypti* and *Cx. pipiens* larvae were tested two days after hatching, while *An. quadrimaculatus* larvae were tested three days after hatching. A total of six larvae per 2.5 ml of water with one replicate in a 24 well Costar™ cell culture plate (Corning) were fed a serial dilution of Cry toxins and the number of mortalities was counted after a 24-hour incubation at 30° C. The bioassay was repeated to obtain a reasonable lethal concentration range, where applicable, and the $LC_{50}$ was calculated by a Probit method using SoftTOX™ ver. 1.1 (WindowChem™).

Preparing mosquito brush border membrane vesicles (BBMV) Fourth instar mosquito larvae were filtered with a nylon mesh, washed in distilled water, separated from large residual food particles, and dried briefly on a filter paper (Fisher) under vacuum suction. Harvested larvae were frozen at −70° C. until needed. About 4-6 g of frozen larvae were homogenized in 8-12 ml of cold buffer A (300 mM mannitol, 5 mM EGTA, 17 mM Tris-HCl, pH 7.5). Larvae were homogenized by 40 strokes of Potter-Elvehjem PTFE pestle in glass tube at speed number 5 (~6000 rpm). The homogenized sample was centrifuged at 11,159×g for 5 min at 4° C. in a JA-17 rotor. The pellet was discarded while the supernatant was kept for the next step. The supernatant was filtered through a Whatman (No. 1) filter paper under vacuum and the filtrate was collected on ice. Tubes containing continuous sucrose gradient were prepared by mixing 15 ml of $ddH_2O$ with 15 ml of 45% Sucrose (w/v in $ddH_2O$) in a gradient maker. A 4 ml filtrate prepared previously was layered carefully on top of the gradient with a 10 ml glass pipette. The tubes were centrifuged at 15,000 rpm for 2 h at 4° C. in an SW28 rotor. After the centrifugation, the top layer was removed by suction and discarded, leaving the lowest visible layer or the pellet. This layer was transferred to a new tube, resuspended in cold sterile $ddH_2O$, and centrifuged at 35,267×g for 15 min at 4° C. in a JA-17 rotor. The supernatant was discarded and any loose pellet was rinsed off with binding buffer (60 mM $K_2HPO_4$, 5 mM $KH_2PO_4$, 150 mM NaCl, 10 mM EGTA, pH 7.00). The BBMV pellet was resuspended in 1 ml of ice-cold Binding Buffer supplemented with COMPLETE™ (Roche) protease inhibitor and homogenized by 10 extrusions using a small Teflon pestle. The protein concentration of the BBMV was measured with the Coomassie protein assay reagent (Pierce), using BSA as the standard. The BBMV was distributed into 0.5 ml aliquots and kept at −70° C. until needed. The activity of aminopeptidase N (a brush border membrane marker) was tested at each step of an *Anopheles* BBMV preparation. There was a 5.5-fold enrichment of aminopeptidase N compared to the larval homogenate, which suggested that this was an acceptable method for preparing BBMV.

Radioactive labeling of Cry toxins Activated toxins were iodinated as previously described (19). Briefly, 0.3 to 0.5 mCi of Na $^{125}$I (Perkin Elmer) from the stock vial was incubated with one iodo-bead (Pierce) for 5 min at room temperature. Later, an HPLC-purified toxin in carbonate buffer (30 mM $Na_2CO_3$, 20 mM $NaHCO_3$, pH 10.0) (45 µg in 0.1 ml carbonate buffer) was added to the bead and was incubated a further 5 min. The reaction mix was removed from the iodo-bead and was applied to a 2-ml Excellulose column (Pierce) to remove free iodine from the toxin.

Reversible binding assay The course of toxin binding to BBMV was suggested to occur through a two-step process involving reversible (5, 6) and irreversible steps (7, 14, 18). In this assay, 10 µg of mosquito BBMV were incubated with 1 nM of $^{125}$I-labeled 4BRA in 0.1 ml of binding buffer with increasing amount of unlabeled toxin for a period of 1 h at room temperature. The reaction was centrifuged at 27,000×g for 10 min to separate unbound labeled toxin from the BBMV. The supernatant was discarded while the pellet was washed twice with binding buffer. The resulting pellet was counted in a gamma counter (Wallac) and the data were plotted with SigmaPlot ver. 8.0 (SPSS, Inc.). The experiment was repeated with different unlabeled toxin as competitors.

Protein-protein Docking A program for protein docking called GRAMM was used to achieve this purpose. The protein docking used the high-resolution generic setting for hydrophobic docking. The hydrophobic docking was reported to yield markedly higher signal-to-noise ratio so that the correct match is discriminated better from false positive fits (17). Docking was performed using the model structures of CPM1 and 4BL3PAT. Ten highest scoring complex based on the lowest-energy matches were scrutinized based on the close association of domain II loop 3 of 4BL3PAT to CPM1. One complex that matched the criteria also showed association of a domain III loop region (residues 578-581) with CPM1 (FIG. 17). This suggested that the loop region could be a potential site for modification to enhance *Culex* toxicity.

Conclusions The bioassay results shown in Table 7 indicated that 4BRA-I578Y was slightly enhanced in *Culex* activity, however, *Aedes* activity was decreased by 4-fold. *Anopheles* activity was enhanced but not significantly. These results demonstrated the importance of the 4BRA domain III loop in mosquitocidal activity in general and in *Culex* toxicity specifically. Based on this discovery, further mutations were made in another construct, 4BL3PAT, in the same loop region to enhance *Culex* toxicity. An alanine scanning of the loop (578NNII581)(SEQ ID NO: 34) and also mutations of each Ile (I580 and I581) to Phe were performed.

TABLE 7

Bioassay results of 3 species of mosquitoes comparing the effect of domain III loop mutations.

| Toxins | ($LC_{50}$ in ng/ml)‡ | | |
|---|---|---|---|
| | *An. quadrimaculatus* | *Ae. aegypti* | *Cx. pipiens* |
| 4BRA | 21 (15-29) | 21 (5-51) | >20,000 |
| 4BRA-I578Y | 12 (8-23) | 85 (57-140) | 25% at 2000 |
| 4BL3PAT | 44 (40-50) | 53 (19-91) | 95 (69-130) |
| 4BL3PAT-N578A | 4 (1-6) | 65 (38-96) | ND |
| 4BL3PAT-N579A | Toxin was not stable | | |
| 4BL3PAT-I580A | Toxin was not stable | | |
| 4BL3PAT-I580F | 4 (3-5) | 35 (2-82) | 397$^a$ |
| 4BL3PAT-I580Y | 5 (1-10) | 26 (11-36) | 155 (25-421) |
| 4BL3PAT-I581A | 2 (0-5) | 18 (11-27) | 99 (23-169) |
| 4BL3PAT-I581F | 1 (0-5)$^b$ | 18 (10-27) | 81 (29-149) |

‡2-day old larvae of *Ae. aegypti*, and *Cx. pipiens*, and 3-day old larvae of *An. quadrimaculatus* were used for bioassays. Mortality was recorded after 24 hours exposure to a serial dilution of the toxins. The 95% confidence limit is indicated in parentheses. Bioassays for the cry4B constructs used purified inclusion crystal protein (ICP) produced in *E. coli*.
$^a$confidence limit was too large
$^b$*Anopheles* toxicity enhanced about 20-fold relative to 4BRA and about 40-fold relative to 4BL3PAT
ND Not determined The results in Table 7 show that the mutations were mostly enhancing *Anopheles* activity. *Aedes* activity was also enhanced relative to 4BL3PAT but not significantly relative to 4BRA. This result was in contrast to earlier bioassay using 4BRA-I578Y (position I578 in 4BRA is similar to position I580 in 4BL3PAT) where toxicity against *Aedes* was reduced significantly. *Culex* activity was not significantly affected by the mutations in I580 and I581. However, the mutations, N579A and I580A, caused toxin yield to decrease significantly as well as their toxicity (data not shown), perhaps due to structural instability. I580Y or I580F mutation in 4BL3PAT seemed to have deleterious effect on *Culex* activity, in contrast to the results of 4BRA-I578Y. On the other hand, I581A and I581F both have enhanced activity against *Anopheles*, which was intriguing since Ala and Phe are very different in terms of hydrophobicity and size. So, although the initial objective was to enhance the toxicity against *Culex*, we have instead, enhanced toxicity against *Anopheles* by about 20-fold relative to 4BRA and about 40-fold relative to 4BL3PAT.

Competition binding assays were performed and the results show that N578A mutant was competing for similar binding sites on *An. quadrimaculatus* BBMV as 4BRA (FIG. 18). However, I580F, I581A, and I581F show significantly different competition pattern. The I580F and I581F mutants were less able to compete with 4BRA compared to I581A. This suggests that the binding affinity I580F and I581F mutants to 4BRA receptors on the BBMV were reduced. The I580F mutant appears to have completely lost its ability to compete with 4BRA. However, initial saturation binding assay suggest that the mutant was able to bind to the BBMV with high affinity (data not shown), suggesting that the loss of competition binding to 4BRA was not due to inability to bind the BBMV. The increase in toxicity could also be due to other factors besides its reversible binding affinities. Other factors such as pore forming, oligomerization, and membrane insertion abilities have been demonstrated to affect toxicity.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the appended claims, which should be construed as broadly as the prior art will permit.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated insecticidal *Bacillus thuringiensis* Cry4Ba protein that has the sequence SEQ ID NO: 1 that is modified by substitution of the amino acid aspartic acid at position 454 with proline, glycine, alanine, threonine or serine; and insertion of two additional amino acids immediately after position 454, wherein the additional amino acids are chosen from the group consisting of: glycine, alanine, valine, leucine, isoleucine, methionine, proline, threonine, and serine and wherein the modified Cry4Ba protein exhibits enhanced toxicity to *Culex* as compared to Cry4Ba protein that has the sequence SEQ ID NO: 1.

2. The isolated insecticidal *Bacillus thuringiensis* Cry4Ba protein according to claim 1, wherein the first additional amino acid inserted after position 454 is glycine or alanine.

3. The isolated insecticidal *Bacillus thuringiensis* Cry4Ba protein according to claim 1, wherein the substitution at position 454 is with proline, glycine, or alanine.

4. The isolated insecticidal *Bacillus thuringiensis* Cry4Ba protein according to claim 1, wherein the substitution at position 454 is with proline, glycine, or alanine, and the first additional amino acid inserted immediately after position 454 is glycine or alanine.

5. The isolated insecticidal *Bacillus thuringiensis* Cry4Ba protein according to claim 1, wherein the substitution at position 454 is with proline, glycine, or alanine, the first additional amino acid inserted immediately after position 454 is glycine or alanine, and the second additional amino acid inserted immediately after position 454 is chosen from the group consisting of glycine, alanine, valine, leucine, isoleucine, methionine, proline, threonine, and serine.

6. The isolated insecticidal *Bacillus thuringiensis* Cry4Ba protein according to claim 1, wherein the aspartic acid at position 454 is substituted with proline, glycine, or alanine, and the two additional amino acids inserted immediately after the substitution are selected from the combinations of alanine and threonine, alanine and valine, and alanine and alanine.

7. The isolated insecticidal *Bacillus thuringiensis* Cry4Ba protein according to claim 1, wherein the modifications are selected from the group consisting of:

(a) substitution at amino acid position 454 with proline, and insertion of the amino acids alanine and threonine after amino acid position 454;

(b) substitution at amino acid position 454 with glycine, and insertion of the amino acids alanine and valine after amino acid position 454;

(c) substitution at amino acid position 454 with alanine, and insertion of the amino acids alanine and threonine after amino acid position 454;

(d) substitution at amino acid position 454 with proline, and insertion of the amino acids alanine and alanine after amino acid position 454;

(e) substitution at amino acid position 454 with alanine, and insertion of the amino acids alanine and alanine after amino acid position 454; and (f) substitution at amino acid position 454 with glycine, and insertion of the amino acids alanine and threonine after amino acid position 454.

8. The isolated insecticidal *Bacillus thuringiensis* Cry4Ba protein according to claim 6, wherein the aspartic acid at position 454 is substituted with proline and the second additional amino acid inserted immediately after position 454 is threonine or valine.

9. The isolated insecticidal *Bacillus thuringiensis* Cry4Ba protein according to claim 6, wherein, the aspartic acid at position 454 is substituted with glycine and the second additional amino acid inserted immediately after position 454 is threonine or valine.

10. An isolated insecticidal *Bacillus thuringiensis* Cry4Ba protein that has the sequence SEQ ID NO: 1 that is modified by one or more amino acid substitution at position 578, 580, or 581 with an amino acid selected from the group consisting of alanine, glycine, phenylalanine, tyrosine, tryptophan, threonine and serine, and wherein the modified Cry4Ba protein has enhanced toxicity against *Anopheles* or *Aedes* or both as compared to Cry4Ba protein that has the sequence SEQ ID NO: 1.

11. The isolated insecticidal *Bacillus thuringiensis* Cry4Ba protein according to claim 10, wherein the one or more amino acid substitutions are: the amino acid at position 578 is replaced with alanine; the amino acid at position 580 is replaced with phenylalanine or tyrosine; or the amino acid at position 581 is replaced with alanine or phenylalanine.

12. An isolated insecticidal *Bacillus thuringiensis* Cry4Ba protein that has the sequence SEQ ID NO: 1 that is modified by one or more amino acid substitutions at position 578, 580, or 581, wherein the one or more amino acid substitutions are: the amino acid at position 578 is replaced with alanine; the amino acid at position 580 is replaced with phenylalanine or tyrosine; or the amino acid at position 581 is replaced with alanine or phenylalanine, and further modified by substitution of aspartic acid at position 454 with proline, and the insertion of amino acids alanine and threonine immediately after position 454, and wherein the modified Cry4Ba protein has enhanced toxicity against *Anopheles* or *Aedes* or both as compared to Cry4Ba protein that has the sequence SEQ ID NO: 1.

13. An isolated nucleic acid molecule encoding a modified Cry4Ba protein that has the sequence SEQ ID NO: 1 that is modified by substitution of the amino acid aspartic acid at position 454 with proline, glycine, alanine, threonine or serine; and insertion of two additional amino acids immediately after position 454, wherein the additional amino acids are chosen from the group consisting of: glycine, alanine, valine, leucine, isoleucine, methionine, proline, threonine, and serine, and wherein the modified Cry4Ba protein exhibits enhanced toxicity to *Culex* as compared to Cry4Ba protein that has the sequence SEQ ID NO: 1.

14. A vector comprising an isolated nucleic acid molecule encoding a modified Cry4Ba protein, wherein the modified Cry4Ba protein has the sequence SEQ ID NO: 1 that is modified by substitution of the amino acid aspartic acid at position 454 with proline, glycine, alanine, threonine or serine; and insertion of two additional amino acids immediately after position 454, wherein the additional amino acids are chosen from the group consisting of: glycine, alanine, valine, leucine, isoleucine, methionine, proline, threonine, and serine, and wherein the modified Cry4Ba protein exhibits enhanced toxicity to *Culex* as compared to Cry4Ba protein that has the sequence SEQ ID NO: 1.

15. A host cell comprising an isolated nucleic acid molecule encoding a modified Cry4Ba protein, wherein the modified Cry4Ba protein has the sequence SEQ ID NO: 1 that is modified by substitution of the amino acid aspartic acid at position 454 with proline, glycine, alanine, threonine or serine; and insertion of two additional amino acids immediately after position 454, wherein the additional amino acids are chosen from the group consisting of: glycine, alanine, valine, leucine, isoleucine, methionine, proline, threonine, and serine, and wherein the modified Cry4Ba protein exhibits enhanced toxicity to *Culex* as compared to Cry4Ba protein that has the sequence SEQ ID NO 1.

16. A method for reducing populations of target mosquitoes that are vectors of disease, by delivering into a habitat of the target mosquitoes one or more isolated Cry4Ba proteins according to claim 7 as an insecticidal agent.

17. Insecticidal compositions comprising mutant toxins including one or more modified Cry4Ba proteins, and an agriculturally acceptable carrier, diluent and/or excipient, wherein the modified Cry4Ba protein has the sequence SEQ ID NO: 1 that is modified by substitution of the amino acid aspartic acid at position 454 with proline, glycine, alanine, threonine or serine; and insertion of two additional amino acids immediately after position 454, wherein the additional amino acids are chosen from the group consisting of: glycine, alanine, valine, leucine, isoleucine, methionine, proline, threonine, and serine, and wherein the modified Cry4Ba protein exhibits enhanced toxicity to *Culex* as compared to Cry4Ba protein that has the sequence SEQ ID NO: 1.

18. The nucleic acid of claim 13, wherein the modified insecticidal *Bacillus thuringiensis* Cry4Ba protein has a modification selected from the group consisting of:
(a) substitution at amino acid position 454 with proline, and insertion of the amino acids alanine and threonine immediately after amino acid position 454;
(b) substitution at amino acid position 454 with glycine, and insertion of the amino acids alanine and valine immediately after amino acid position 454;
(c) substitution at amino acid position 454 with alanine, and insertion of the amino acids alanine and threonine immediately after amino acid position 454;
(d) substitution at amino acid position 454 with proline, and insertion of the amino acids alanine and alanine immediately after amino acid position 454;
(e) substitution at amino acid position 454 with alanine, and insertion of the amino acids alanine and alanine immediately after amino acid position 454; and
(f) substitution at amino acid position 454 with glycine, and insertion of the amino acids alanine and threonine immediately after amino acid position 454.

19. The vector of claim 14, wherein the modified Cry4Ba protein has a modification selected from the group consisting of:
(a) substitution at amino acid position 454 with proline, and insertion of the amino acids alanine and threonine immediately after amino acid position 454;
(b) substitution at amino acid position 454 with glycine, and insertion of the amino acids alanine and valine immediately after amino acid position 454;
(c) substitution at amino acid position 454 with alanine, and insertion of the amino acids alanine and threonine immediately after amino acid position 454;
(d) substitution at amino acid position 454 with proline, and insertion of the amino acids alanine and alanine immediately after amino acid position 454;
(e) substitution at amino acid position 454 with alanine, and insertion of the amino acids alanine and alanine immediately after amino acid position 454; and
(f) substitution at amino acid position 454 with glycine, and insertion of the amino acids alanine and threonine immediately after amino acid position 454.

20. The host cell of claim 15, wherein the modified Cry4Ba protein has a modification selected from the group consisting of:
(a) substitution at amino acid position 454 with proline, and insertion of the amino acids alanine and threonine immediately after amino acid position 454;
(b) substitution at amino acid position 454 with glycine, and insertion of the amino acids alanine and valine immediately after amino acid position 454;
(c) substitution at amino acid position 454 with alanine, and insertion of the amino acids alanine and threonine immediately after amino acid position 454;
(d) substitution at amino acid position 454 with proline, and insertion of the amino acids alanine and alanine immediately after amino acid position 454;

(e) substitution at amino acid position 454 with alanine, and insertion of the amino acids alanine and alanine immediately after amino acid position 454; and (f) substitution at amino acid position 454 with glycine, and insertion of the amino acids alanine and threonine immediately after amino acid position 454.

21. The insecticidal composition of claim 17, wherein the modified Cry4Ba protein has a modification selected from the group consisting of: (a) substitution at amino acid position 454 with proline, and insertion of the amino acids alanine and threonine immediately after amino acid position 454; (b) substitution at amino acid position 454 with glycine, and insertion of the amino acids alanine and valine immediately after amino acid position 454; (c) substitution at amino acid position 454 with alanine, and insertion of the amino acids alanine and threonine immediately after amino acid position 454; (d) substitution at amino acid position 454 with proline, and insertion of the amino acids alanine and alanine immediately after amino acid position 454; (e) substitution at amino acid position 454 with alanine, and insertion of the amino acids alanine and alanine immediately after amino acid position 454; and (f) substitution at amino acid position 454 with glycine, and insertion of the amino acids alanine and threonine immediately after amino acid position 454.

22. An isolated nucleic acid molecule encoding a modified *Bacillus thuringiensis* Cry4Ba protein that has the sequence SEQ ID NO: 1 that is modified by one or more amino acid substitutions at position 578, 580, or 581 with an amino acid selected from the group consisting of: alanine, glycine, phenylalanine, tyrosine, tryptophan, threonine and serine, and wherein the modified Cry4Ba protein exhibits enhanced toxicity to *Anopheles* or *Aedes* or both as compared to Cry4Ba protein that has the sequence SEQ ID NO: 1.

23. The nucleic acid molecule according to claim 22, wherein the modified Cry4Ba protein comprises one or more of the following amino acid substitutions: the amino acid at position 578 is replaced with alanine; the amino acid at position 580 is replaced with phenylalanine or tyrosine; or the amino acid at position 581 is replaced with alanine or phenylalanine.

24. A vector comprising an isolated nucleic acid molecule encoding a modified *Bacillus thuringiensis* Cry4Ba protein that has the sequence SEQ ID NO: 1 that is modified by one or more amino acid substitutions at position 578, 580, or 581 with an amino acid selected from the group consisting of: alanine, glycine, phenylalanine, tyrosine, tryptophan, threonine and serine, and wherein the modified Cry4Ba protein exhibits enhanced toxicity to *Anopheles* or *Aedes* or both as compared to Cry4Ba protein that has the sequence SEQ ID NO: 1.

25. The vector according to claim 24, wherein the modified Cry4Ba protein comprises one or more of the following amino acid substitutions: the amino acid at position 578 is replaced with alanine; the amino acid at position 580 is replaced with phenylalanine or tyrosine; or the amino acid at position 581 is replaced with alanine or phenylalanine.

26. A host cell comprising an isolated nucleic acid molecule encoding a modified *Bacillus thuringiensis* Cry4Ba protein that has the sequence SEQ ID NO: 1 that is modified by one or more amino acid substitutions at position 578, 580, or 581 with an amino acid selected from the group consisting of: alanine, glycine, phenylalanine, tyrosine, tryptophan, threonine and seine, and wherein the modified Cry4Ba protein exhibits enhanced toxicity to *Anopheles* or *Aedes* or both as compared to Cry4Ba protein that has the sequence SEQ ID NO: 1.

27. The host cell according to claim 26, wherein the modified Cry4Ba protein comprises one or more of the following amino acid substitutions: the amino acid at position 578 is replaced with alanine; the amino acid at position 580 is replaced with phenylalanine or tyrosine; or the amino acid at position 581 is replaced with alanine or phenylalanine.

28. An insecticidal composition comprising one or more *Bacillus thuringiensis* modified Cry4Ba proteins and an agriculturally acceptable carrier, diluent and/or excipient, wherein the modified Cry4Ba protein has the sequence SEQ ID NO: 1 that is modified by one or more amino acid substitutions at position 578, 580, or 581 with an amino acid selected from the group consisting of: alanine, glycine, phenylalanine, tyrosine, tryptophan, threonine and serine, and wherein the modified Cry4Ba protein exhibits enhanced toxicity to *Anopheles* or *Aedes* or both as compared to Cry4Ba protein that has the sequence SEQ ID NO: 1.

29. The insecticidal composition of claim 28, wherein the modified Cry4Ba protein comprises one or more of the following amino acid substitutions: the amino acid at position 578 is replaced with alanine; the amino acid at position 580 is replaced with phenylalanine or tyrosine; or the amino acid at position 581 is replaced with alanine or phenylalanine.

* * * * *

```
                          SEQUENCE LISTING

<160> NUMBER OF SEQ ID NOS: 43

<210> SEQ ID NO 1
<211> LENGTH: 1136
<212> TYPE: PRT
<213> ORGANISM: Bacillus thuringiensis

<400> SEQUENCE: 1

Met Asn Ser Gly Tyr Pro Leu Ala Asn Asp Leu Gln Gly Ser Met Lys
  1               5                  10                  15

Asn Thr Asn Tyr Lys Asp Trp Leu Ala Met Cys Glu Asn Asn Gln Gln
             20                  25                  30

Tyr Gly Val Asn Pro Ala Ala Ile Asn Ser Ser Ser Val Ser Thr Ala
         35                  40                  45

Leu Lys Val Ala Gly Ala Ile Leu Lys Phe Val Asn Pro Pro Ala Gly
     50                  55                  60

Thr Val Leu Thr Val Leu Ser Ala Val Leu Pro Ile Leu Trp Pro Thr
 65                  70                  75                  80

Asn Thr Pro Thr Pro Glu Arg Val Trp Asn Asp Phe Met Thr Asn Thr
                 85                  90                  95

Gly Asn Leu Ile Asp Gln Thr Val Thr Ala Tyr Val Arg Thr Asp Ala
            100                 105                 110

Asn Ala Lys Met Thr Val Val Lys Asp Tyr Leu Asp Gln Tyr Thr Thr
        115                 120                 125

Lys Phe Asn Thr Trp Lys Arg Glu Pro Asn Asn Gln Ser Tyr Arg Thr
    130                 135                 140

Ala Val Ile Thr Gln Phe Asn Leu Thr Ser Ala Lys Leu Arg Glu Thr
145                 150                 155                 160

Ala Val Tyr Phe Ser Asn Leu Val Gly Tyr Glu Leu Leu Leu Leu Pro
                165                 170                 175

Ile Tyr Ala Gln Val Ala Asn Phe Asn Leu Leu Leu Ile Arg Asp Gly
            180                 185                 190

Leu Ile Asn Ala Gln Glu Trp Ser Leu Ala Arg Ser Ala Gly Asp Gln
        195                 200                 205

Leu Tyr Asn Thr Met Val Gln Tyr Thr Lys Glu Tyr Ile Ala His Ser
    210                 215                 220

Ile Thr Trp Tyr Asn Lys Gly Leu Asp Val Leu Arg Asn Lys Ser Asn
225                 230                 235                 240

Gly Gln Trp Ile Thr Phe Asn Asp Tyr Lys Arg Glu Met Thr Ile Gln
                245                 250                 255

Val Leu Asp Ile Leu Ala Leu Phe Ala Ser Tyr Asp Pro Arg Arg Tyr
            260                 265                 270

Pro Ala Asp Lys Ile Asp Asn Thr Lys Leu Ser Lys Thr Glu Phe Thr
        275                 280                 285

Arg Glu Ile Tyr Thr Ala Leu Val Glu Ser Pro Ser Ser Lys Ser Ile
    290                 295                 300

Ala Ala Leu Glu Ala Ala Leu Thr Arg Asp Val His Leu Phe Thr Trp
```

```
                305                 310                 315                 320
Leu Lys Arg Val Asp Phe Trp Thr Asn Thr Ile Tyr Gln Asp Leu Arg
                    325                 330                 335

Phe Leu Ser Ala Asn Lys Ile Gly Phe Ser Tyr Thr Asn Ser Ser Ala
                    340                 345                 350

Met Gln Glu Ser Gly Ile Tyr Gly Ser Ser Gly Phe Gly Ser Asn Leu
                    355                 360                 365

Thr His Gln Ile Gln Leu Asn Ser Asn Val Tyr Lys Thr Ser Ile Thr
                    370                 375                 380

Asp Thr Ser Ser Pro Ser Asn Arg Val Thr Lys Met Asp Phe Tyr Lys
385                 390                 395                 400

Ile Asp Gly Thr Leu Ala Ser Tyr Asn Ser Asn Ile Thr Pro Thr Pro
                    405                 410                 415

Glu Gly Leu Arg Thr Thr Phe Phe Gly Phe Ser Thr Asn Glu Asn Thr
                    420                 425                 430

Pro Asn Gln Pro Thr Val Asn Asp Tyr Thr His Ile Leu Ser Tyr Ile
                    435                 440                 445

Lys Thr Asp Val Ile Asp Tyr Asn Ser Asn Arg Val Ser Phe Ala Trp
                    450                 455                 460

Thr His Lys Ile Val Asp Pro Asn Asn Gln Ile Tyr Thr Asp Ala Ile
465                 470                 475                 480

Thr Gln Val Pro Ala Val Lys Ser Asn Phe Leu Asn Ala Thr Ala Lys
                    485                 490                 495

Val Ile Lys Gly Pro Gly His Thr Gly Gly Asp Leu Val Ala Leu Thr
                    500                 505                 510

Ser Asn Gly Thr Leu Ser Gly Arg Met Glu Ile Gln Cys Lys Thr Ser
                    515                 520                 525

Ile Phe Asn Asp Pro Thr Arg Ser Tyr Gly Leu Arg Ile Arg Tyr Ala
                    530                 535                 540

Ala Asn Ser Pro Ile Val Leu Asn Val Ser Tyr Val Leu Gln Gly Val
545                 550                 555                 560

Ser Arg Gly Thr Thr Ile Ser Thr Glu Ser Thr Phe Ser Arg Pro Asn
                    565                 570                 575

Asn Ile Ile Pro Thr Asp Leu Lys Tyr Glu Glu Phe Arg Tyr Lys Asp
                    580                 585                 590

Pro Phe Asp Ala Ile Val Pro Met Arg Leu Ser Ser Asn Gln Leu Ile
                    595                 600                 605

Thr Ile Ala Ile Gln Pro Leu Asn Met Thr Ser Asn Asn Gln Val Ile
                    610                 615                 620

Ile Asp Arg Ile Glu Ile Ile Pro Ile Thr Gln Ser Val Leu Asp Glu
625                 630                 635                 640

Thr Glu Asn Gln Asn Leu Glu Ser Glu Arg Glu Val Val Asn Ala Leu
                    645                 650                 655

Phe Thr Asn Asp Ala Lys Asp Ala Leu Asn Ile Gly Thr Thr Asp Tyr
                    660                 665                 670

Asp Ile Asp Gln Ala Ala Asn Leu Val Glu Cys Ile Ser Glu Glu Leu
                    675                 680                 685

Tyr Pro Lys Glu Lys Met Leu Leu Leu Asp Glu Val Lys Asn Ala Lys
                    690                 695                 700

Gln Leu Ser Gln Ser Arg Asn Val Leu Gln Asn Gly Asp Phe Glu Ser
705                 710                 715                 720

Ala Thr Leu Gly Trp Thr Thr Ser Asp Asn Ile Thr Ile Gln Glu Asp
                    725                 730                 735
```

```
Asp Pro Ile Phe Lys Gly His Tyr Leu His Met Ser Gly Ala Arg Asp
        740                 745                 750

Ile Asp Gly Thr Ile Phe Pro Thr Tyr Ile Phe Gln Lys Ile Asp Glu
        755                 760                 765

Ser Lys Leu Lys Pro Tyr Thr Arg Tyr Leu Val Arg Gly Phe Val Gly
        770                 775                 780

Ser Ser Lys Asp Val Glu Leu Val Val Ser Arg Tyr Gly Glu Glu Ile
785                 790                 795                 800

Asp Ala Ile Met Asn Val Pro Ala Asp Leu Asn Tyr Leu Tyr Pro Ser
                805                 810                 815

Thr Phe Asp Cys Glu Gly Ser Asn Arg Cys Glu Thr Ser Ala Val Pro
                820                 825                 830

Ala Asn Ile Gly Asn Thr Ser Asp Met Leu Tyr Ser Cys Gln Tyr Asp
                835                 840                 845

Thr Gly Lys Lys His Val Val Cys Gln Asp Ser His Gln Phe Ser Phe
                850                 855                 860

Thr Ile Asp Thr Gly Ala Leu Asp Thr Asn Glu Asn Ile Gly Val Trp
865                 870                 875                 880

Val Met Phe Lys Ile Ser Ser Pro Asp Gly Tyr Ala Ser Leu Asp Asn
                885                 890                 895

Leu Glu Val Ile Glu Gly Pro Ile Asp Gly Glu Ala Leu Ser Arg
                900                 905                 910

Val Lys His Met Glu Lys Lys Trp Asn Asp Gln Met Glu Ala Lys Arg
                915                 920                 925

Ser Glu Thr Gln Gln Ala Tyr Asp Val Ala Lys Gln Ala Ile Asp Ala
                930                 935                 940

Leu Phe Thr Asn Val Gln Asp Glu Ala Leu Gln Phe Asp Thr Thr Leu
945                 950                 955                 960

Ala Gln Ile Gln Tyr Ala Glu Tyr Leu Val Gln Ser Ile Pro Tyr Val
                965                 970                 975

Tyr Asn Asp Trp Leu Ser Asp Val Pro Gly Met Asn Tyr Asp Ile Tyr
                980                 985                 990

Val Glu Leu Asp Ala Arg Val Ala Gln Ala Arg Tyr Leu Tyr Asp Thr
                995                 1000                1005

Arg Asn Ile Ile Lys Asn Gly Asp Phe Thr Gln Gly Val Met Gly Trp
        1010                1015                1020

His Val Thr Gly Asn Ala Asp Val Gln Gln Ile Asp Gly Val Ser Val
1025                1030                1035                1040

Leu Val Leu Ser Asn Trp Ser Ala Gly Val Ser Gln Asn Val His Leu
                1045                1050                1055

Gln His Asn His Gly Tyr Val Leu Arg Val Ile Ala Lys Lys Glu Gly
                1060                1065                1070

Pro Gly Asn Gly Tyr Val Thr Leu Met Asp Cys Glu Glu Asn Gln Glu
                1075                1080                1085

Lys Leu Thr Phe Thr Ser Cys Glu Glu Gly Tyr Ile Thr Lys Thr Val
                1090                1095                1100

Asp Val Phe Pro Asp Thr Asp Arg Val Arg Ile Glu Ile Gly Glu Thr
1105                1110                1115                1120

Glu Gly Ser Phe Tyr Ile Glu Ser Ile Glu Leu Ile Cys Met Asn Glu
                1125                1130                1135

<210> SEQ ID NO 2
<211> LENGTH: 3684
```

<212> TYPE: DNA
<213> ORGANISM: Bacillus thuringiensis

<400> SEQUENCE: 2

```
gataagaatt gttcatagga atccgtatca attttttcaa ggaatatgta tttgcacttt      60
tggtcttttt aaatcgtatg aattcaaaat agtttatatc aatctttgtt acaccagaaa     120
aagattgtat ccaatgtgaa tatgggagga ataaatatga attcaggcta tccgttagcg     180
aatgacttac aagggtcaat gaaaaacacg aactataaag attggctagc catgtgtgaa     240
aataaccaac agtatggcgt taatccagct gcgattaatt cttcttcagt tagtaccgct     300
ttaaaagtag ctggagctat ccttaaattt gtaaacccac ctgcaggtac tgtcttaacc     360
gtacttagcg cggtgcttcc tattctttgg ccgactaata ctccaacgcc tgaaagagtt     420
tggaatgatt tcatgaccaa tacagggaat cttattgatc aaactgtaac agcttatgta     480
cgaacagatg caaatgcaaa aatgacggtt gtgaaagatt atttagatca atatacaact     540
aaatttaaca cttggaaaag agagcctaat aaccagtcct atagaacagc agtaataact     600
caatttaact taaccagtgc caaacttcga gagaccgcag tttattttag caacttagta     660
ggttatgaat tattgttatt accaatatac gcacaagtag caaatttcaa tttacttttta     720
ataagagatg gcctcataaa tgcacaagaa tggtctttag cacgtagtgc tggtgaccaa     780
ctatataaca ctatggtgca gtacactaaa gaatatattg cacatagcat tacatggtat     840
aataaaggtt tagatgtact tagaaataaa tctaatggac aatggattac gtttaatgat     900
tataaaagag agatgactat tcaagtatta gatatactcg ctcttttttgc cagttatgat     960
ccacgtcgat accctgcgga caaaatagat aatacgaaac tatcaaaaac agaatttaca    1020
agagagattt atacagcttt agtagaatct ccttctagta atctatagc agcactggag    1080
gcagcactta cacgagatgt tcatttattc acttggctaa agagagtaga tttctggacc    1140
aatactatat atcaagattt aagattttta tctgccaata aaattgggtt tcatatacea    1200
aattcttctg caatgcaaga aagtggaatt tatggaagtt ctggttttgg ttcaaatctt    1260
actcatcaaa ttcaacttaa ttctaatgtt tataaaactt ctatcacaga tactagctcc    1320
ccctctaatc gagttacaaa aatggatttc tacaaaattg atggtactct tgcctcttat    1380
aattcaaata taacaccaac tcctgaaggt ttaaggacca cattttttgg attttcaaca    1440
aatgagaaca cacctaatca accaactgta aatgattata cgcatatttt aagctatata    1500
aaaactgatg ttatagatta taacagtaac agggtttcat ttgcttggac acataagatt    1560
gttgacccta ataatcaaat atacacagat gctatcacac aagttccggc cgtaaaatct    1620
aacttcttga atgcaacagc taaagtaatc aagggacctg tcatacagg ggggatcta    1680
gttgctctta caagcaatgg tactctatca ggcagaatgg agattcaatg taaaacaagt    1740
attttttaatg atcctacaag aagttacgga ttacgcatac gttatgctgc aaatagtcca    1800
attgtattga atgtatcata tgtattacaa ggagtttcta gaggaacaac gattagtaca    1860
gaatctacgt tttcaagacc taataatata ataccactag atttaaaata tgaagagttt    1920
agatacaaag atccttttga tgcaattgta ccgatgagat tatcttctaa tcaactgata    1980
actatagcta ttcaaccatt aaacatgact tcaaataatc aagtgattat tgacagaatc    2040
gaaattattc caatcactca atctgtatta gatgagacag agaaccaaaa tttagaatca    2100
gaacgagaag ttgtgaatgc actgttaca aatgacgcga aagatgcatt aaacattgga    2160
acgacagatt atgacataga tcaagccgca aatcttgtgg aatgtatttc tgaagaatta    2220
```

-continued

```
tatccaaaag aaaaaatgct gttattagat gaagttaaaa atgcgaaaca acttagtcaa      2280
tctcgaaatg tacttcaaaa cggggatttt gaatcggcta cgcttggttg acaacaagt       2340 gataatatca caattcaaga agatgatcct atttttaaag ggcattacct tcatatgtct      2400
ggggcgagag acattgatgg tacgatattt ccgacctata tattccaaaa aattgatgaa      2460
tcaaaattaa aaccgtatac acgttaccta gtaaggggat ttgtaggaag tagtaaagat      2520
gtagaactag tggtttcacg ctatggggaa gaaattgatg ccatcatgaa tgttccagct      2580
gatttaaact atctgtatcc ttctacctttt gattgtgaag ggtctaatcg ttgtgagacg     2640
tccgctgtgc cggctaacat tgggaacact tctgatatgt tgtattcatg ccaatatgat     2700
acagggaaaa agcatgtcgt atgtcaggat tcccatcaat ttagttttcac tattgataca    2760 ggggcattag atacaaatga aaatataggg gtttgggtca tgtttaaaat atcttctcca     2820
gatggatacg catcattaga taatttagaa gtaattgaag aagggccaat agatggggaa     2880
gcactgtcac gcgtgaaaca catggagaag aaatggaacg atcaaatgga agcaaaacgt    2940
tcggaaacac aacaagcata tgatgtagcg aaacaagcca ttgatgcttt attcacaaat    3000
gtacaagatg aggctttaca gtttgatacg acactcgctc aaattcagta cgctgagtat    3060
ttggtacaat cgattccata tgtgtacaat gattggttgt cagatgttcc aggtatgaat    3120
tatgatatct atgtagagtt ggatgcacga gtggcacaag cgcgttattt gtatgataca    3180
agaaatatta ttaaaaatgg tgattttaca caaggggtaa tgggggtggca tgtaactgga   3240 aatgcagacg tacaacaaat agatggtgtt tctgtattgg ttctatctaa ttggagtgct    3300
ggcgtatctc aaaatgtcca tctccaacat aatcatgggt atgtcttacg tgttattgcc    3360 aaaaagaag gacctggaaa tgggtatgtc acgcttatgg attgtgagga gaatcaagaa    3420
aaattgacgt ttacgtcttg tgaagaagga tatattacga agacagtaga tgtattccca   3480
gatacagatc gtgtacgaat tgagataggc gaaaccgaag gttcgtttta tatcgaaagc    3540
attgaattaa tttgcatgaa cgagtgatta ataaaaaata actaaagctt taaaaaccat    3600
ggagaaagtt ttctccatgg ttttttaattt ctgcatttat taattctggt acaaaaaata    3660
tatagaaaac ataaaaaata gata                                            3684
```

<210> SEQ ID NO 3
<211> LENGTH: 648
<212> TYPE: PRT
<213> ORGANISM: Bacillus thuringiensis

<400> SEQUENCE: 3

```
Met His Tyr Tyr Gly Asn Arg Asn Glu Tyr Asp Ile Leu Asn Ala Ser
 1               5                  10                  15

Ser Asn Asp Ser Asn Met Ser Asn Thr Tyr Pro Arg Tyr Pro Leu Ala
            20                  25                  30

Asn Pro Gln Gln Asp Leu Met Gln Asn Thr Asn Tyr Lys Asp Trp Leu
        35                  40                  45

Asn Val Cys Glu Gly Tyr His Ile Glu Asn Pro Arg Glu Ala Ser Val
    50                  55                  60

Arg Ala Gly Leu Gly Lys Gly Leu Gly Ile Val Ser Thr Ile Val Gly
65                  70                  75                  80

Phe Phe Gly Gly Ser Ile Ile Leu Asp Thr Ile Gly Leu Phe Tyr Gln
                85                  90                  95

Ile Ser Glu Leu Leu Trp Pro Glu Asp Asp Thr Gln Gln Tyr Thr Trp
            100                 105                 110
```

-continued

```
Gln Asp Ile Met Asn His Val Glu Asp Leu Ile Asp Lys Arg Ile Thr
        115                 120                 125
Glu Val Ile Arg Gly Asn Ala Ile Arg Thr Leu Ala Asp Leu Gln Gly
    130                 135                 140
Lys Val Asp Asp Tyr Asn Asn Trp Leu Lys Lys Trp Lys Asp Asp Pro
145                 150                 155                 160
Lys Ser Thr Gly Asn Leu Ser Thr Leu Val Thr Lys Phe Thr Ala Leu
                165                 170                 175
Asp Ser Asp Phe Asn Gly Ala Ile Arg Thr Val Asn Asn Gln Gly Ser
                180                 185                 190
Pro Gly Tyr Glu Leu Leu Leu Pro Val Tyr Ala Gln Ile Ala Asn
            195                 200                 205
Leu His Leu Leu Leu Arg Asp Ala Gln Ile Tyr Gly Asp Lys Trp
    210                 215                 220
Trp Ser Ala Arg Ala Asn Ala Arg Asp Asn Tyr Tyr Gln Ile Gln Leu
225                 230                 235                 240
Glu Lys Thr Lys Glu Tyr Thr Glu Tyr Cys Ile Asn Trp Tyr Asn Lys
                245                 250                 255
Gly Leu Asn Asp Phe Arg Thr Ala Gly Gln Trp Val Asn Phe Asn Arg
            260                 265                 270
Tyr Arg Arg Glu Met Thr Leu Thr Val Leu Asp Ile Ile Ser Met Phe
        275                 280                 285
Pro Ile Tyr Asp Ala Arg Leu Tyr Pro Thr Glu Val Lys Thr Glu Leu
    290                 295                 300
Thr Arg Glu Ile Tyr Ser Asp Val Ile Asn Gly Glu Ile Tyr Gly Leu
305                 310                 315                 320
Met Thr Pro Tyr Phe Ser Phe Glu Lys Ala Glu Ser Leu Tyr Thr Arg
                325                 330                 335
Ala Pro His Leu Phe Thr Trp Leu Lys Gly Phe Arg Phe Val Thr Asn
            340                 345                 350
Ser Ile Ser Tyr Trp Thr Phe Leu Ser Gly Gly Gln Asn Lys Tyr Ser
        355                 360                 365
Tyr Thr Asn Asn Ser Ser Ile Asn Glu Gly Ser Phe Arg Gly Gln Asp
    370                 375                 380
Thr Asp Tyr Gly Gly Thr Ser Ser Thr Ile Asn Ile Pro Ser Asn Ser
385                 390                 395                 400
Tyr Val Tyr Asn Leu Trp Thr Glu Asn Tyr Glu Tyr Ile Tyr Pro Trp
                405                 410                 415
Gly Asp Pro Val Asn Ile Thr Lys Met Asn Phe Ser Val Thr Asp Asn
            420                 425                 430
Asn Ser Ser Lys Glu Leu Ile Tyr Gly Ala His Arg Thr Asn Lys Pro
        435                 440                 445
Val Val Arg Thr Asp Phe Asp Phe Leu Thr Asn Lys Glu Gly Thr Glu
    450                 455                 460
Leu Ala Lys Tyr Asn Asp Tyr Asn His Ile Leu Ser Tyr Met Leu Ile
465                 470                 475                 480
Asn Gly Glu Thr Phe Gly Gln Lys Arg His Gly Tyr Ser Phe Ala Phe
                485                 490                 495
Thr His Ser Ser Val Asp Pro Asn Asn Thr Ile Ala Ala Asn Lys Ile
            500                 505                 510
Thr Gln Ile Pro Val Val Lys Ala Ser Ser Ile Asn Gly Ser Ile Ser
        515                 520                 525
Ile Glu Lys Gly Pro Gly Phe Thr Gly Gly Asp Leu Val Lys Met Arg
```

-continued

```
    530                 535                 540

Ala Asp Ser Gly Leu Thr Met Arg Phe Lys Ala Glu Leu Leu Asp Lys
545                 550                 555                 560

Lys Tyr Arg Val Arg Ile Arg Tyr Lys Cys Asn Tyr Ser Ser Lys Leu
                565                 570                 575

Ile Leu Arg Lys Trp Lys Gly Glu Gly Tyr Ile Gln Gln Gln Ile His
            580                 585                 590

Asn Ile Ser Pro Thr Tyr Gly Ala Phe Ser Tyr Leu Glu Ser Phe Thr
        595                 600                 605

Ile Thr Thr Thr Glu Asn Ile Phe Asp Leu Thr Met Glu Val Thr Tyr
    610                 615                 620

Pro Tyr Gly Arg Gln Phe Val Glu Asp Ile Pro Ser Leu Ile Leu Asp
625                 630                 635                 640

Lys Ile Glu Phe Leu Pro Thr Asn
                645

<210> SEQ ID NO 4
<211> LENGTH: 4391
<212> TYPE: DNA
<213> ORGANISM: Bacillus thuringiensis

<400> SEQUENCE: 4
gaaaattcga gaattaatca gacatgcagg cgccaaaaac gtagtattgg atggcagaga      60
tggagtaatg aatatctcta tggtgtacta gggctctatt gggactggaa agttcgtccc     120
cttgaaagct caggaagata ttgataaaag tgtctgccat ttgataggtc tcataaccct     180
tttgatgaag tttatggggt gagctgcttg agggaaaacc tcacgagcag ttcttatggg     240
gaggggctgg aaacgggtta taactgatac cgcgccagtc ctttacccga caacgaactt     300
ttgcttggtt agaaaattac cgcaggcttt ggaaaaactg tgaacgaaca cttgaaaata     360
gcagacaaag ttgcttattg gcagctgtgg ctattttatt aaaaagattc caaacaggtt     420
ctcagaaaat agttgtaatt catcttgaat cgaaagattc ataaaaaacg tcatcctttc     480
tagcttttta gaaagaataa cgtttttga cacttggggg tagtcttatt tcttaagttg     540
atgggcatgc aacagaaccc taaaaaatca ataattcaac aaaaataatg gggatatttg     600
ttgaattatt gcaacaggaa tacatacgta gattgcgaat atttagaagt acaccctaca     660
tattattggt taggtggaat gaattataaa aaatgatggg aataagggag gaacgaagat     720
gcattattat gggaatagga atgaatatga catattaaat gcttcatcaa acgattcaaa     780
catgtctaat acttatccga ggtatccgtt agcaaatcca caacaagatt taatgcaaaa     840
tacaaattat aaagattggc ttaatgtatg tgaagggtat catatagaaa atcctagaga     900
agcaagcgtt agagctggac ttggtaaggg attaggtata gttagtacaa tcgtagggtt     960
ctttggtggt tctattatct tagatacaat tggattgttt taccaaattt cagagctact    1020
ttggccagag gatgataccc agcaatacac ttggcaagat attatgaatc atgtagaaga    1080
tcttatagac aaacgaataa ctgaggttat acgaggaaat gcaattagaa cattagcaga    1140
tttacagggt aaagttgatg attataacaa ttggttgaag aaatggaaag acgatccaaa    1200
atctacaggt aatttaagca ccttagtaac caagtttacg gctcttgatt cagattttaa    1260
tggtgctata aggacagtta ataatcaggg gagtccaggt tatgagttac ttttattgcc    1320
tgtctatgca caaattgcga atctgcattt acttttatta cgggatgctc agatttatgg    1380
agataaatgg tggagcgcac gagctaatgc tcgtgataat tattaccaaa tacaattaga    1440
```

```
gaaaacaaag gaatatacag aatattgtat aaattggtat aataagggtt taaatgattt    1500
tagaacagca ggtcaatggg taaactttaa tcgttatcgt agagaaatga ctcttactgt    1560
attagatatt atttcaatgt tccctattta tgacgcgaga ttatatccta cagaagtaaa    1620
aaccgaacta actagggaaa tttattcaga tgttattaat ggggagatat atggacttat    1680
gactccttat ttttcttttg agaaagctga atcactttat acaagggcac cccatctctt    1740
cacttggcta aaaggatttc gatttgtaac caattctatt tcttattgga catttttatc    1800
aggtggtcaa ataagtatt cttatactaa taattctagt attaacgagg ctcttttag     1860 gggacaggac acagattatg gtgggacttc ttctaccatt aatattccat caaattcgta    1920
tgtatataat ttatggacgg aaaattatga atatatttat ccttggggtg atcctgtaaa    1980
tattacaaaa atgaattttt ctgtaacaga taataattct tcaaaagaat taatttatgg    2040
tgcacacaga acgaataaac ctgttgttcg gacagatttt gattttctca ctaataaaga    2100
gggaactgag ttagcaaaat ataatgatta taatcatatt ttatcctata tgttaattaa    2160
tggggaaacg tttggtcaga acgtcatgg ttattcgttt gcttttacac atagtagtgt     2220
tgatcctaat ataccattg cagcgaataa aattacgcaa attcctgtag tgaaagcttc     2280
gagtataaat ggatcgattt caattgaaaa aggtcccgga tttacgggag agatttggt     2340 aaagatgaga gcagattcag gtttaactat gcgttttaaa gctgaattat tagataaaaa    2400
atatcgtgtt cgaatacgtt ataaatgtaa ctacagttct aaattaatac tacgaaaatg    2460
gaaaggggaa ggttatatac aacaacaaat tcacaatatt tctcccacat atggagcctt    2520
ttcttattta gagtctttta ctataactac gacagaaaat atatttgatt tgacaatgga    2580
ggtaacatat ccgtatggta gacagtttgt tgaagatata ccatctctta tattagataa    2640
aatcgaattc ctcccaacta actgatacca ttcacaggaa atatgaggaa aaatatgaat    2700
tagaaagatc acaggaaaca tttaatagta tatttgttga ttaaaacaaa gtactaacgt    2760
agatggtata gctgtttgaa aaaataagaa aaaaggttgt gaattttatg cttacaagtg    2820
gtgcgaaaaa tatgttaaaa ctcgaaacga cagattatga aatagatcaa atggcgaatg    2880
ctatagaaaa tatgtcaggt gaacaatatt cacaggaaaa aatgatgcaa tggcatgaca    2940
taaaatatgc caaacaattg agtcaagcac gtaatttact tcaaaatggt gattttgagg    3000
atttatttag tggatggact acaagtaatc agatgtccat tcaggcagat aatgcaactt    3060
ttaaagggaa ctatctgcat atgtctgggg cgagagacat atatggaacg atattcccaa    3120
cgtatatata ccaaaaaatt gatgaatcca aattaaaacc gtatacgcgt tatctagtca    3180
ggggatttgt gggaagtagt aaagatctag aattaatggt aatgcgttat ggaaaagaaa    3240
ttgatacagt aatgaatgta ccaaatgaca taccgtacgt accttctatg ccggtctgta    3300
acgaattata tgatggtcaa caaccgtatc caaataggca tgtaggatat tataatccaa    3360
tgccagtttc tcagccttct tacacatccg atacttgtca gtgtacgccc ggcaaaaaac    3420
atgtggtatg tcatgattct catcaattca gtttcatat tgatacgggg gaagtagatt      3480
acaatacaaa tctaggaatt tgggtgttgt ttaaaatctc ttcacccgat ggctacgcga    3540
cattagataa tttagaagta attgaagagg accagtaagg aggcgaagca gtgacacatg    3600
taaaacaaaa ggaaagaaa tggaatcagc aaatggagaa aaagcgcatg gaaacaaagc     3660
gagtctatga ccgagcaaaa caggcggtag atgcattatt tacaggagaa gagttaaact    3720
atgatgttac attgtcacac attaagaacg ccgatgattt ggtacagtcg attccatatg    3780
tacacaatga gtggttaccg gattttccag gcatgaacta tgatatatac caagagttaa    3840
```

```
acgcgcgtat catgcaagca cgctatttat acgatgcacg aaatgtcata acaaatgggg    3900
attttgcaca aggattacaa gggtggcatg cggaaggaaa agtagaagta cagcaaatga    3960
acggaacgtc tgtattagtc ttatccaatt ggagctctgg agtatctcaa aaccttcatg    4020
tccaacatcc acatggatat ctgttacgtg tgagtgcgaa aaaagaaggg tctgggaaag    4080
gctatgtaac gaggatgagt tgtaatggta agcaggaaac acttacgttt acgtcctgtg    4140
acggaggata tatgacaaaa acggtagagg tattcccaga aagtgatcgt gtacgaattg    4200
aaattgggga gaccgaaggt tcgtttttata ttgaaagcat cgaattgatt tgtatgaacg    4260
gatatactag caataataac cagaatatga gtaatatgta tgatcaaagt tatagtggga    4320
attatagtca gaatactagc gatatgtatg atcaaggagg ttctgttgca agtttgaaa    4380 aagaatagaa t                                                       4391
```

<210> SEQ ID NO 5
<211> LENGTH: 198
<212> TYPE: PRT
<213> ORGANISM: Bacillus thuringiensis

<400> SEQUENCE: 5

```
Trp Leu Asp Ser Leu Asn Phe Tyr Glu Lys Ala Gln Thr Thr Pro Asn
 1               5                  10                  15

Asn Phe Phe Thr Ser His Tyr Asn Met Phe His Tyr Thr Leu Asp Asn
            20                  25                  30

Ile Ser Gln Lys Ser Ser Val Phe Gly Asn His Asn Val Thr Asp Lys
        35                  40                  45

Leu Lys Ser Leu Gly Leu Ala Thr Asn Ile Tyr Ile Phe Leu Leu Asn
    50                  55                  60

Val Ile Ser Leu Asp Asn Lys Tyr Leu Asn Asp Tyr Asn Asn Ile Ser
65                  70                  75                  80

Lys Met Asp Phe Phe Ile Thr Asn Gly Thr Arg Leu Leu Glu Lys Glu
                85                  90                  95

Leu Thr Ala Gly Ser Gly Gln Ile Thr Tyr Asp Val Asn Lys Asn Ile
            100                 105                 110

Phe Gly Leu Pro Ile Leu Lys Arg Arg Glu Asn Gln Gly Asn Pro Thr
        115                 120                 125

Leu Phe Pro Thr Tyr Asp Asn Tyr Ser His Ile Leu Ser Phe Ile Lys
    130                 135                 140

Ser Leu Ser Ile Pro Ala Thr Tyr Lys Thr Gln Val Tyr Thr Phe Ala
145                 150                 155                 160

Trp Thr His Ser Ser Val Asp Pro Lys Asn Thr Ile Tyr Thr His Leu
                165                 170                 175

Thr Thr Gln Ile Pro Ala Val Lys Ala Asn Ser Leu Gly Thr Ala Ser
            180                 185                 190

Lys Val Val Gln Gly Pro
        195
```

<210> SEQ ID NO 6
<211> LENGTH: 182
<212> TYPE: PRT
<213> ORGANISM: Bacillus thuringiensis

<400> SEQUENCE: 6

```
Trp Leu Lys Arg Val Asp Phe Trp Thr Asn Thr Ile Tyr Gln Asp Leu
 1               5                  10                  15
```

```
Arg Phe Leu Ser Ala Asn Lys Ile Gly Phe Ser Tyr Thr Asn Ser Ser
                20                  25                  30

Ala Met Gln Glu Ser Gly Ile Tyr Gly Ser Ser Gly Phe Gly Ser Asn
            35                  40                  45

Leu Thr His Gln Ile Gln Leu Asn Ser Asn Val Tyr Lys Thr Ser Ile
        50                  55                  60

Thr Asp Thr Ser Ser Pro Ser Asn Arg Val Thr Lys Met Asp Phe Tyr
 65                  70                  75                  80

Lys Ile Asp Gly Thr Leu Ala Ser Tyr Asn Ser Asn Ile Thr Pro Thr
                85                  90                  95

Pro Glu Gly Leu Arg Thr Thr Phe Phe Gly Phe Ser Thr Asn Glu Asn
            100                 105                 110

Thr Pro Asn Gln Pro Thr Val Asn Asp Tyr Thr His Ile Leu Ser Tyr
        115                 120                 125

Ile Lys Thr Asp Val Ile Asp Tyr Asn Ser Asn Arg Val Ser Phe Ala
130                 135                 140

Trp Thr His Lys Ile Val Asp Pro Asn Asn Gln Ile Tyr Thr Asp Ala
145                 150                 155                 160

Ile Thr Gln Val Pro Ala Val Lys Ser Asn Phe Leu Asn Ala Thr Ala
                165                 170                 175

Lys Val Ile Lys Gly Pro
            180

<210> SEQ ID NO 7
<211> LENGTH: 92
<212> TYPE: PRT
<213> ORGANISM: Bacillus thuringiensis

<400> SEQUENCE: 7

Ser Ile Ala Ala Leu Glu Ala Ala Leu Thr Arg Asp Val His Leu Phe
 1               5                  10                  15

Thr Trp Leu Lys Arg Val Asp Phe Trp Thr Asn Thr Ile Tyr Gln Asp
                20                  25                  30

Leu Arg Phe Leu Ser Ala Asn Lys Ile Gly Phe Ser Tyr Thr Asn Ser
            35                  40                  45

Ser Ala Met Gln Glu Ser Gly Ile Tyr Gly Ser Ser Gly Phe Gly Ser
        50                  55                  60

Asn Leu Thr His Gln Ile Gln Leu Asn Ser Asn Val Tyr Lys Thr Ser
 65                  70                  75                  80

Ile Thr Asp Thr Ser Ser Pro Ser Asn Arg Val Thr
                85                  90

<210> SEQ ID NO 8
<211> LENGTH: 99
<212> TYPE: PRT
<213> ORGANISM: Bacillus thuringiensis

<400> SEQUENCE: 8

Phe Ser Phe Glu Lys Ala Glu Ser Leu Tyr Thr Arg Ala Pro His Leu
 1               5                  10                  15

Phe Thr Trp Leu Lys Gly Phe Arg Phe Val Thr Asn Ser Ile Ser Tyr
                20                  25                  30

Trp Thr Phe Leu Ser Gly Gly Gln Asn Lys Tyr Ser Tyr Thr Asn Asn
            35                  40                  45

Ser Ser Ile Asn Glu Gly Ser Phe Arg Gly Gln Asp Thr Asp Tyr Gly
        50                  55                  60
```

-continued

```
Gly Thr Ser Ser Thr Ile Asn Ile Pro Ser Asn Ser Tyr Val Tyr Asn
 65                  70                  75                  80

Leu Trp Thr Glu Asn Tyr Glu Tyr Ile Tyr Pro Trp Gly Asp Pro Val
                 85                  90                  95

Asn Ile Thr
```

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 9
gattggatcc aatgtaatat gggag 25

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer
<400> SEQUENCE: 10
tatttttggt accagaatta ataaatgcag 30

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 11
ggtctttagc agctagtgct ggtgacc 27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 12
ggtcaccagc actagctgct aaagacc 27

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 13
accaatactc aaactacaga tttaagattt ttatc 35

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 14
tcttaaatct gaagtttgag tattggtcca gaaatc 36

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 15
ctaatcgagt taatgattat acaaaaatgg atttc                                    35

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 16 cattttgta taatcattaa ctcgattaga gggtattc                                  38

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 17
gatgttatac ctgcgactta taacagtaac agggtttc                                 38

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 18
ctgttataag tcgcaggtat aacatcagtt tttatatag                                39

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 19
gatgttatag ctgcgactta taacagtaac agggtttc                                 38

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 20
ctgttataag tcgcagctat aacatcagtt tttatatag                                39

<210> SEQ ID NO 21
<211> LENGTH: 38
<212> TYPE: DNA
<213> ORGANISM: Artificial Sequence
<220> FEATURE:

<223> OTHER INFORMATION: Description of Artificial Sequence: Primer

<400> SEQUENCE: 21
gatgttatag gtgcgactta aacagtaac agggtttc                                38

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 22
ctgttataag tcgcacctat aacatcagtt tttatatag                              39

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 23
gatgttatag gtgcggttta aacagtaac agggtttc                                38

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 24
ctgttataaa gcgcacctat aacatcagtt tttatatag                              39

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 25
gatgttatac ctgcggctta aacagtaac agggtttc                                38

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 26
ctgttataag tcgcaggtat aacatcagtt tttatatag                              39

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 27
gatgttatag ctgcggctta aacagtaac agggtttc                                38

```
<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 28
ctgttataag ccgcagctat aacatcagtt tttatatag                          39

<210> SEQ ID NO 29
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 29
accaattcta tttatcaaga cttaagattt ttatcaggtg gtc                     43

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 30
tgataaaaat cttaagtctt gataaataga attggttaca aatc                    44

<210> SEQ ID NO 31
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 31
aattatgaat atattcctgt aaatattaca aaaatgaatt tttc                    44

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 32
atttacagga atatattcat aattttccgt ccataaatta tatac                   45

<210> SEQ ID NO 33
<211> LENGTH: 4
<212> TYPE: PRT
<213> ORGANISM: Bacillus thuringiensis

<400> SEQUENCE: 33

Tyr Gln Asp Leu
 1

<210> SEQ ID NO 34
<211> LENGTH: 4
<212> TYPE: PRT
<213> ORGANISM: Bacillus thuringiensis

<400> SEQUENCE: 34

Asn Asn Ile Ile
```

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 35
cgttttcaag acctgctaat ataataccta cag          33

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 36
cgttttcaag acctaatgct ataataccta cagatttaaa atatg          45

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 37
cgttttcaag acctaataat gcaataccta cagatttaaa atatg          45

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 38
cgttttcaag acctaataat atagcaccta cagatttaaa atatg          45

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 39
cgttttcaag acctaataat tttataccta cagatttaaa atatg          45

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 40
cgttttcaag acctaataat atatttccta cagatttaaa atatg          45

<210> SEQ ID NO 41
<211> LENGTH: 35
<212> TYPE: DNA
<213> ORGANISM: Artificial Sequence -continued

```
<220> FEATURE:
<223> OTHER INFORMATION: Description of Artificial Sequence: Primer

<400> SEQUENCE: 41
aggtcttgaa aacgtagatt ctgtactaat cgttg                                35

<210> SEQ ID NO 42
<211> LENGTH: 4
<212> TYPE: PRT
<213> ORGANISM: Bacillus thuringiensis

<400> SEQUENCE: 42

Ser Tyr Trp Thr
  1

<210> SEQ ID NO 43
<211> LENGTH: 5
<212> TYPE: PRT
<213> ORGANISM: Bacillus thuringiensis

<400> SEQUENCE: 43

Tyr Pro Trp Gly Asp
  1               5
```